US007094413B2

(12) United States Patent
Buelow et al.

(10) Patent No.: US 7,094,413 B2
(45) Date of Patent: Aug. 22, 2006

(54) COMBINED THERAPY FOR TREATMENT OF HIV INFECTION

(75) Inventors: Roland Buelow, Mountain View, CA (US); Suhasini Iyer, San Ramon, CA (US); Satya Dandekar, Davis, CA (US)

(73) Assignees: SangStat Medical Corporation, Cambridge, MA (US); The Regents of the University of California, Oakland, CA (US)

( * ) Notice: Subject to any disclaimer, the term of this patent is extended or adjusted under 35 U.S.C. 154(b) by 176 days.

(21) Appl. No.: 10/351,608

(22) Filed: Jan. 24, 2003

(65) Prior Publication Data

US 2004/0127422 A1 Jul. 1, 2004

Related U.S. Application Data

(60) Provisional application No. 60/351,925, filed on Jan. 24, 2002.

(51) Int. Cl.
*A61K 45/00* (2006.01)
(52) U.S. Cl. .................. 424/278.1; 514/2; 514/15; 530/300; 536/28.54
(58) Field of Classification Search ................ 530/300, 530/28.54; 514/2, 15; 536/28.54; 424/278.1
See application file for complete search history.

(56) References Cited

U.S. PATENT DOCUMENTS

| 5,385,888 | A | 1/1995 | Goodenow et al. |
| 5,723,128 | A | 3/1998 | Clayberger et al. |
| 5,753,625 | A | 5/1998 | Buelow |
| 6,162,434 | A | 12/2000 | Buelow et al. |
| 6,696,545 | B1 | 2/2004 | Buelow et al. |

FOREIGN PATENT DOCUMENTS

| WO | WO 88/05784 A1 | 8/1988 |
| WO | WO 90/10016 A1 | 9/1990 |
| WO | WO 93/08817 A1 | 5/1993 |
| WO | WO 93/17699 A1 | 9/1993 |
| WO | WO 94/02162 A1 | 2/1994 |
| WO | WO 95/13288 A1 | 5/1995 |
| WO | WO 96/22306 A1 | 7/1996 |
| WO | WO 96/35443 A1 | 11/1996 |
| WO | WO 97/24140 A1 | 7/1997 |
| WO | WO 97/44052 A1 | 11/1997 |
| WO | WO 97/44351 A1 | 11/1997 |
| WO | WO 98/46633 A1 | 10/1998 |

OTHER PUBLICATIONS

Kaminski et al. (from IDS, Alternative Medicine Rev. 1998 vol. 3, No. 1, pp. 40-53.*
Alkhatib, G., et al., "CC CKR5: a RANTES, MIP-1α, MIP-1β receptor as a fusion cofactor for macrophage topic HIV-1," *Science* 272(5270):1955-1958 (Jun. 1996).

Autran, B., et al., "Positive Effects of Combined Antiretroviral Therapy on CD4+ T Cell Homeostasis and Function in Advanced HIV Disease," *Science* 277(5322):112-116 (Jul. 1997).
Benveniste, O., et al., "Interleukin 1 β, interleukin 6, tumor necrosis factor α, and interleukin 10 responses in peripheral blood mononuclear cells of cynomolgus macaques during acute infection with SIVmac251," *AIDS Res. Hum. Retroviruses* 12(3):241-250 (Feb. 1996).
Biswas, D.K., et al., "Inhibition of HIV-1 replication by combination of a novel inhibitor of TNF-α with AZT," *J. Acquir. Immune Defic. Syndr. Hum. Retrovirol.* 18(5):426-434 (Aug. 1998).
Blaese, R.M., et al., "Gene Therapy for Primary Immunodeficiency Disease," *Immunodefic. Rev.* 3(4):329-349 (1992).
Bogner, J.R., et al., "Th1/Th2 shift in HIV lymph nodes: no contribution of CD60 cells," *Infection* 29(1):32-36 (Jan.-Feb. 2001).
Boismenu, R., et al., "Orally administered RDP58 reduces the severity of dextran sodium sulphate induced colitis," *Ann Rheum. Dis.* 61 Suppl. 2:ii19-24 (Nov. 2002).
Buelow, R., et al., "Immunomodulation by soluble HLA class I," *Transplantation* 59(5):649-654 (Mar. 1995).
Buelow, R., et al., "Prolongation of skin allograft survival in mice following administration of ALLOTRAP," *Transplantation* 59(4);455-460 (1995).
Cantoni, L., et al., "Interleukin-1 and tumour necrosis factor induce hepatic heme oxygenase feedback regulation by glucocorticoids," *Biochem. J.* 279(Pt 3):891-894 (1991).
Chêne, L., et al., "Thymocyte-Thymic Epithelial Cell Interaction Leads to High-Level Replication of Human Immunodeficiency Virus Exclusively In Mature CD4+ CD8− CD3+ Thymocytes: a Critical Role for Tumor Necrosis Factor and Interleukin-7," *J. Virol.* 73(9):7533-7542 (Sep. 1999).
Clayette, P., et al., "Effects of RP 55778, a tumor necrosis factor alpha synthesis inhibitor, on antiviral activity of dideoxynucleosides," *Antimicrob. Agents Chemother.* 41(4):875-877 (Apr. 1997).
Cuturi, M.C., et al., "Prolongation of Allogeneic Heart Graft Survival in Rats by Administration of a Peptide (a.a. 75-84) from the Alpha 1 Helix of the First Domain of HLA-B7 01," *Transplantation* 59(5):661-669 (1995).

(Continued)

*Primary Examiner*—James Housel
*Assistant Examiner*—Myron G. Hill
(74) *Attorney, Agent, or Firm*—Dorsey & Whitney LLP; Todd A. Lorenz

(57) ABSTRACT

The present invention relates to pharmaceutical preparations and methods for treating individuals infected with the human immunodeficiency virus (HIV). The pharmaceutical preparations comprise an immunomodulating agent and a anti-retroviral compound. The pharmaceutical preparations are used to treat HIV infected patients, particularly for gastrointestinal complications arising from viral infection. In addition, the pharmaceutical preparations of the present invention have the effect of raising the levels of CD4+ single positive and CD4+ and CD8+ double positive T cells, thus promoting restoration and normalization of the immune system following HIV infection.

19 Claims, 14 Drawing Sheets

OTHER PUBLICATIONS

Dalgleish, A., et al., "The CD4 (T4) antigen is an essential component of the receptor for the AIDS retrovirus," *Nature* 312(5996):763-767 (Jan. 1984).

De Waal Malefyt, R., et al., "Interleukin 10 (IL-10) Inhibits Cytokine Synthesis by Human Monocytes: An Autoregulatory Role of IL-10 Produced by Monocytes," *J. Exp. Med.* 174(5):1209-1222 (Nov. 1991).

Feng, Y., et al., "HIV-1 entry cofactor: functional cDNA cloning of a seven transmembrane, G protein-coupled receptor," *Science* 272(5263):872-877 (May 1996).

Fiorentino, D., et al., "IL-10 inhibits cytokine production by activated macrophages," *J. Immunol.* 147(11):3815-3822 (Dec. 1991).

Fujinaga, K., et al., "Generation of endogenous tumour necrosis factor-alpha in MOLT-4 cells during the acute replication phase of human immunodeficiency virus type 1 determines the subsequent latent infection," *J. Gen. Virol.* 79(Pt 2):221-229 (Feb. 1998).

Gao, L., et al., "Both L- and D-isomers of Allotrap 2702 Prolong Cardiac Allograft Survival in Mice," *J. Heart Lung Transplant.* 15(1):78-87 (1996).

Gorochov, G., et al., "Perturbation of CD4+ and CD8+ T-cell reportoires during progression to AIDS and regulation of the CD4+ repertoire during antiviral therapy," *Nat. Med.* 4(2):215-221 (Feb. 1998).

Grassy, G., et al., "Computer-assisted Rational Design of Immunosuppressive Compounds," *Nat Biotechnol.* 16(8):748-752 (1998).

Grassy, G., et al., "Variable mapping of structure-activity relationships: Application to 17-spirolactone derivatives with mineralocorticoid activity," *J. Mol. Graph.* 13(6):356-357 (Dec. 1995).

Guillemard, E., et al., "Interkeukin-7 and infection itself by human immunodeficiency virus 1 favor virus persistence in mature $CD4^+$ $CD8^-$ $CD3^+$ thymocytes through sustained induction of Bcl-2," *Blood* 98(7):2166-2174 (Oct. 2001).

Haiech, J., et al., "Use of TSAR as a new tool to analyze the molecular dynamics trajectories of proteins," *J. Mol. Graph.* 13(1):46-48 (Feb. 1995).

Haslett, P., et al., "Thalidomide Stimulates T Cell Responses and Interleukin 12 Production in HIV-Infected Patients," *AIDS Res. Hum. Retroviruses* 15(13):1169-1179 (1999).

Heguy, A., et al., "Isolation and characterization of the fungal metabolite 3-O-methylviridicatin as an inhibitor of tumour necrosis factor α-induced human immunodeficiency virus replication," *Antivir. Chem. Chemother.* 9(2):149-155 (Mar. 1998).

Hejdeman, B., et al., "Clinical and Immunological Benefits from Highly Active Antiretroviral Therapy in Spite of Limited Viral Load Reduction in HIV Type 1 Infection," *AIDS Res. Hum. Retroviruses* 17(4):277-286 (2001).

Herbein, G., et al., "Tumor necrosis factor α inhibits entry of human immunodeficiency virus type 1 into primary human macrophages: a selective role for the 75-kilodalton receptor," *J. Virol.* 70(11):7388-7397 (Nov. 1996).

Imlach, S., et al., "Activated Peripheral CD8 Lymphocytes Express CD4 In Vivo and Are Targets for Infection by Human Immunodeficiency Virus Type 1," *J. Virol.* 75(23):11555-11564 (Dec. 2001).

Iyer, S., et al., "Characterization and Biological Significance of Immunosuppressive Peptide D2702.75-84 (E—V) Binding Protein," *J. Biol. Chem.* 273(5):2692-2697 (Jan. 1998).

Iyer, S. et al., "Inhibition of Tumor Necrosis Factor mRNA Translation by a Rationally Designed Immunomodulatory Peptide," *J. Biol. Chem.* 275(22):17051-17057 (2000).

Iyer, S., et al., "Rational design and development of RDP58," *Curr. Pharm. Des.* 8(24):2217-2229 (Nov. 2002).

Kaminski, M., et al., "AIDS Wasting Syndrome as an Entero-Metabolic Disorder: The Gut Hypothesis," *Alt. Med. Rev.* 3(1):40-53 (1998).

Kaslow, R., et al., "Polymorphisms in HLA Class I Genes Associated with both Favorable Prognosis of Human Immunodeficiency Virus (HIV) Type 1 Infection and Positive Cytotoxic T-Lymphocyte Responses to ALVAC-HIV Recombinant Canarypox Vaccines," *J. Virol.* 75(18):8681-8689 (Sep. 2001).

Kotler, D., "Characterization of Intestinal Disease Associated with Human Immunodeficiency Virus Infection and Response to Antiretroviral Therapy," *J. Infect. Dis.* 179(Supp. 3):S454-S456 (1999).

Lane, B., et al., "TNF-α Inhibits HIV-1 Replication in Peripheral Blood Monocytes and Alveolar Macrophages by Inducing the Production of RANTES and Decreasing C-C Chemokine Receptor 5 (CC55) Expression," *J. Immunol.* 163:3653-3661 (1999).

Lazdins, J.K., et al., "Membrane tumor necrosis factor (TNF) induced cooperative signaling of TNFR60 and TNFR80 favors induction of cell death rather than virus production in HIV-infected T cells," *J. Exp. Med.* 185(1);81-90 (Jan. 1997).

Macias, J., et al., "Usefulness of route of transmission, absolute CD8+ T-cell counts, an levels of serum tumor necrosis factor α as predictors of survival of HIV-1-infected patients with very low CD4+ T-cell counts," *Eur. J. Clin. Microbiol. Infect. Dis.* 20(4):253-259 (Apr. 2001).

Magee, C.C., et al., "In Vitro and in Vivo Immunomodulatory Effects of RDP1258, a Novel Synthetic Peptide," *J. Am. Soc. Nephrol.* 10:1997-2005 (1999).

Manolios, N., et al., "T-cell antigen receptor transmembraned peptides modulate T-cell function and T cell-mediated disease," *Nat. Med.* 3(1):84-88 (Jan. 1997).

Marriott, J., et al., "A Double-Blind Placebo-Controlled Phase II Trial of Thalidomide in Asymptomatic HIV-Positive Patients: Clinical Tolerance and Effect on Activation Markers and Cytokines," *AIDS Res. Hum. Retroviruses* 13(18):1625-1631 (1997).

Marshall, W., et al., "Signaling Through the Lymphotoxin-β Receptor Stimulates HIV-1 Replication Alone and in Cooperation with Soluble or Membrane-Bound TNF-α," *J. Immunol.* 162(10):6016-6023 (May 1999).

Moreira, A., et al., "Thalidomide and Thalidomide Analogs Reduce HIV Type 1 Replication in Human Macrophages *in Vitro,*" *AIDS Res. Hum. Retroviruses* 13(10):857-863 (1997).

Muñoz-Fernández, M., et al., "Replication of human immunodeficiency virus-1 in primary human T cells is dependent on the autokine secretion of tumor necrosis factor through the control of nuclear factor-κB activation," *J. Allergy Clin. Immunol.* 100(6 Pt 1):838-845 (Dec. 1997).

Nisco, S., et al., "Induction of Allograft Tolerance in Rats by an HLA Class-I-derived Peptide and Cyclosporine A," *J Immunol.* 152(8):3786-3792 (1994).

Oberyszyn, T.M., et al., "Inhibition of Cutaneous UV Light-Induced tumor Necrosis Factor-a Protein Production by Allotrap 1258, a Novel Immunomodulatory Peptide," *Photochemistry and Photobiology* 73(2):184-190 (2001).

Odeh, M., "The role of tumor necrosis factor-α in acquired immunodeficiency syndrome," *J. Intern. Med.* 228(6):549-556 (Dec. 1990).

Okamoto, M., "HIV-1-infected myelomonocytic cells are resistant to Fas-mediated apoptosis: effect of tumor necrosis factor-α on their Fas expression and apoptosis," *Med. Microbiol. Immunol.* 186:11-17 (1997).

Okamoto, M., et al., "Suppression of cytokine production and neural cell death by the anti-inflammatory alkaloid cepharanthine: a potential agent against HIV-1 encephalopathy," *Biochem. Pharmacol.* 62(6):747-753 (Sep. 2001).

Pakker, N., et al., "Biphasic kinetics of peripheral blood T cells after triple combination therapy in HIV-1 infection: A composite of redistribution and proliferation," *Nat. Med.* 4(2):208-214 (Feb. 1998).

Plana, M., et al., "Immunological benefits of antiretroviral therapy in very early stages of asymptomatic chronic HIV-1 infection," *AIDS* 14(13):1921-1933 (2000).

Porto, J.D., et al., "A Soluble Divalent Class I Major Histocompatibility Complex Molecule Inhibits Alloreactive T Cells at Nanomolar Concentrations," *Proc. Natl. Acad. Sci. USA* 90(14):6671-6675 (Jul. 1993).

Ravot, E., et al., "New Uses for Old Drugs in HIV Infection," *Drugs* 58(6):953-963 (Dec. 1999).

Salazar-Gonzalez, J.F., et al., "Relationship of plasma HIV-RNA levels and levels of TNF-α and immune activation products in HIV infection," *Clin. Immunol. Immunopathol.* 84(1):36-45 (Jul. 1997).

Stagsted, J., et al., "Regulation of Insulin Receptor Functions by a Peptide Derived from a Major Histocompatibility Complex Class I Antigen," *Cell* 62(2):297-307 (1990).

Yasri, A., et al., "Rational choice of molecular dynamics simulation parameters through the use of the three-dimensional autocorrelation method: application to calmodulin flexibility study," *Protein Eng.* 9(11):959-976 (Nov. 1996).

Zhang, Z.-Q., et al., "Kinetics of CD4+ cell repopulation of lymphoid tissues after treatment of HIV-1 infection," *Proc. Natl. Acad. Sci. USA* 95(3):1154-1159 (Feb. 1998).

Heveker, N., et al., "Pharmacological properties of peptides derived from stormal cell-derived factor 1: Study on human polymorphonuclear cells," *Mol. Pharmacol.* 59(6):1418-1425 (Jun. 2001).

Raychaudhuri, S., et al., "Immunomodulatory effects of peptide T on Th 1/Th 2 cytokines," *Int. J. Immunopharmacol.* 21(9):609-615 (Sep. 1999) (first published online Aug. 11, 1999).

\* cited by examiner

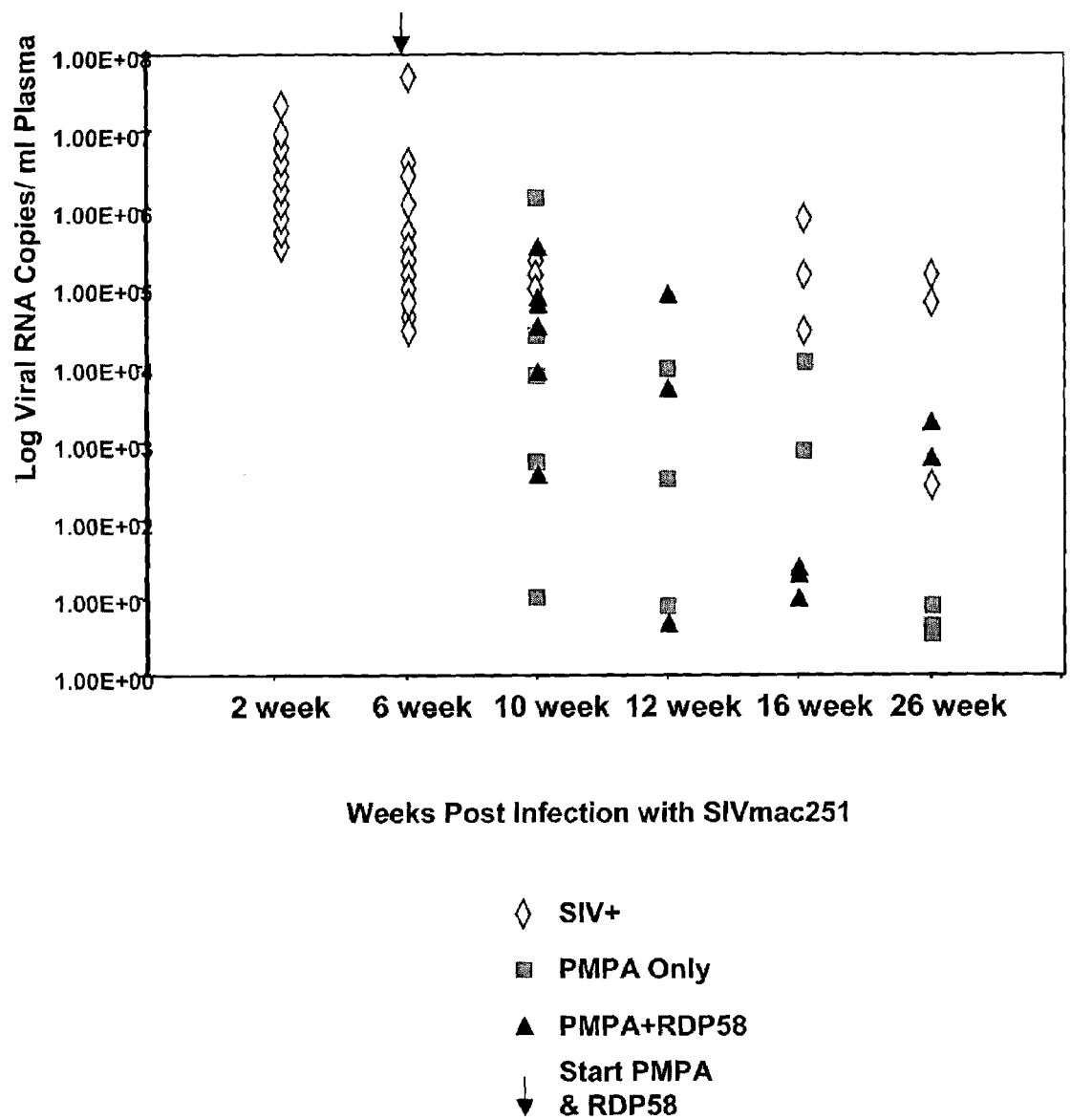
FIG_3

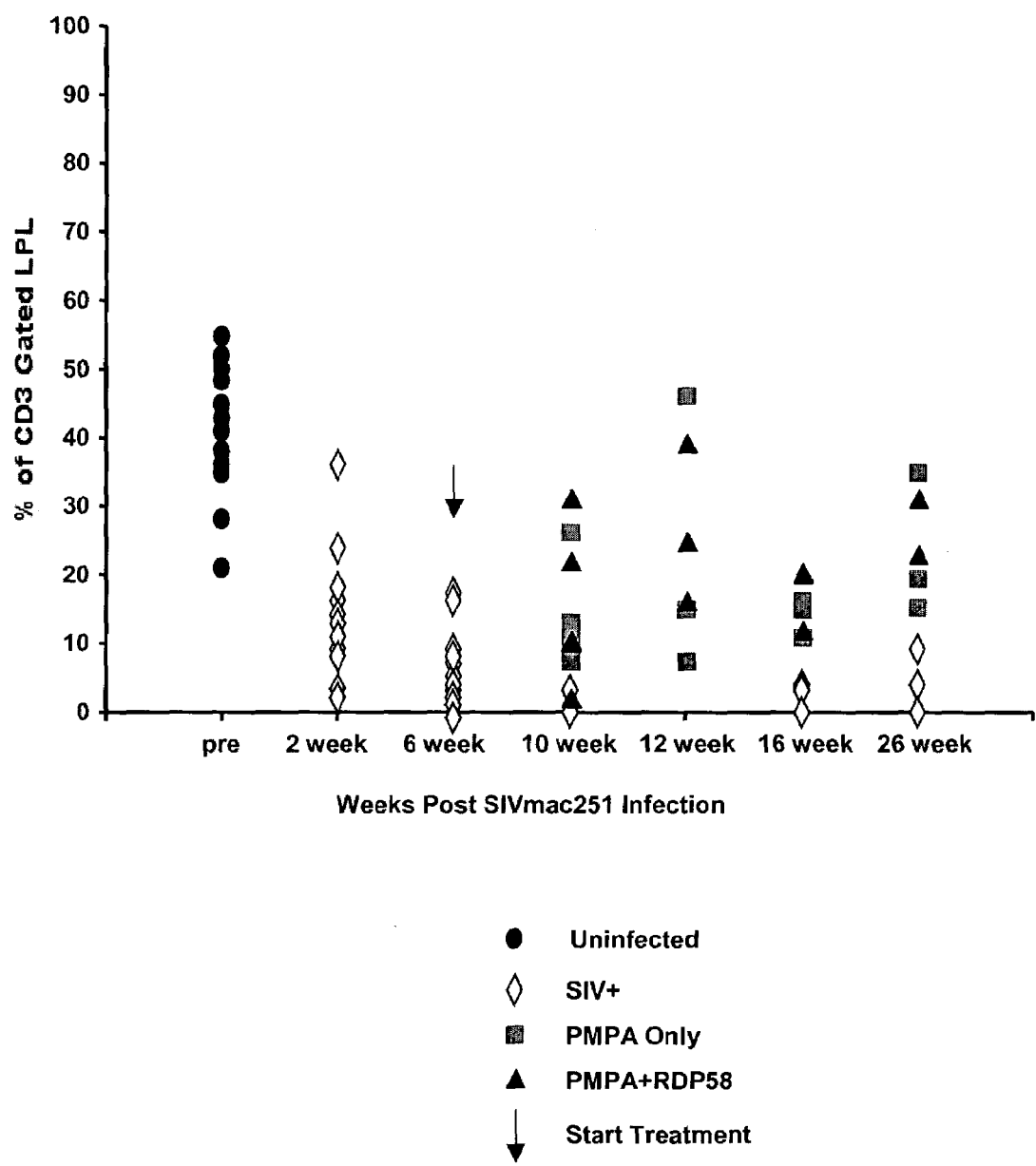
FIG_4A

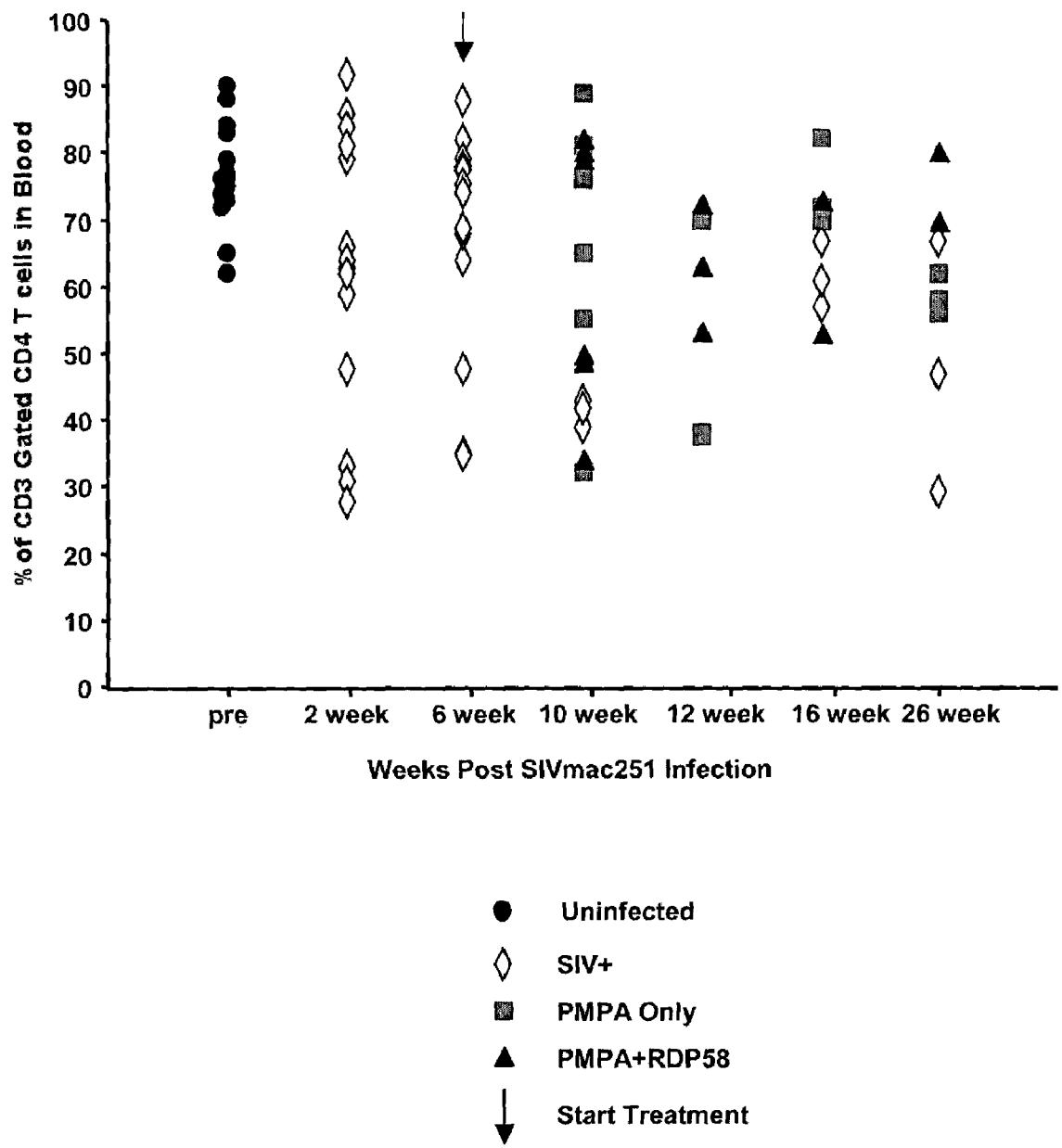
FIG_4B

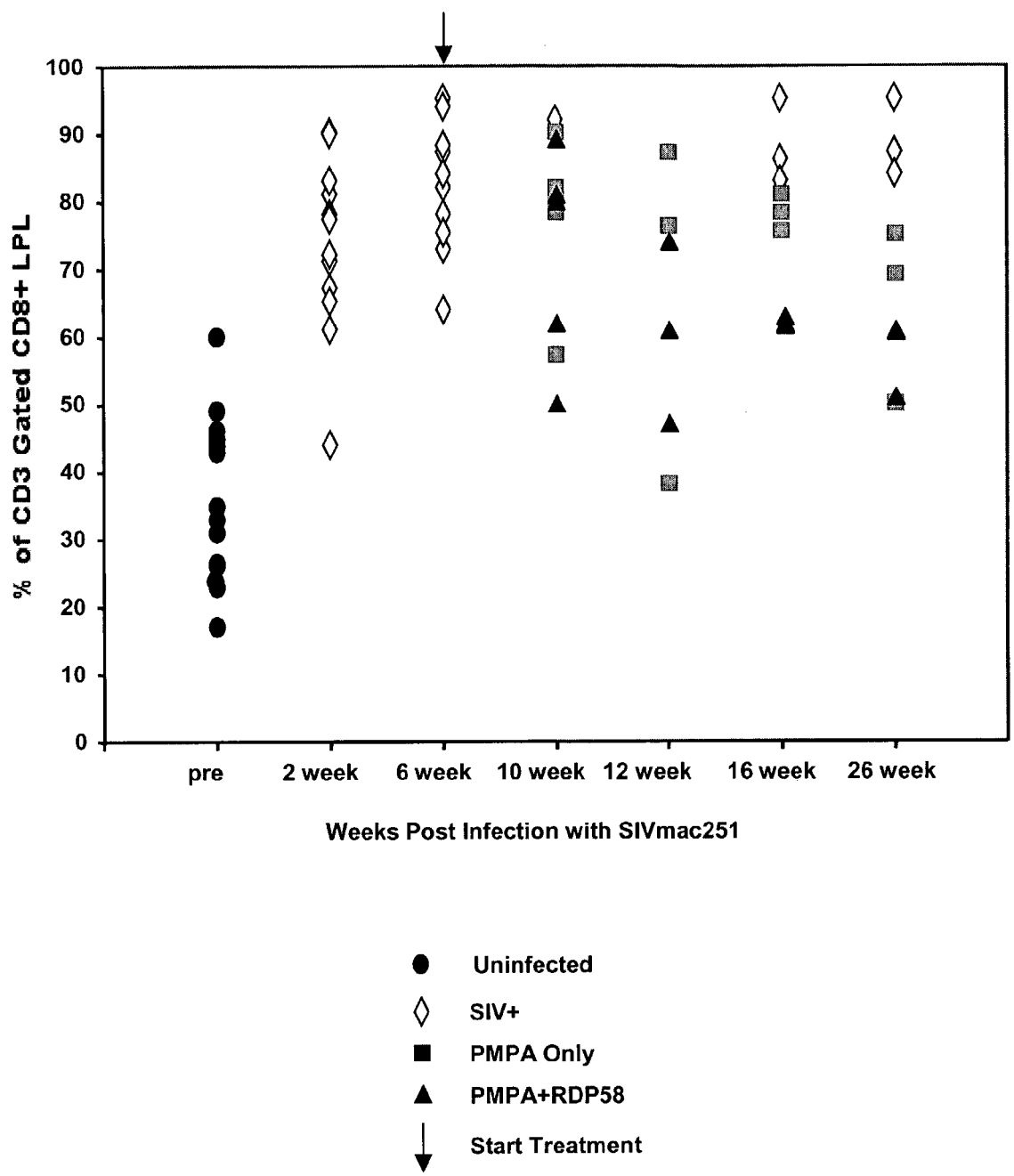
FIG_5A

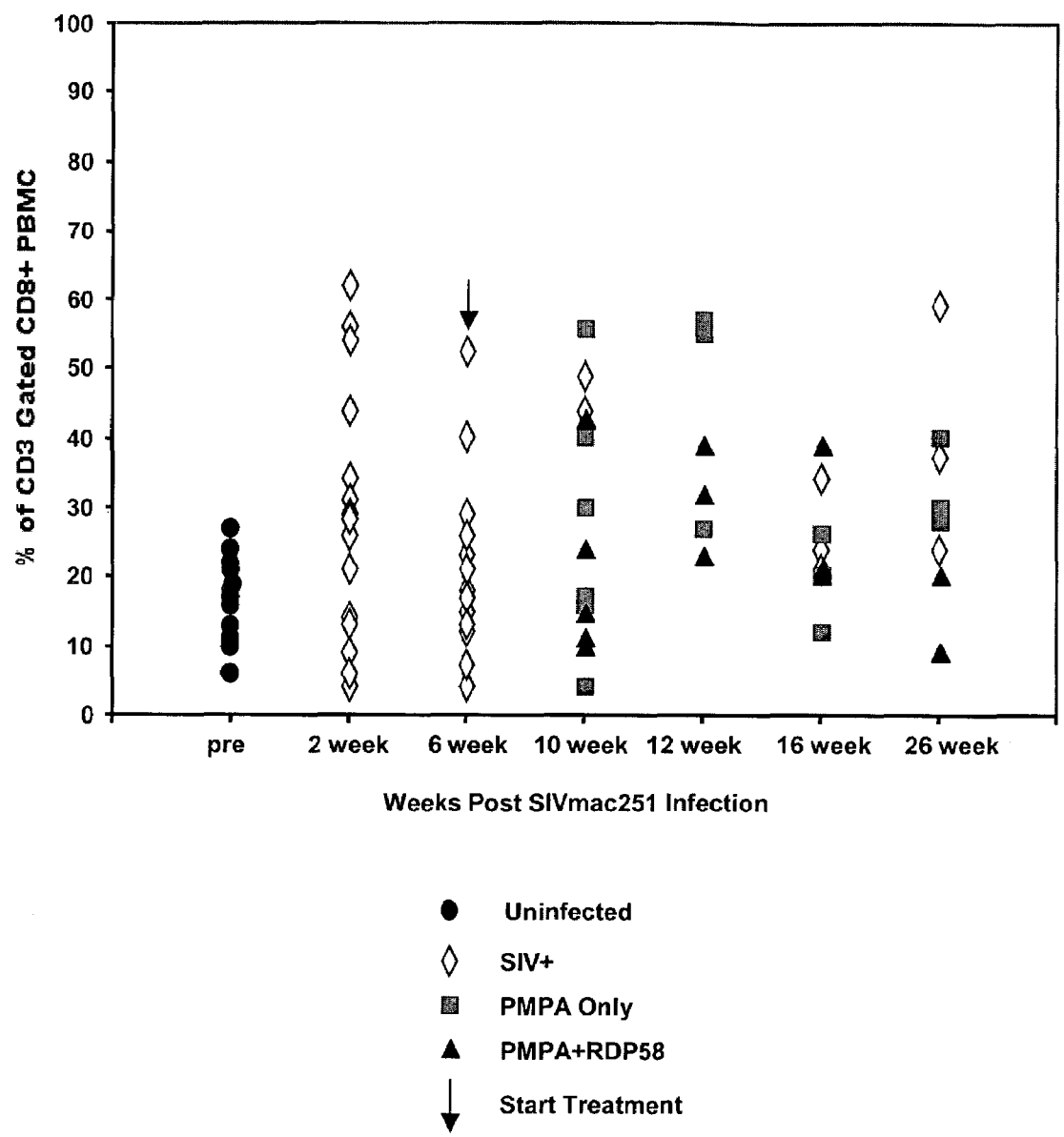
FIG_5B

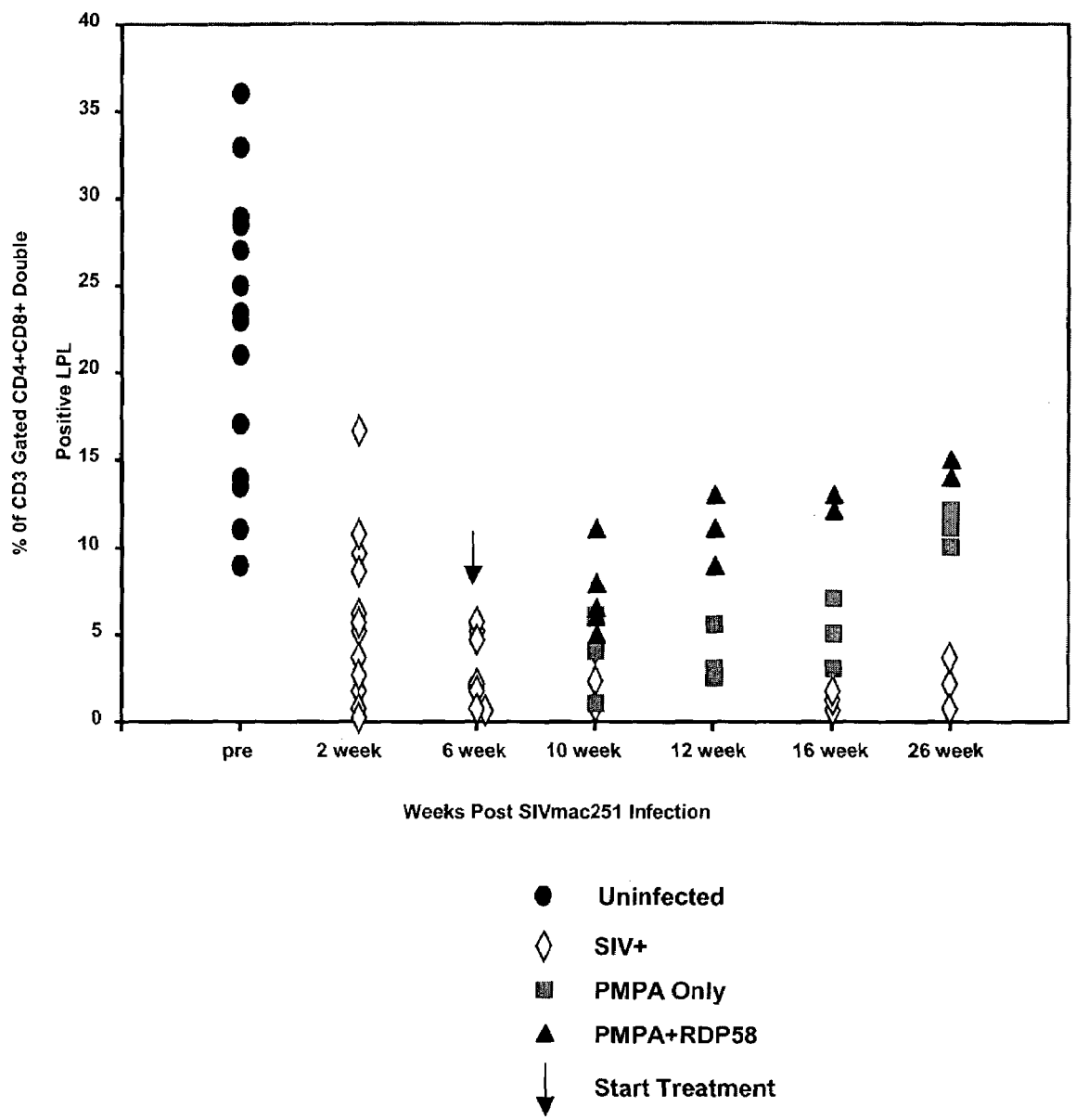
FIG_6A

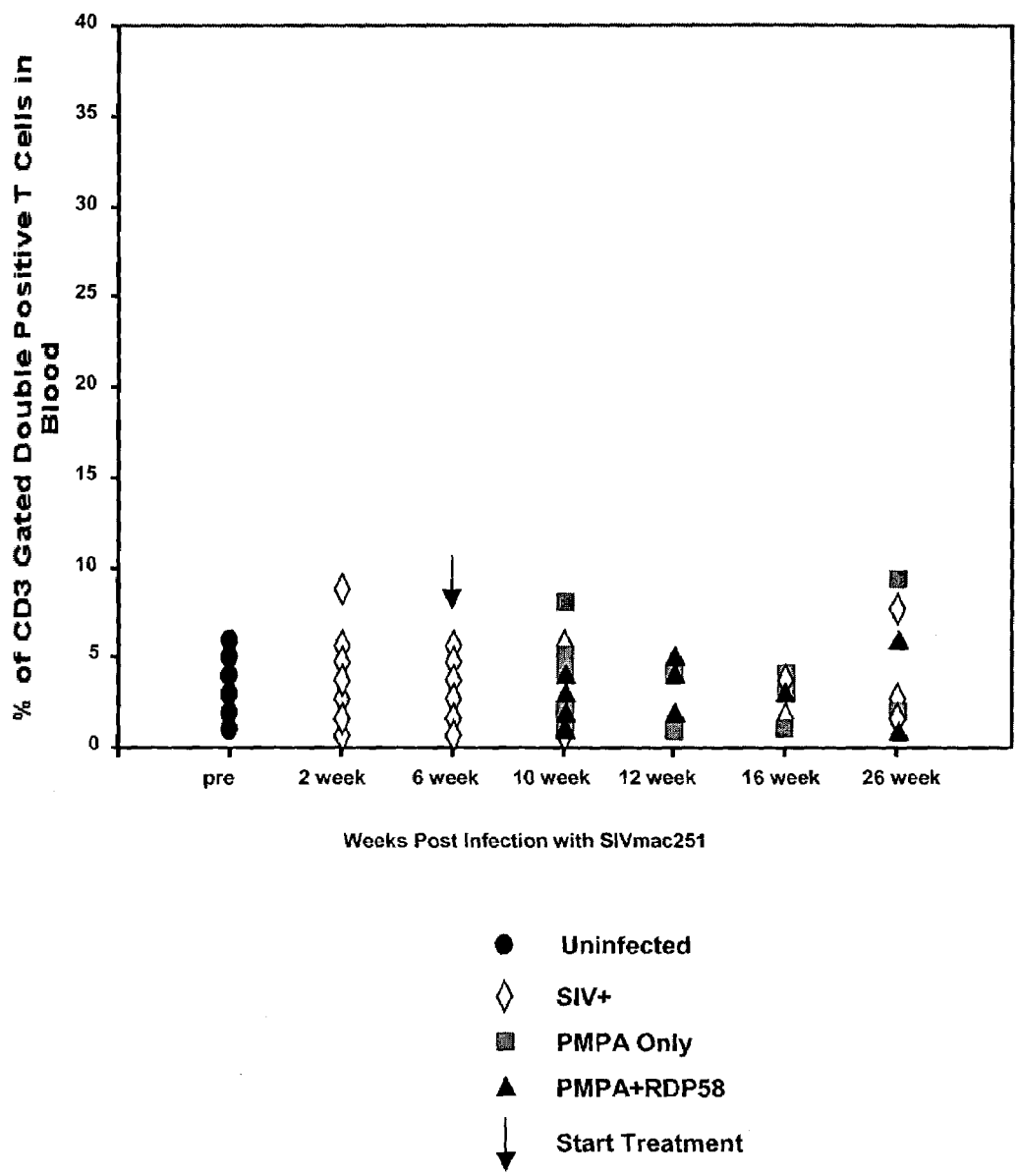
FIG_6B

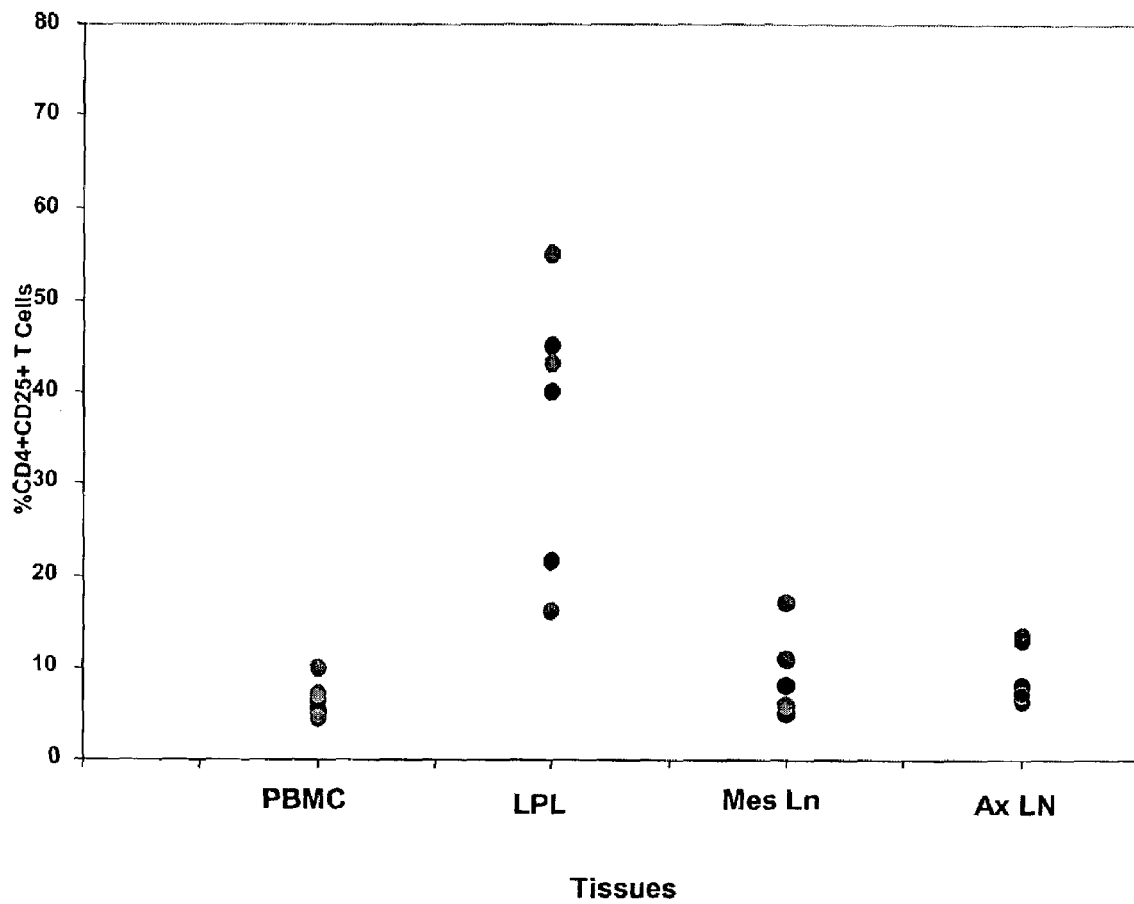
FIG_7A

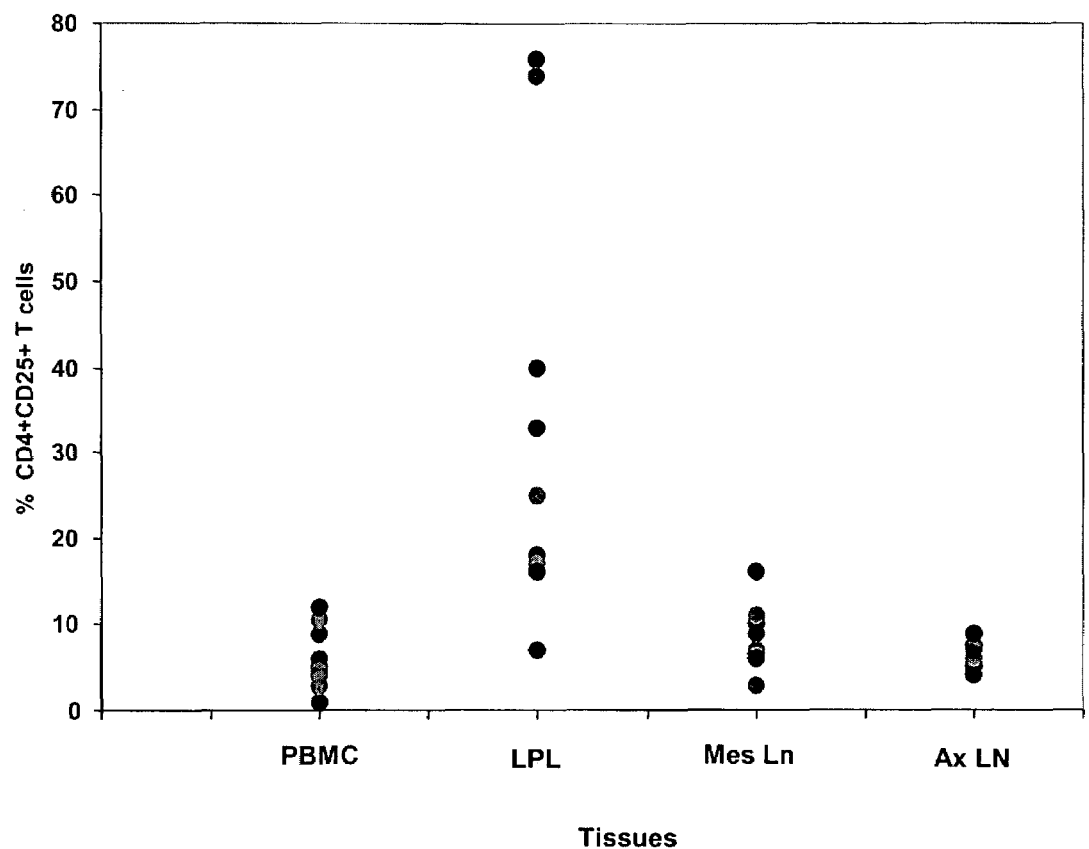
FIG_7B

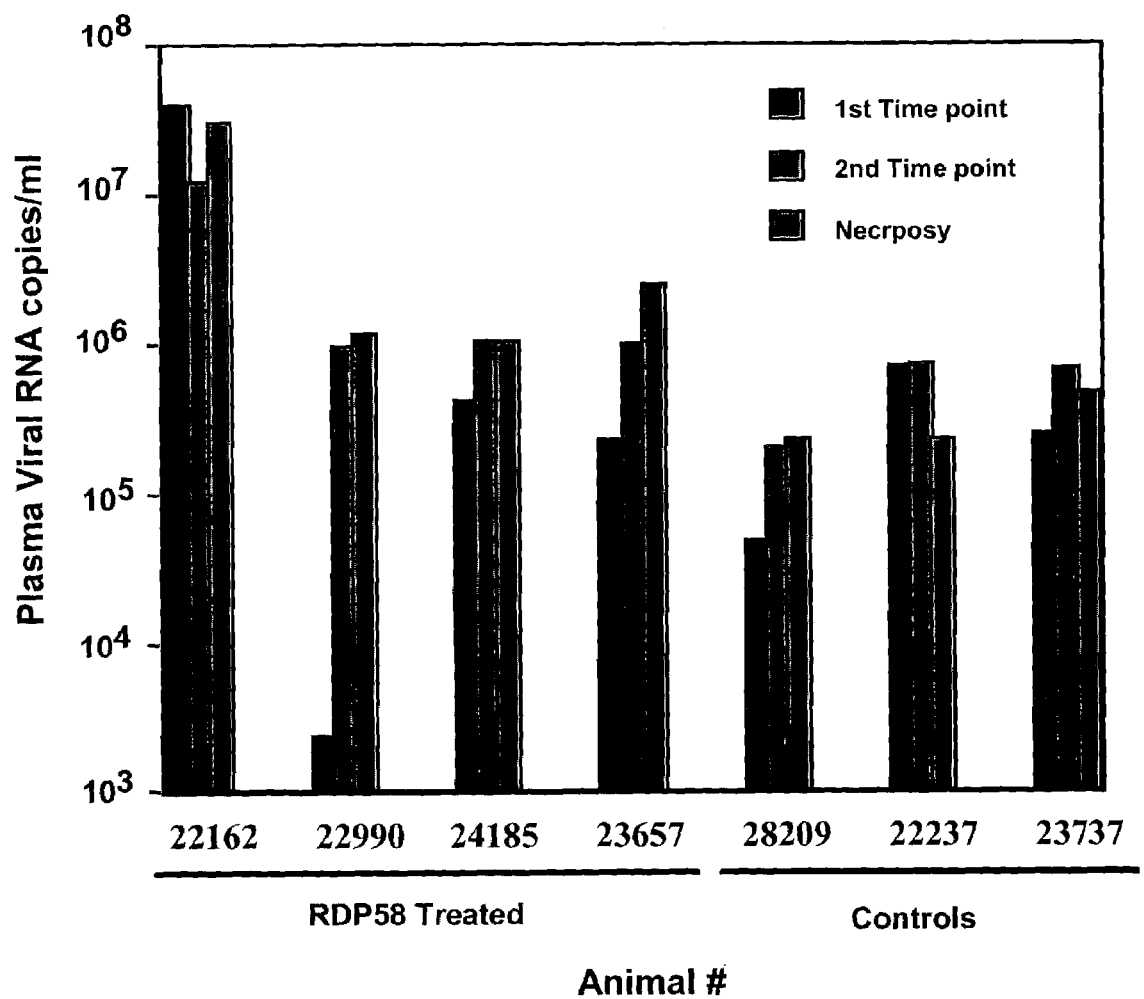
FIG_8

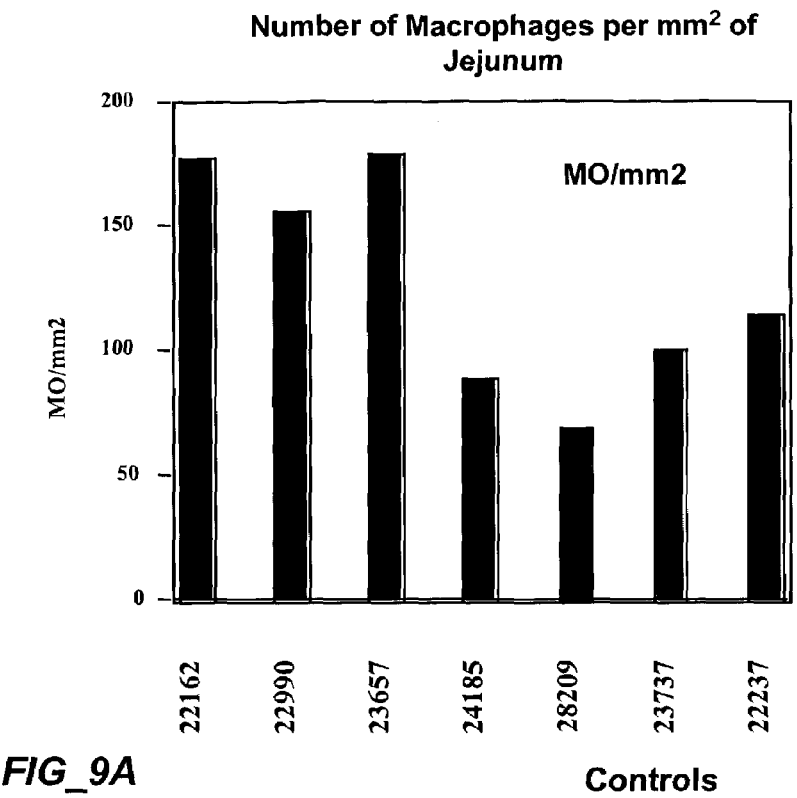
FIG_9A
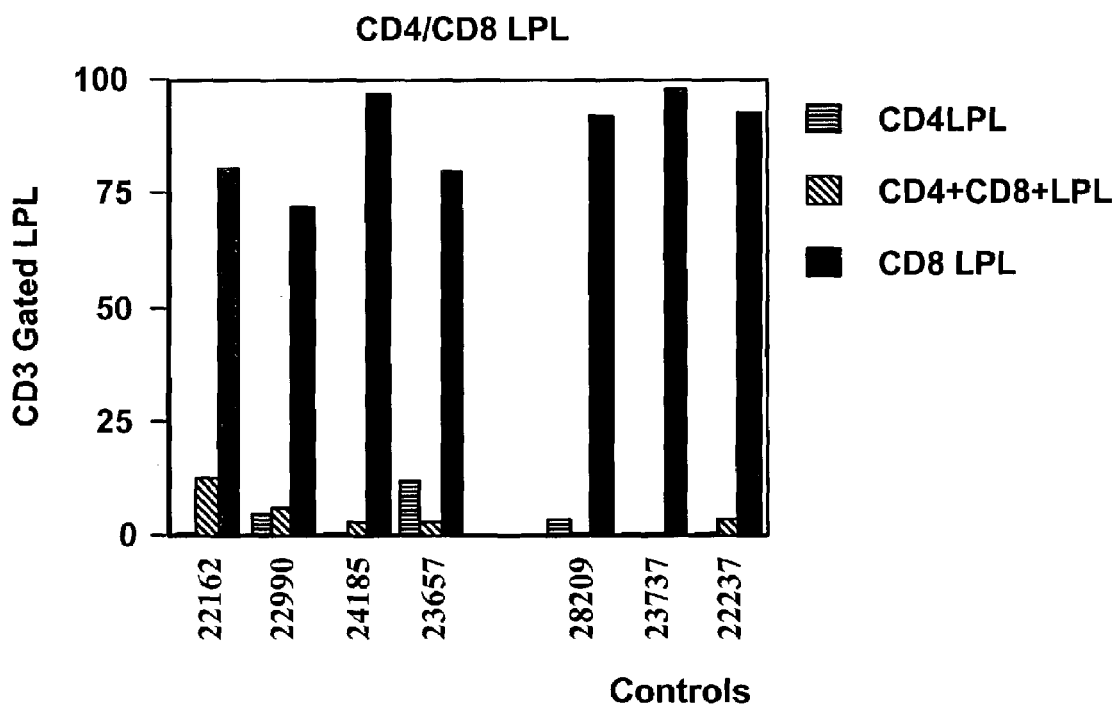
FIG_9B

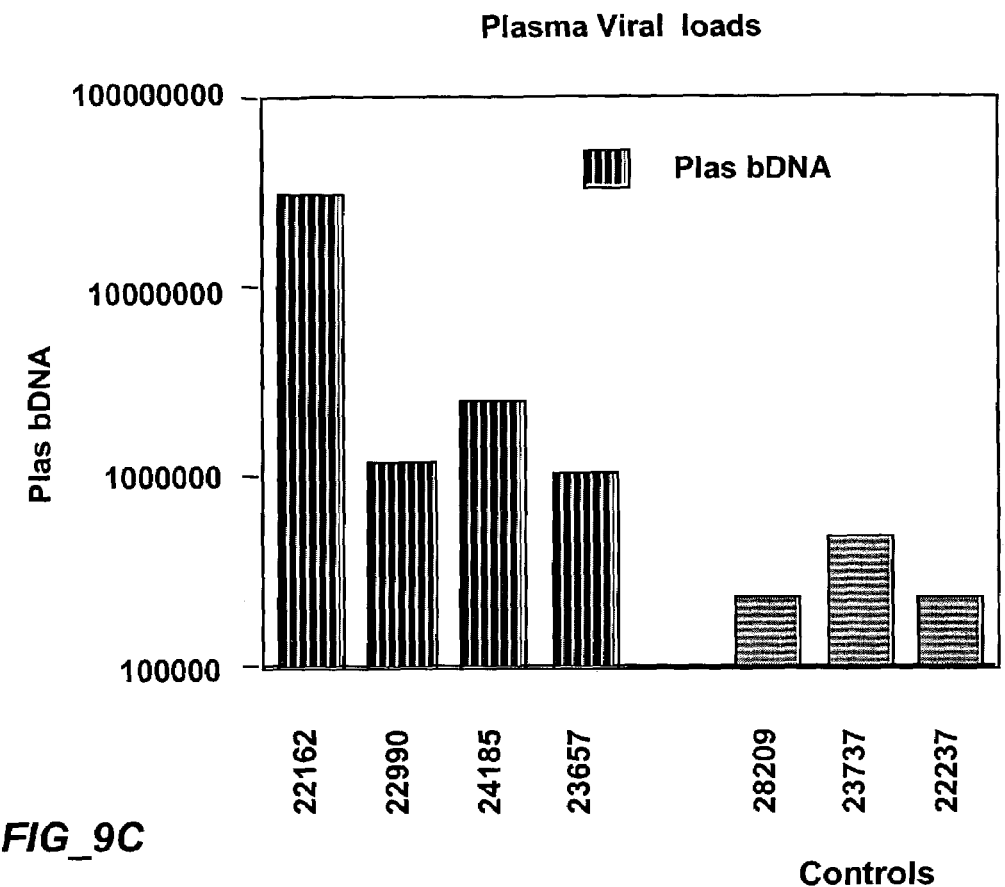
FIG_9C
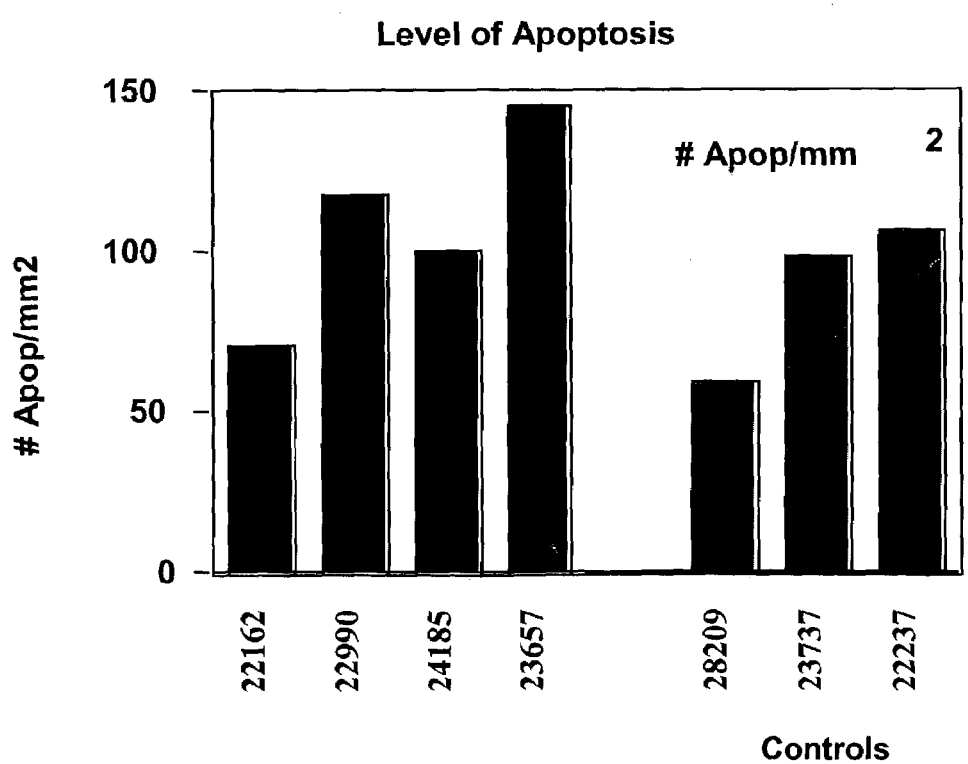
FIG_9D

COMBINED THERAPY FOR TREATMENT OF HIV INFECTION

CROSS-REFERENCE TO RELATED APPLICATIONS

This application claims benefit of U.S. Provisional Patent Application No. 60/351,925 filed Jan. 24, 2002, the entire contents of which is incorporated herein by reference.

FIELD OF THE INVENTION

The present invention relates to pharmaceutical preparations and methods for treating HIV and AIDS, and in particular, to novel combinations of immunomodulatory peptides and anti-retroviral agents.

BACKGROUND OF THE INVENTION

Human immunodeficiency virus type 1 (HIV-1) infection is characterized as a systemic immunosuppressive disorder caused by the viral-mediated depletion of $CD4^+$ T cells, which develops into the profound immunodeficiency that underlies AIDS. The targeting of $CD4^+$ lymphocytes by HIV-1 is thought to result from expression of cell surface CD4 (Dalgleish et al., Nature 312:763–767 (1984)), the chemokine receptor CXCR4 (Feng et al., Science 272: 872–877 (1996)) and (upon activation) CCR5 (Alkhatib et al., Science 272:1955–58 (1996)), which act as receptors for the attachment and entry of HIV-1 (Imlach et al., J. Virol. 75(23):11555–11564 (2001)). HIV infection may also result in a particularly massive reduction in the double-positive $CD4^+$ $CD8^+$ T cell population, possibly due to reduced expression of Bcl-2 and concomitant sensitivity to apoptosis (Guillemard et al., Blood 98(7):2166–2174 (2001)). CD4 and CCR5 are also thought to be responsible for HIV infection of macrophages and macrophage-derived cell types in vivo, although the effect this has on the immune system is unresolved (Guillemard et al., supra). The severe immunodeficiency caused by HIV infection is due not only to the low $CD4^+$ T cell numbers but also to the qualitative dysfunction of the lymphocytes (Bogner et al., Infection 29:32–36 (2001)).

The progression of HIV-1 infection is clearly associated with an increase in the viral load in plasma as well as the progressive depletion of $CD4^+$ T cells. Treatment of HIV-1-infected individuals with potent combinations of anti-retroviral drugs can result in a dramatic decline of the viral load to undetectable HIV-1 RNA levels in the majority of patients (Pakker et al., Nat. Med. 4(2):208–14 (1998)). Apart from controlling viral replication, however, the major goal of these antiviral therapies is to achieve a degree of immune reconstitution. Although increases in $CD4^+$ T cell numbers have been observed, the mechanisms underlying T cell repopulation and restoration of function are still unclear, and complete quantitative or qualitative reconstitution of the immune system may not be achieved or may take a long time to be achieved (Pakker et al., supra). The renewal proceeds slowly, suggesting, in some cases, a severe impairment of T-cell progenitors, depending on the stage of the disease and the age of the patient (Chene et al., J. Virol. 73:7533–7542 (1999)). In many cases, recovery of immune functions to almost normal levels has not been achieved (Plana et al., AIDS 14(13):1921–1933 (2000); Hejdeman et al., AIDS Res. Hum. Retro. 17:277–286 (2001)).

The clinical abnormalities correlated with the presence of HIV infection include immune suppression as well as morphologic and histopathologic changes in intestinal mucosa. Pathologic changes in small intestinal tissues from HIV-infected patients include crypt hyperplasia, villus atrophy, and inflammation. Functional changes have included decreased digestive enzyme activities (Heise et al., Gastroenterology 100(6):1521–1527 (1991); Ullrich et al. Ann Intern Med 111 (1):15–21 (1989)) and intestinal permeability (Keating, J. et al., Gut 37(5):623–629 (1995)), indicative of abnormalities in absorptive epithelial cells. Aberrant mucosal antibody responses and compromised epithelial barrier function may contribute to intestinal disease in HIV infection (Janoff et al., J. Infect. Dis. 170(2):299–307 (1994)).

Gastrointestinal complications commonly seen in HIV-infected patients are nutrient malabsorption, malnutrition, diarrhea and weight loss. These symptoms are associated with a rapid clinical course (Ehrenpreis et al., J. Acquir. Immune Defic. Syndr. 5(10):1047–1050 (1992); Ehrenpreis et al., Am J Clin. Pathol. 97(1):21–28 (1992). With the onset of immunodeficiency, opportunistic enteric pathogens contribute to the severity of intestinal disease (Smith et al., Gastroenterol Clin. North Am. 17(3):587–598 (1988); Kotler, D. P. et al., Ann. Intern. Med. 113(6):444–449 Greenson et al., Ann. Intern. Med. 114(5):366–72 (1991)). However, in many instances, intestinal abnormalities are often detected prior to advanced stages of immunodeficiency and in the absence of detectable enteric pathogens (Gillin et al., Ann. Intern. Med. 102(5):619–622 (1985); Heise et al., supra; Ullrich et al., supra; Kotler et al., supra; Greenson et al., supra; and Miller, A. R. et al., Q J Med. 69(260):1009–1019 (1988). Thus the onset of the intestinal mucosal immune system dysregulation may occur early in infection.

The role of tumor necrosis factor (TNF) in gastrointestinal inflammation in HIV infected individuals is unclear. In SIV-infected rhesus monkeys, expression of TNF is known to be variable throughout the disease course; significant levels were present in intestinal mucosa of 5 of 7 asymptomatic animals, and 6 of 8 terminal animals. It was undetectable in the majority of animals in the acute stage of infection, regardless of viral inoculum. A reciprocal relationship was observed between TNF and IL-10. This suggests that the presence of IL-10 in the intestinal mucosa inhibits TNF production by resident macrophages, as has been described previously in other systems (Fiorentino, et al., J. Immunol. 147(11):3815–3822 (1991); de Waal Malefyt et al., J. Exp. Med. 174(5):1209–1220 (1991)).

TNF is also known to increase HIV replication in various monocyte and T cell model systems (Chene et al., J. Virol. 73(9):7533–7542 (1999); Marshall et al., J. Immunol. 162 (10):6016(1999); Heguy et al., Antivir. Chem. Chemother. 9(2):149–155 (1998); Munoz-Fernandez et al., J. Allergy Clin. Immunol. 100:838–845 (1997)). Addition of neutralizing anti-TNF antibodies to primary cultures of HIV-infected human T lymphocytes drastically reduces p24 antigen release and prevents $CD4^+$ cell depletion associated with infection (Munoz-Fernandez et al., supra). Anti-TNF also prevents nuclear factor-kappa B activation, which is involved in the activation of HIV replication. On the other hand recent reports suggest that TNF suppresses HIV replication in freshly infected peripheral blood monocytes and alveolar macrophages (Herbein et al., J. Virol. 70(11):7388–7397 (1996)). Additional studies with a large number of patients will be necessary to evaluate the effect of anti-TNF antibody therapy on disease progression.

As indicated above, significant challenges still remain in the scientific and clinical battle against HIV and AIDS. What is needed are improved compositions and methods capable of accelerating and enhancing the immune reconstitution of infected individuals, and effectively treating gastrointestinal complications resulting from HIV infection.

Relevant Literature

Buelow et al., *Transplantation* 59:649–654 (1995) and references cited therein. Manolios et al., *Nature Medicine* 3:84–88 (1997) describes oligopeptides derived by rational design which modulate T cell activity. WO 95/13288 by Clayberger et al. which describes peptides capable of modulating T cell activity. References describing methods for designing compounds by computer using structure activity relationships include Grassy et al., *J. of Molecular Graphics* 13:356–367 (1995); Haiech et al., *J. of Molecular Graphics* 13:46–48 (1995); Yasri et al., *Protein Engineering* 11: 959–976 (1996); Ashton et al., *Drug Discovery Today* 1:71–78 (1996); and Iyer et al., *Curr. Pharm. Des.* 8:2217–2229 (2002)

SUMMARY OF THE INVENTION

The present invention relates to pharmaceutical preparations and methods for treating HIV infection and the resultant Acquired Immune Deficiency Disorder, or AIDS. In particular, novel combinations of immunomodulatory peptides and anti-retroviral agents are provided to accelerate and enhance immune reconstitution and normalization in gut-associated lymphoid tissue (GALT), and to alleviate the gastrointestinal abnormalities and dysfunction resulting from HIV infection. As described herein, the synergistic combination of the subject immunomodulatory peptides with anti-retroviral therapies accelerates and enhances CD4+ T cell repopulation in GALT well beyond that obtained using anti-retroviral therapies alone, and further results in a dramatic increase in double-positive CD4+CD8+ T cells in GALT. Thus, methods are provided utilizing the combination therapies described herein to increase the level of single-positive CD4+ T cells and/or double-positive CD4+ CD8+ T cells in GALT of individuals infected with HIV, along with kits for carrying out the subject methods.

Suitable immunomodulatory peptides for use in the subject compositions and methods are capable of modulating the activity of various immune system cells, particularly T cells, and/or inhibiting the production of inflammatory cytokines. In a preferred embodiment, the subject peptides comprise one or more of the cytomodulating peptides disclosed in co-pending U.S. patent applications U.S. Ser. No. 09/028,083 & U.S. Ser. No. 08/838,918 as well as corresponding International Publication WO 98/46633, the disclosures of which are expressly incorporated herein by reference. In a particularly preferred embodiment, the immunomodulating peptide comprises the sequence Arg-nL-nL-nL-Arg-nL-nL-nL-Gly-Tyr (SEQ ID NO:1), where nL is norleucine and all amino acids are the D-stereoisomer.

In one aspect, the peptides have amino acid extensions at the N- or C-terminus to provide additional functionality, such as targeting the peptide to the affected tissue, increasing half-life, or for attachment of various compounds. In another aspect, the cytomodulating peptides are oligomers, particularly dimers of the active sequence, or are in the form of cyclic peptides. The peptides may comprise naturally-occurring amino acids or, more preferably, one or more D-stereoisomers.

Suitable anti-retroviral agents for use in the therapeutic compositions and methods described herein include nucleoside reverse transcriptase inhibitors, non-nucleoside reverse transcriptase inhibitors, protease inhibitors, co-receptor antagonists, retroviral integrase inhibitors, viral adsorption inhibitors, viral specific transcription inhibitors, and cyclin dependent kinase inhibitors.

In one embodiment, a pharmaceutical preparation is provided comprising a novel combination of an immunomodulating peptide and an anti-retroviral agent for simultaneous or sequential administration to a patient infected with HIV-1. In a preferred embodiment, the anti-retroviral agent is a nucleoside reverse transcriptase inhibitor selected from the group consisting of Azidothymidine, Lamivudine, Didanosine, Zalcitabine, Stavudine, Abacavir, and Tenofovir. In another preferred embodiment, the anti-retroviral agent is a non-nucleoside reverse transcriptase inhibitor selected from the group consisting of Nevirapine, Dlavirdine, and Efavirenz. In yet another preferred embodiment, the anti-retroviral agent is a protease inhibitor selected from the group consisting of Indinavir, Saquinavir, Ritonavir, Nelfinavir, Amprenavir, and Lopinavir.

In another preferred embodiment, combinations of a plurality of antiviral agents may be used, thus increasing the efficacy of the therapy and lessening the occurrence of resistance to the anti-viral drugs. Various combinations may be made and used by those skilled in the art. In one aspect, the immunomodulatory peptides, particularly a peptide comprising sequence Arg-nL-nL-nL-Arg-nL-nL-nL-Gly-Tyr (SEQ ID NO:1), wherein all the amino acids are D-stereoisomers is used with a combination of retroviral agents comprising a reverse transcriptase inhibitor and a protease inhibitor. In another aspect, the combination of antiviral agents comprises different protease inhibitors or different reverse transcriptase inhibitors.

In the present invention, a method for treating a patient infected with HIV-1 is provided, comprising the administration of a therapeutically effective amount of an immunomodulatory peptide, either alone or in combination with one or more anti-retroviral agent(s). When used in combination with an anti-retroviral agent, the immunomodulatory peptide may be administered simultaneously or sequentially with the anti-retroviral agent. In a preferred embodiment, the dose is effective to increase the number of single-positive CD4$^+$ T cells in GALT of said patient. In another preferred embodiment, the dose is effective to increase the number of double-positive CD4$^+$ CD8$^+$ T cells in GALT of said patient. In a further and preferred embodiment, said dose is also effective to alleviate gastrointestinal abnormalities associated with HIV infection.

Generally, the pharmaceutical preparations and methods disclosed herein accelerate the process of immune reconstitution in GALT of HIV-infected individuals and enhance the level of immune reconstitution achieved, resulting in a more normalized T cell population in GALT. Thus, the present invention further contemplates general methods for enhancing or improving immune reconstitution in individuals suffering from T cell depletion such as, e.g., the CD4$^+$ T cell depletion caused by HIV infection, as well as general methods for normalizing T cell populations in tissues affected by such depletion.

BRIEF DESCRIPTION OF THE DRAWINGS

FIG. 3 shows suppression of plasma viral loads in phosphonate 9-R-(2-phosphonomethoxypropyl)adenine (PMPA)

Figure 1:
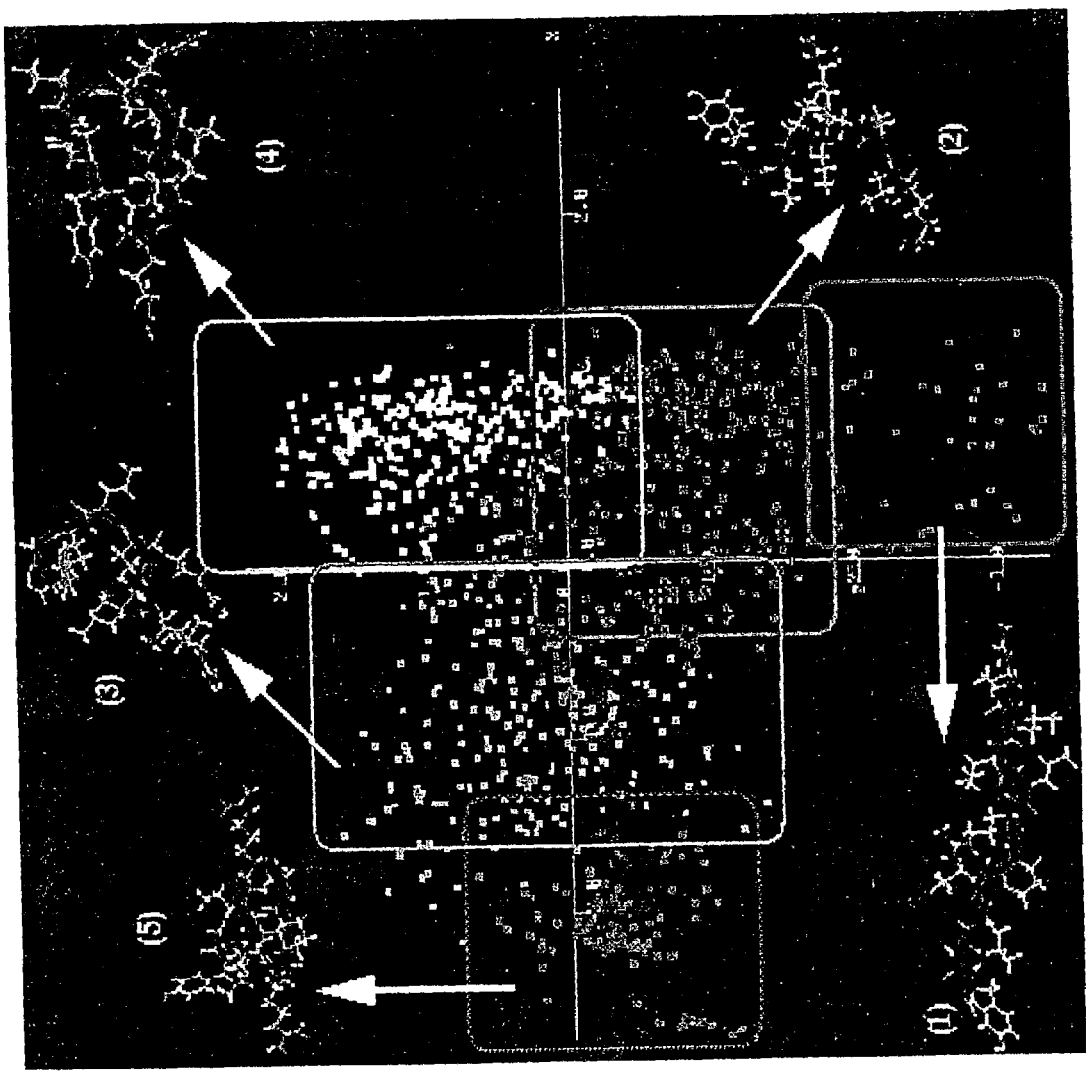
FIG. 1 is a depiction of the conformational space clustering of the bc 1nL peptide. The conformations drawn are obtained from cluster analysis of bc 1nL trajectory.

and bc 1nL peptide (also denoted as "RDP58") treated SIV-infected Rhesus macaques. All animals infected with SIV showed high titers of virus in plasma at 2 weeks post infection. Viral loads measured as viral RNA copies/ml plasma remained high at week 6 at which time PMPA+/− RDP58 therapy was initiated. PMPA treatment resulted in a gradual decrease in viral load in all treated animals regardless of whether they were treated with RDP58 or not. This indicated that RDP58 did not interfere with or change the effect of antiretroviral therapy in these animals. Noticeably, at week 16, animals that had received RDP58 in addition to PMPA had lower titers than those treated with PMPA alone. This difference, however, was less significant at week 26.

FIG. 4A shows levels of CD3 gated $CD4^+$ T-cells in the intestinal mucosa while FIG. 4B shows levels of $CD4^+$ T cells in the blood. All SIV infected animals showed immediate and severe depletion in CD3 gated $CD4^+$ T cells in gut associated lymphoid tissue (GALT). Although $CD4^+$ cells were depleted in peripheral tissue, this depletion was not as severe as that in GALT. As expected, the $CD4^+$ numbers remained low in untreated animals through week 26 of the study. Treatment with PMPA or PMPA+RDP58 resulted in a reversal of $CD4^+$ T cells. However, the PMPA+RDP58 treated animals tended to show a more consistent rebound in $CD4^+$ T cells in peripheral tissue as well as GALT compared to PMPA treatment alone.

FIG. 5A shows levels of CD3 gated $CD8^+$ T-cells in the intestinal mucosa while FIG. 5B shows levels of $CD8^+$ T-cells in the blood. All SIV infected animals showed an immediate increase in the % CD3 gated $CD8^+$ cell population, in GALT as well as peripheral tissue. However, the increase in % $CD8^+$ cells was more striking and consistent in GALT than in peripheral tissue. This apparent increase is primarily due to a severe depletion in $CD4^+$ cells. Animals treated with PMPA alone or PMPA+RDP58 showed a gradual decrease in % $CD8^+$ cells by week 10, while untreated animals showed no change. At weeks 16 and 26, however, the PMPA+RDP58 treated animals demonstrated a lower % $CD8^+$ counts in GALT indicating that the $CD4^+$/$CD8^+$ ratio tended towards normal proportions. Therapeutic effects were less apparent in peripheral tissue.

FIG. 6A shows CD3 gated $CD4^+CD8^+$ double positive T cells in the mucosa while FIG. 6B shows levels of double positive cells in the blood. SIV infection resulted in a dramatic decrease in $CD4^+CD8^+$ T cells in GALT. There was no apparent change in $CD4^+CD8^+$ T cell numbers in blood at any time point. Untreated animals had consistently low levels in GALT throughout the study. PMPA treatment resulted in modest changes in $CD4^+CD8^+$ T cell counts in GALT by week 12. PMPA+RDP58 treatment, however, resulted in a striking rebound of $CD4^+CD8^+$ T cell numbers at week 12 that remained high at week 16 and week 26. This increase was seen in all animals treated with PMPA+RDP58.

FIG. 7A shows levels of CD4 gated IL-2 receptor positive T-cells at 12 weeks necropsy. FIG. 7B are the levels of IL-2 positive T-cells at 26 week necropsy. The presence of IL-2 receptor positive T-cells is an indication of proliferating cells.

FIG. 8 shows effect of RDP58 treatment on plasma viral loads in SIV infected animals at various times during treatment with RDP58. Viral loads were examined at 12 weeks (first time point); and 26 weeks (second time point); and at necropsy.

FIGS. 9A–9D shows effect of RDP58 treatment of various measured parameters. FIG. 9A gives the number of macrophages present in the jejunum. Presence of CD4/CD8 double positive cells are given in FIG. 9B. Level of apoptosis is given in FIG. 9C and plasma viral load in shown in FIG. 9D.

DETAILED DESCRIPTION OF THE INVENTION

Methods and compositions are provided for treating patients infected with HIV, and more particularly, for accelerating and enhancing immune reconstitution and alleviating intestinal dysfunction in such patients. Immunomodulatory peptides are used either alone or, more preferably, in synergistic combinations with anti-retroviral agents to rapidly increase T cell repopulation in gut-associated lymphoid tissue (GALT) of infected individuals. In contrast to the prior art, dramatic improvements in the repopulation of both single-positive $CD4^+$ and double-positive $CD4^+$ $CD8^+$ T cells in intestinal lymphoid tissue are obtained using the compositions and methods described herein.

The compositions and methods disclosed herein resolve the shortcomings of current HIV therapies by dramatically accelerating the pace of immune reconstitution in treated patients and by enhancing and increasing the numbers of both single-positive $CD4^+$ and double-positive $CD4^+$ $CD8^+$ T cells in the GALT of such patients to more normal levels. The rapid and sustainable restoration of normalized T cell populations in GALT of HIV patients is an important goal in the treatment of HIV infection and is made possible using the methods and compositions described herein. Moreover, the enhanced restoration of double-positive $CD4^+$ $CD8^+$ T cells achieved with the present invention is of particular significance, since this may indicate a significant improvement in the reconstitution of the T cell progenitor population leading to a more balanced and stable T cell repopulation. Moreover, such double-positive cells have recently been implicated as having a potential role in suppression of viral replication, adding further interest and urgency to their rapid repopulation in infected patients (see, e.g., Holznagel et al., *J. Gen Virol.* 83:631–40 (2002)).

Thus, the present invention provides novel pharmaceutical preparations comprising an immunomodulatory peptide and at least one anti-retroviral agent for simultaneous or sequential administration to a patient infected with HIV. As disclosed herein, the administration of such immunomodulatory peptides and anti-retroviral agents in combination therapies accelerates and enhances immune reconstitution in GALT of infected HIV patients. In particular, methods for accelerating the process of T cell reconstitution and/or for enhancing or increasing the restoration of single-positive $CD4^+$ as well as double-positive $CD4^+$ $CD8^+$ cells are provided herein, as are methods for achieving normalized T cell populations in GALT of HIV patients.

As described herein, administration of the subject peptides in combination with anti-retroviral agents results in a synergistic effect on immune reconstitution. Without being bound by theory, it is possible that the anti-inflammatory activity of the subject peptides contributes to stabilization of the intestinal mucosa such that T cell repopulation can be accelerated and enhanced. Administration of the subject peptides also alleviates the intestinal dysfunction experienced by patients suffering from AIDS. Reducing or alleviating gastrointestinal dysfunction in the context of HIV infection and AIDS includes as non-limiting examples, reduction in clinical manifestations such as diarrhea, rectal bleeding, malabsorption, abdominal pain, weight loss, fever, anemia, fecal occult blood, fecal leukocytes, and histological indications such as crypt abcesses, leukocyte infiltration, cell apoptosis, transmual granulamotous inflammation, superficial mucosal and submucosal inflammation, etc. Furthermore, included within the definition of symptoms as used herein are changes in levels of biochemical and molecular markers associated with intestinal inflammation arising from HIV infection, including, but not limited to, increase in pro-inflammatory cytokines (e.g., TNF-α, interferon-γ, II-1, IL-6, IL-12, etc.), changes in enzyme markers of leukocyte activation (e.g., myeloperoxidase, COX-2 expression, iNOS expression, etc.), cellular apoptosis (e.g., DNA fragmentation, caspase activation, etc.), and others known in the art. Although one marker may be used as an indication of reduction in gastrointestinal dysfunction, preferably more than one is used, and more preferably a combination of markers is used, including combinations of clinical manifestations, histological indications, and molecular/biochemical markers.

For use as treatment of patients infected with HIV, the immunomodulatory peptides may be used alone or, more preferably, in combination with other therapeutic agents, and in particular, with anti-retroviral agents. In this context, the peptides used are either a single peptide sequence, or an admixture of different peptide sequences of the present invention, or an admixture that includes natural analogs of the peptides of the present invention (e.g., B2702.75–84).

Anti-Retroviral Agents

In a preferred aspect, the immunomodulatory peptides are used in combination with anti-retroviral agents, including: (1) nucleoside reverse transcriptase inhibitors, (2) non-nucleoside reverse transcriptase Inhibitors, (3) protease inhibitors, (4) virus uptake/absoprtion inhibitors, (5) virus receptor antagonists, (6) viral fusion inhibitors, (7) viral integrase inhibitors, and (8) transcription inhibitors, and the like.

In a preferred embodiment, the anti-retroviral agents comprise reverse transcriptase inhibitors. In one aspect, the inhibitors are nucleoside/nucleotide reverse transcriptase inhibitors, which are nucleoside or nucleotide analogs that inhibit action of the viral reverse transcriptase required for conversion of the viral RNA into DNA during viral replication. These inhibitors include without limitation azidothymidine and its derivatives (e.g., AZT, Zidovudine), (2R,cis)-4-amino-1-(2-hydroxymethyl-1-1-oxathiolan-5-yl)-(1H)-pyrimidine-2-one (i.e., Lamivudine), 2',3'-dideoxyinosine (didanosine), 2',3'-dideoxycytidine (i.e., Zalcitabine), 2',3'-didehydro-3'-deoxythymidine (i.e., stavudine), (1S,cis)-4-[2-amino-6-(cyclopropylamino)-9H-purin-9-yl]-2-cyclopentene-1-methanol sulfate (i.e., abacavir), (−)-beta-2',3'-dideoxy-5-fluoro-3'-thiacytidine (i.e., emtricitabine), and phosphonate 9-R-(2-phosphonomethoxypropyl) adenine (i.e., PMPA; tenofovir disoproxil fumarate; adefovir) and various derivatives thereof (see for example, Deeks, S. G. et al., *Antimicrob. Agents Chemother.* 42(9): 2380–2384 (1998). As provided by the examples, the nucleoside/nucleotide reverse transcriptase inhibitors are generally cyclic or acyclic nucleoside or nucleotide analogs.

In another aspect, the antiviral agents comprise non-nucleoside reverse transcriptase inhibitors (NNRTI). These agents also inhibit the action of viral reverse transcriptase by binding to the enzyme and disrupting its catalytic activity. Inhibitors, include, but is not limited to, 11-cyclopropyl-5,11-dihydro-4-methyl-6H-dipyrido-[3,3-b-2',3'-][1,4]diazepin-6-one (i.e., Nevirapine); piperazine, 1-[3-[(1-methylethyl)amino]-2-pyridinyl]-4-[[5-[(methylsulfonyl)amino]-1H-indol-2-yl]carbonyl]-, monomethane sulfonate (i.e., Delavirdine); and (S)-6-chloro-4-(cyclopropylethynyl)-1,4-dihydro-4-(trifluoromethyl)-2H-3,1-benzoxazine-2-one (i.e., Efavirenz). Other include quinazolinone and it derivatives, for example trifluoromethyl-containing quinazolin-2 (1H)-ones (Corbett, J. W. et al., *Prog. Med. Chem.* 40:63–105 (2000); calanolide A (Newman, R. A. et al. *J Pharm. Sci.* 87(9):1077–1080 (1998); and 6-arylmethyl-1-(ethoxymethyl)-5-alkyluracil (i.e., emivirine) and its analogs (see El-Brollosy, N. R., *J Med. Chem.* 45(26):5721–5726 (2002)).

In a further aspect, the antiviral agents comprise protease Inhibitors. Without being bound by theory, protease inhibitors appear to inhibit HIV replication at the postintegrational level after the virus is integrated into the host chromosome. The target HIV protease enzyme, a 99-amino acid homodimer, cleaves pol-gag polypeptides on the viral envelope. The gag-pol precursor contains the amino acid sequences of various HIV proteins, such as proteins that form the capsid (p19) and nucleocapsid (p24). In addition, gag-pol also contains the sequence of retroviral enzymes, such as reverse transcriptase, proteases, and integrase. Inhibition of the HIV protease results in release of immature, noninfectious viral particles. Many of the protease inhibitors may also exert additional antiviral effects by inhibiting proteasome function in the cells. Protease inhibitors useful in the present invention include without limitation the agents indinavir, saquinavir (fortovase), ritonavir, nelfinavir, amprenavir, and lopinavir.

Virus replication may also be affected by inhibiting the action of integrase, a viral protein involved in inserting the human immunodeficiency virus type 1 (HIV-1) proviral DNA into the host genome. This class of inhibitors may comprise small molecule inhibitors or peptide inhibitors. Small molecule inhibitors, include, among others, integramycin (Singh, S. B. et al, *Org. Lett.* 4(7):1123–1126 (2002); diketo derivatives (Vandegraaff, N. et al., *Antimicrob. Agents Chemother.* 45(9):2510–2516 (2001); polyhydroxylated styrylquinolines (Zouhiri, F. et al., *J. Med. Chem.* 43(8):1533–1540 (2000); and cyclodidemniserinol trisulfate (Mitchell, S. S. et al., *Org. Lett.* 2(11):1605–1607 (2000). Peptide based inhibitors include, among others, linear peptides (Puras Lutzke R. A. et al., *Proc. Natl. Acad. Sci. USA* 92(25):11456–11460 (1995); de Soultrait V. R. et al., *J Mol Biol.* 318(1):45–58; cyclic peptides (Singh, S. B. et al., *J Nat. Prod.* 64(7):874–882 (2001); and antibodies that bind and inhibit integrase activity (Yi, J. et al., *J Biol. Chem.* 277(14):12164–12174 (2002). All references are hereby incorporated by reference.

Additional antiviral agents useful in the present invention include compounds that inhibit or reduce entry of the virus into the cell. Some virus absorption inhibitors, such as cosalane derivatives, inhibits both the binding of gp120 to CD4 and fusion of the virus with the cell. Other agents inhibit fusion and/or absorption of the viral envelope with the cell membrane and include, among others, pentafuside (T-20); T-1249, a derivative of T-20; and betulinic acid. In another aspect, the inhibitors of viral entry are antagonists of viral co-receptors CXCR4 and CCR5, the 7-transmembrane-domain chemokine receptors used by all HIV-1 strains to infect cells. Interaction of viral protein gp120 with CD4 renders Env competent to bind the co-receptors. It is known that HIV-1 strain designate R5 uses CCR5; strains X4 use CXCR4; and R5X4 strains use both chemokine receptors. Viruses that successfully establish infections in previously uninfected hosts are generally R5 virus strains while emergence of X4 is correlated with accelerated disease progression. Agents capable of blockading interaction of viral Env with co-receptor CXCR4 include, bicyclam derivatives (Dessolin, J. et al., *J Med. Chem.* 42(2):229–241 (1999);

peptide inhibitors, for example ([Tyr5,12,Lys7]-polyphemusin II and its analogs, (Murakami, T. et al., *J. Exp. Med.* 186(8):1389–1393 (1997) and Arakaki, R. et al., *J Virol.* 73(2):1719–23 (1999)) and N-α-acetyl-nona-D-arginine (Arg) amide (Doranz, B. J. et al., *J. Exp. Med.* 186(8): 1395–1400 (1997); and distamycin analogs, 2,2'[4,4'-[[aminocarbonyl]amino]bis[-di[pyrrole-2-carboxamide-1,1'-dimethyl]]-6,8 napthalenedisulfonic acid]hexasodium salt (Howard, O. M. et al., *J Leukoc. Biol.* 64(1):6–13 (1998). Agents known to block interaction of virus with CCR5, include, among others, 1-[(2,4-dimethyl-3-pyridinyl)carbonyl]-4-methyl-4-[3(S)-methyl-4-[1(S)-[4-(trifluoromethyl) phenyl]ethyl]-1-piperazinyl]-piperidine N1-oxide (Tagat, J. R. *J Med. Chem.* 44(21):3343–3346 (2001); SCH-C (Strizki, J. M. et al., *Proc. Natl. Acad. Sci. USA* 98(22):12718–12723 (2001); TAK-779 (Baba, M. et al., *Proc. Natl. Acad. Sci. USA* 96: 5698–5703 (1999); and antibodies to CCR5 (Simmons, G. et al., *Science* 276:–279 (1997); Auraro, S. et al., *J Virol.* 74:4402–4406 (2001)). All references are hereby incorporated by reference.

The anti-retroviral agents may also comprise agents directed at inhibition of viral specific transcription or cell cycle inhibitors. One type of viral specific transcription inhibitor is a bistriazoloacridone analog (i.e., temacrazine (1,4-bis[3-(6-oxo-6H-v-triazolo[4,5,1-de]acridin-5-yl) amino-propyl]piperazine) and is described in Turpin, J. A. et al. *Antimicrob. Agents Chemother.* 42(3):487–494 (1998), hereby incorporated by reference. Inhibitors of the cell cycle are also known to inhibit viral replication, and include, among others, flavopiridol and roscovitine, both of which act by inhibiting cyclin dependent kinases.

In view of the known efficacy of multi-drug combinations of various antiviral compounds, also known in the art as "drug cocktails," encompassed with the scope of the invention are compositions comprising the subject peptides with multi-drug combinations. HAART (Highly Active Anti-retroviral Therapy) is a drug regimen consisting of at least three different anti-retroviral drugs. Thus, a plurality of anti-retroviral agents may be used in the present invention. These multi-drug combinations, include, but is not limited to, combinations of the various classes of antiviral agents described above. For example, one embodiment may comprise a combination containing the immunomodulatory peptides disclosed herein, particularly the D-stereo isomer of sequence Arg-nL-nL-nL-Arg-nL-nL-nL-Gly-Tyr (SEQ ID NO:1); a nucleoside or non-nucleoside reverse transcriptase inhibitor; and a protease inhibitor. Additionally, viral uptake inhibitors, such as pentafuside (T-20), may be included to further decrease spread of the virus. Other combinations may be made by those skilled in the art (e.g., different protease inhibitor combinations; cytokine and protease inhibitors; and the like).

Immunomodulatory Peptides

Immunomodulatory peptides suitable for use in the compositions and methods of the present invention are capable of inhibiting the cellular production of inflammatory cytokines including, e.g., tumor necrosis factor-α (TNF-α), interferon-γ (INF-γ), interleukin (IL)-1, and IL-4 as well as other cytokines, chemokines, hematopoietic growth factors, and the like. Preferred immunomodulatory peptides include or comprise one or more of the cytomodulating oligopeptides described in co-pending U.S. patent applications U.S. Ser. No. 08/838,916 and U.S. Ser. No. 09/028,083, the disclosures of which are incorporated by reference herein. Particularly preferred for use in the instant methods and compositions is an immunomodulatory peptide comprising the sequence Arg-nL-nL-nL-Arg-nL-nL-nL-Gly-Tyr, where nL is norleucine and all amino acids are the D-stereoisomer.

In addition, previously-known active compounds which may also find use in the subject invention include HLA-B $\alpha_1$-domain, particularly the amino acids from 75 to 84 and variations of this sequence where not more than 2 amino acids are replaced and in which amino acids do not include R and Y (see, e.g., WO 95/13288 and Buelow et al., supra). Also known are sequences based on the human TCR-α transmembrane region consisting of that sequence and sequences having not more than 2 mutations from that sequence (see Australian Application Nos. PN 0589 and PN 0590, filed Jan. 16, 1995). These sequences include 2 basic amino acids, where the 2 basic amino acids are separated by 4 aliphatic hydrophobic amino acids, although the application indicates that from 3 to 5 hydrophobic amino acids may be present. By mutation is intended each substitution of one amino acid for another or an insertion or deletion, each being counted as one mutation. In certain embodiments, the immunostimulatory peptides preferred for use herein may exclude such previously-known active compounds.

Generally, the phrase "immunomodulatory peptides" or "immunomodulating peptides" as used herein is meant to encompass all of the foregoing peptide compounds, as well as analogs, derivatives, fusion proteins and the like. In the preferred embodiment, the core sequence of the immunomodulatory peptide desirably comprises two basic amino acids separated by from three to four hydrophobic amino acids, particularly three hydrophobic amino acids, and particularly where the N-terminus is a basic amino acid. More desirably, the C-terminal amino acid is an aromatic amino acid, particularly tyrosine. Of particular interest is where at least one of the oligopeptide core terminal amino acids is an oligopeptide terminal amino acid, which may be in the monomeric or oligomeric form of the compound.

More particularly, the preferred immunomodulatory peptides for use in the compositions and methods of the present invention comprise oligopeptides having the sequence B-X-X-X-B-X-X-X-J-Tyr, where B is a basic amino acid, preferably Lys or Arg, particularly Arg on at least one position, preferably at both positions; J is Gly, B or an aliphatic hydrophobic amino acid of from 5 to 6 carbon atoms, particularly Gly or B; and X is an aliphatic or aromatic amino acid. In one embodiment, at least three X amino acid residues are the same non-polar aliphatic amino acid, preferably at least four are the same non-polar aliphatic amino acid, more preferably at least five are the same non-polar aliphatic amino acid, and most preferably, all are the same non-polar aliphatic amino acid. In a preferred embodiment, the non-polar aliphatic amino acids are of from 5 to 6 carbon atoms, particularly 6 carbon atoms, particularly the non-polar aliphatic amino acids Val, Ile, Leu, and nL. Thus, in some embodiments, X is any amino acid other than a charged aliphatic amino acid, and preferably any amino acid other than a polar aliphatic amino acid.

Of the six amino acids indicated by X in the B-X-X-X-B-X-X-X-J-Tyr peptide sequence, preferably at least 3 are aliphatic amino acids of from 5 to 6 carbon atoms, more preferably at least 4 are aliphatic amino acids of from 5 to 6 carbon atoms, most preferably at least 5 are aliphatic amino acids of 5–6 carbon atoms, more particularly 6 carbon atoms. In a preferred embodiment, the aliphatic amino acids are non-polar aliphatic amino acids of from 5 to 6 carbon atoms, particularly Val, Ile, Leu, and nL. The other amino acids may be other uncharged aliphatic amino acids, particularly non-polar aliphatic amino acids or aromatic amino acids.

Compositions of particular interest will have the following formula:

Arg-U-X-X-Arg-X-X-X-J-Tyr wherein all of the symbols have been defined previously except U, which comprises an uncharged aliphatic amino acid or aromatic amino acid, particularly a non-polar aliphatic amino acid or aromatic amino acid.

The amino acids may be naturally occurring amino acids or D-isomers thereof. The peptides may have one or more D-stereoisomer amino acids, up to all of the amino acids. Additionally, the immunomodulatory peptides may comprise oligomers of the subject peptides, particularly dimers thereof, or comprise a cyclic peptide, that is a ring structure, as further described below.

For the purposes of this invention, the amino acids (for the most part natural amino acids or their D-stereoisomers) will be broken down into the following categories:

| | | |
|---|---|---|
| 1. | Aliphatic | |
| | (a) non-polar aliphatic: | |
| | Gly, Ala, Val, nL, Ile, Leu | |
| | (b) polar aliphatic: | |
| | (1) uncharged: | |
| | Cys, Met, Ser, Thr, Asn, Gln | |
| | (2) charged: | |
| | Asp, Glu, Lys, Arg | |
| 2. | Aromatic: | |
| | Phe, His, Trp, Tyr | | wherein Pro may be included in the non-polar aliphatic amino acids, but will normally not be included. "nL" represents norleucine, where the non-polar aliphatic amino acids may be substituted with other isomers.

Either or both the N- and C-terminus of the peptide may be extended by not more than a total of about 100, usually not more than a total of about 30, more usually not more than about 20 amino acids, often not more than about 9 amino acids, where the amino acids will have fewer than 25%, more usually fewer than 20% polar amino acids, more particularly, fewer than 20% which are charged amino acids. Thus, extensions of the above sequences in either direction are mainly done with lipophilic, uncharged amino acids, particularly non-polar aliphatic amino acids and aromatic amino acids. The peptides may comprise L-amino acids, D-amino acids, or mixtures of D and L amino acids. Exceptions to the number of amino acid extensions are contemplated when the oligopeptides are expressed as fusion or chimeric proteins, as described below.

The peptides may be in the form of oligomers, particularly dimers of the peptides, which may be head to head, tail to tail, or head to tail, there being not more than about 6 repeats of the peptide. The oligomer may contain one or more D-stereoisomer amino acids, up to all of the amino acids. The oligomers may or may not include linker sequences between the peptides. When linker sequences are used, suitable linkers include those comprising uncharged amino acids and (Gly)n, where n is 1–7 (SEQ ID NO:3 6), Gly-Ser (e.g., (GS)$_n$, (GSGGS)$_n$ (SEQ ID NO:2) and (GGGS)$_n$ (SEQ ID NO:3), where n is at least 1), Gly-Ala, Ala-Ser, or other flexible linkers, as known in the art. Linkers of Gly or Gly-Ser may be used since these amino acids are relatively unstructured, which allows interaction of individual peptides with cellular target molecules and limits structural perturbations between peptides of the oligomer.

Immunomodulatory peptides may be in a structurally constrained form such as cyclic peptides of from about 9–50, usually 12 to 36 amino acids, where amino acids other than the specified amino acids may be present as a bridge. Thus, for example, addition of terminal cysteines allows formation of disulfide bridges to form a ring peptide. In some instances, one may use other than amino acids to cyclize the peptide. Bifunctional crosslinking agents are useful in linking two or more amino acids of the peptide. Other methods for ring formation are described in Chen et al., *Proc. Natl. Acad. Sci. USA* 89:5872–5876 (1992); Wu et al., *Protein Engineering* 6:471–478 (1993); Anwer, et al., *Int. J. Pep. Protein Res.* 36:392–399 (1990); and Rivera-Baeza, et al. *Neuropeptides* 30: 327–333 (1996); all references incorporated by reference. Alternatively, structurally constrained peptides are made by addition of dimerization sequences to the N- and C-terminal ends of the peptide, where interaction between dimerization sequences lead to formation of a cyclic type structure (see WO/0166565, incorporated by reference). In other instances, the subject peptides are expressed as fusions to other proteins, which provide a scaffold for constrained display on a surface exposed structure, such as a loop of a coiled-coil or β-turn structure.

One or both, usually one terminus of the immunomodulatory peptide, may be substituted with a lipophilic group, usually aliphatic or aralkyl, of from 8 to 36, usually 8 to 24 carbon atoms and fewer than two heteroatoms in the aliphatic chain, the heteroatoms usually being oxygen, nitrogen and sulfur. As further described below, the chain may be saturated or unsaturated, desirably having not more than 3 sites, usually not more than 2 sites of aliphatic unsaturation. Conveniently, commercially available aliphatic fatty acids, alcohols and amines may be used, such as caprylic acid, capric acid, lauric acid, myristic acid and myristyl alcohol, palmitic acid, palmitoleic acid, stearic acid and stearyl amine, oleic acid, linoleic acid, docosahexaenoic acid, etc. (see U.S. Pat. No. 6,225,444, hereby incorporated by reference). Preferred are unbranched, naturally occurring fatty acids between 14–22 carbon atoms in length. Other lipohilic molecules include glyceryl lipids and sterols, such as cholesterol. The lipophilic groups may be reacted with the appropriate functional group on the oligopeptide in accordance with conventional methods, frequently during the synthesis on a support, depending on the site of attachment of the oligopeptide to the support. Lipid attachment is useful where oligopeptides may be introduced into the lumen of the liposome, along with other therapeutic agents (e.g., immunosuppressive agents) for administering the peptides and agents into a host. Increasing lipophilicity is also known to increase transport of compounds across endothelial cells and therefore useful in promoting uptake of such compounds from the intestine or blood stream into surrounding tissues.

The terminal amino group or carboxyl group of the immunomodulatory peptide may be modified by alkylation, amidation, or acylation to provide esters, amides or substituted amino groups, where the alkyl or acyl group may be of from about 1 to 30, usually 1 to 24, preferably either 1 to 3 or 8 to 24, particularly 12 to 18 carbon atoms. The peptide or derivatives thereof may also be modified by acetylation or methylation to alter the chemical properties, for example lipophilicity. Other modifications include deamination of glutamyl and asparaginyl residues to the corresponding glutamyl and aspartyl residues, respectively; hydroxylation of proline and lysine; phosphorylation of hydroxyl groups of serine or threonine; and methylation of amino groups of lysine, arginine, and histidine side chains (see T. E. Creighton, *Proteins: Structure and Molecular Properties*, W.H. Freeman & Co. San Francisco, Calif., 1983).

Depending upon their intended use, particularly for administration to mammalian hosts, the subject peptides may be modified or attached to other compounds for the purposes of incorporation into carrier molecules, changing peptide bioavailability, extend or shorten half-life, control distribution to various tissues or the blood stream, diminish or enhance binding to blood components, and the like. The subject peptides may be bound to these other components by linkers which are cleavable or non-cleavable in the physiological environment such as blood, cerebrospinal fluid, digestive fluids, etc. The peptides may be joined at any point of the peptide where a functional group is present, such as hydroxyl, thiol, carboxyl, amino, or the like. Desirably, modification will be at either the N-terminus or the C-terminus. For these purposes, the subject peptides may be modified by covalently attaching polymers, such as polyethylene glycol, polypropylene glycol, carboxymethyl cellulose, dextran, polyvinyl alcohol, polyvinylpyrrolidine, polyproline, poly(divinyl-ether-co-maleic anhydride), poly(styrene-c-maleic anhydride), etc. Water soluble polymers, such a polyethylene glycol and polyvinylpyrrolidine are known to decrease clearance of attached compounds from the blood stream as compared to unmodified compounds. The modifications can also increase solubility in aqueous media and reduce aggregation of the peptides.

In another aspect, the peptide is preferably conjugated to small molecules for detection and isolation of the peptides, and to target or transport the immunomodulatory peptide into specific cells, tissues, and organs. Small molecule conjugates include haptens, which are substances that do not initiate an immune response when introduced by themselves into an animal. Generally, haptens are small molecules of molecular weight less than about 2 kD, and more preferably less that about 1 kD. Haptens include small organic molecules (e.g., p-nitrophenol, digoxin, heroin, cocaine, morphine, mescaline, lysergic acid, tetrahydrocannabinol, cannabinol, steroids, pentamidine, biotin, etc.). Binding to the hapten, for example for purposes of detection or purification, are done with hapten specific antibodies or specific binding partners, such as avidin which binds biotin.

Small molecules that target the conjugate to specific cells or tissues may also be used. It is known that presence of a biotin-avidin complex increases uptake of such modified peptides across endothelial cells. Linkage of peptides to carbohydrate moieties, for example to a β-glycoside through a serine residue on the peptide to form a β-O linked glycoside, enhances transport of the glycoside derivative via glucose transporters (Polt, R. et al. *Proc. Nat. Acad. Sci. USA* 91: 7144–7118 (1994); Oh et al. *Drug Transport and targeting*, In Membrane Transporters as Drug Targets, Amidon, G. L. and Sadee, W. eds., pg 59–88, Plenum Press, New York, 1999). Both of these types of modifications are encompassed within the scope of the present invention.

The immunomodulatory peptides may have attached various label moieties such as radioactive labels and fluorescent labels for detection and tracing. Fluorescent labels include, but are not limited to, fluorescein, eosin, Alexa Fluor, Oregon Green, rhodamine Green, tetramethylrhodamine, rhodamine Red, Texas Red, coumarin and NBD fluorophores, the QSY 7, dabcyl and dabsyl chromophores, BIODIPY, $Cy^5$, etc.

In one aspect, the peptides are joined to a wide variety of other peptides or proteins for a variety of purposes. The peptides may be linked to peptides or proteins to provide convenient functionalities for bonding, such as amino groups for amide or substituted amine formation, e.g., reductive amination; thiol groups for thioether or disulfide formation; carboxyl groups for amide formation; and the like. Of particular interest are peptides of at least 2, more usually 3, and not more than about 60 lysine groups, particularly polylysines of from about 4 to 20, usually 6 to 18 lysine units, referred to as multiple antigenic peptide system (MAPS), where the subject peptides are bonded to the lysine amino groups, generally at least about 20%, more usually at least about 50%, of available amino groups, to provide a multipeptide product (Butz, S. et al. *Pept. Res.* 7: 20–23 (1994)). In this way, molecules having a plurality of the subject peptides are obtained where the orientation of the subject peptides is in the same direction; in effect one has a linking group to provide for tail to tail di- or oligomerization.

In another aspect, other naturally occurring or synthetic peptides and proteins may be used to provide a carrier immunogen for generating antibodies to the subject peptides, where the antibodies serve as reagents for detecting the immunomodulatory peptides or for identifying other peptides having a comparable conformation. Suitable carriers for generating antibodies include, among others, hemocyanins (e.g., Keyhole Limpet hemocyanin—KLH); albumins (e.g., bovine serum albumin, ovalbumin, human serum albumin, etc.); immunoglobulins; thyroglobulins (e.g., bovine thyroglobulin); toxins (e.g., diptheria toxoid, tetanus toxoid); and polypeptides such as polylysine, as described above, or polyalanine-lysine. Although proteins are preferred carriers, other carriers, preferably high molecular weight compounds, may be used, including carbohydrates, polysaccharides, lipopolysaccharides, nucleic acids, and the like of sufficient size and immunogenicity. In addition, the resulting antibodies may be used to prepare anti-idiotypic antibodies which may compete with the subject peptides for binding to a target site. These anti-idiotypic antibodies are useful for identifying proteins to which the subject peptides bind.

In another aspect, the peptides are conjugated to other peptides or proteins for targeting the immunomodulatory peptide to cells and tissues, or adding additional functionalities to the peptides. For targeting, the protein or peptide used for conjugation will be selected based on the cell or tissue being targeted for therapy (Lee, R. et al. *Arthritis. Rheum.* 46: 2109–2120 (2002); Pasqualini, R. Q. *J. Nucl. Med.* 43: 159–62 (1999); Pasgualini, R. *Nature* 380: 364–366 (1996); hereby incorporated by reference). The proteins may also compromise poly-amino acids including, but not limited to, polyarginine; and polylysine, polyaspartic acid, etc., which may be incorporated into other polymers, such as polyethylene glycol, for preparation of vesicles or particles containing the conjugated peptides.

In another aspect, the subject peptides may be expressed in conjunction with other peptides or proteins, so as to be a portion of the polypeptide chain, either internal, or at the N- or C-terminus to form chimeric proteins or fusion proteins. By "fusion polypeptide" or "fusion protein" or "chimeric protein" herein is meant a protein composed of a plurality of protein components that, while typically joined in the native state, are joined by the respective amino and carboxy termini through a peptide linkage to form a continuous polypeptide. Plurality in this context means at least two, and preferred embodiments generally utilize three to twelve components, although more may be used. It will be appreciated that the protein components can be joined directly or joined through a peptide linker/spacer as outlined below.

Fusion polypeptides may be made to a variety of peptides or proteins to display the subject peptides in a conformationally restricted form, for targeting to cells and tissues, for targeting to intracellular compartments, tracking the fusion protein in a cell or an organism, and screening for other molecules that bind the peptides. Proteins useful for generating fusion proteins include various reporter proteins, structural proteins, cell surface receptors, receptor ligands, toxins, and enzymes. Exemplary proteins include fluorescent proteins (e.g., *Aequoria victoria* GFP, *Renilla reniformis* GFP, *Renilla muelleri* GFP, luciferases, etc., and variants thereof); β-galactosidase; alkaline phosphatase; *E. coli*. maltose binding protein; coat proteins of filamentous bacteriophage (e.g., minor coat protein, pIII, or the major coat protein, pVIII, for purposes of phage display); T cell receptor; charybdotoxin; and the like.

Fusion proteins also encompass fusions with fragments of proteins or other peptides, either alone or as part of a larger protein sequence. Thus, the fusion polypeptides may comprise fusion partners. By "fusion partners" herein is meant a sequence that is associated with the peptide that confers all members of the proteins in that class a common function or ability. Fusion partners can be heterologous (i.e., not native to the host cell) or synthetic (i.e., not native to any cell). The fusion partners include, but are not limited to, a) presentation structures, which provide the subject peptides in a conformationally restricted or stable form; b) targeting sequences, which allow localization of the peptide to a subcellular or extracellular compartment; c) stability sequences, which affects stability or protection from degradation to the peptide or the nucleic acid encoding it; d) linker sequences, which conformationally decouples the oligopeptide from the fusion partner; and e) any combination of the above.

In one aspect, the fusion partner is a presentation structure. By "presentation structure" as used herein is meant a sequence that when fused to the subject peptides presents the peptides in a conformationally restricted form. Preferred presentation structures enhance binding interactions with other binding partners by presenting a peptide on a solvent exposed exterior surface, such as a loop. Generally, such presentation structures comprise a first portion joined to the N-terminus of the immunomodulatory peptide and a second portion joined to the C-terminal end of the subject peptide. That is, the peptide of the present invention is inserted into the presentation structures. Preferably, the presentation structures are selected or designed to have minimal biological activity when expressed in the target cells.

Preferably, the presentation structures maximize accessibility to the peptides by displaying or presenting the peptide or an exterior loop. Suitable presentation structures include, but are not limited to, coiled coil stem structures, minibody structures, loops on β-turns, dimerization sequences, cysteine linked structures, transglutaminase linked structures, cyclic peptides, helical barrels, leucine zipper motifs, etc.

In one embodiment, the presentation structure is a coiled-coil structure, which allows presentation of the subject peptide on an exterior loop (see Myszka et al. *Biochemistry* 33: 2362–2373 (1994)), such as a coiled-coil leucine zipper domain (see Martin et al. *EMBO J.* 13: 5303–5309 (1994)). The presentation structure may also comprise minibody structures, which is essentially comprised of a minimal antibody complementarity region. The minibody structure generally provides two peptide regions that are presented along a single face of the tertiary structure in the folded protein (see Bianchi et al. *J. Mol. Biol.* 236: 649–659 (1994); Tramontano et al. *J. Mol. Recognit.* 7: 9–24 (1994)).

In another aspect, the presentation structure comprises two dimerization sequences. The dimerization sequences, which can be same or different, associate non-covalently with sufficient affinity under physiological conditions to structurally constrain the displayed peptide; that is, if a dimerization sequence is used at each terminus of the subject oligopeptide, the resulting structure can display the subject peptide in a structurally limited form. A variety of sequences are suitable as dimerization sequences (see for example, WO 99/51625; incorporated by reference). Any number of protein-protein interaction sequences known in the art are useful.

In a further aspect, the presentation sequence confers the ability to bind metal ions to generate a conformationally restricted secondary structure. Thus, for example, C2H2 zinc finger sequences are used. C2H2 sequences have two cysteines and two histidines placed such that a zinc ion is chelated. Zinc finger domains are known to occur independently in multiple zinc-finger peptides to form structurally independent, flexibly linked domains (see Nakaseko, Y. et al. *J. Mol. Biol.* 228: 619–636 (1992)). A general consensus sequence is (5 amino acids)-C-(2 to 3 amino acids)-C-(4 to 12 amino acids)-H-(3 amino acids)-H-(5 amino acids) (SEQ ID NO:4). A preferred example would be -FQCEEC-random peptide of 3 to 20 amino acids-HIRSHTG (SEQ ID NO:5). Similarly, CCHC boxes having a consensus sequence -C-(2 amino acids)-C-(4 to 20 random peptide)-H-(4 amino acids)-C- (SEQ ID NO:6) can be used, (see Bavoso, A. et al. *Biochem. Biophys. Res. Commun.* 242: 385–389 (1998)). Other examples include (1) -VKCFNC-4 to 20 random amino acids-HTARNCR- (SEQ ID NO:7), based on the nucleocapsid protein P2; (2) a sequence modified from that of the naturally occurring zinc-binding peptide of the Lasp-1 LIM domain (Hammarstrom, A. et al. *Biochemistry* 35: 12723–32 (1996)); and (3)-MNPNCARCG-4 to 20 random amino acids-HKACF- (SEQ ID NO:8), based on the NMR structural ensemble 1ZEP (Hammarstrom et al., supra).

In yet another aspect, the presentation structure is a sequence that comprises two or more cysteine residues, such that a disulfide bond may be formed, resulting in a conformationally constrained structure. That is, use of cysteine containing peptide sequences at each terminus of the subject immunomodulatory peptides results in cyclic peptide structures, as described above. A cyclic structure reduces susceptibility of the presented peptide to proteolysis and increases accessibility to its target molecules. As will be appreciated by those skilled in the art, this particular embodiment is particularly suited when secretory targeting sequences are used to direct the peptide to the extracellular space.

In another embodiment, the fusion partner is a targeting sequence. Targeting sequences comprise binding sequences capable of causing binding of the expressed product to a predeterimed molecule or class of molecules while retaining bioactivity of the expression product; sequences signaling selective degradation of the fusion protein or binding partners; and sequences capable of constitutively localizing peptides to a predetermined cellular locale. Typical cellular locations include subcellular locations (e.g, Golgi, endoplasmic recticulum, nucleus, nucleoli, nuclear membrane, mitochondria, secretory vesicles, lysosomes) and extracellular locations by use of secretory signals.

Various targeting sequences are known in the art. Targeting to nucleus is achieved by use of nuclear localization signals (NLS). NLSs are generally short, positively charged domains that directs the proteins in which the NLSs is present to the cells nucleus. Typical NLSs sequences include the single basic NLSs of SV40 large T antigen (Kalderon et al. *Cell* 39: 499–509 (1984)); human retinoic acid receptor-β nuclear localization signal (NF-kB p50 and p65 (Ghosh et al. *Cell* 62: 1019–1029 (1990)); Nolan et al. *Cell* 64: 961–999 (1991)); and the double basic NLSs' as exemplified by nucleoplasmin (Dingwall et al. *J. Cell Biol.* 107: 641–649 (1988)).

In another aspect the targeting sequences are membrane anchoring sequences. Peptides are directed to the membrane via signal sequences and stably incorporated in the membrane through a hydrophobic transmembrane domain (designated as TM). The TM segment is positioned appropriately on the expressed fusion protein to display the subject peptide either intracellularly or extracellularly, as is known in the art. Membrane anchoring sequences and signal sequences include, but are not limited to, those derived from (a) class I integral membrane proteins such as IL-2 receptor β-chain; Hatekeyama et al. *Science* 244: 551–556 (1989)) and inuslin receptor β-chain (Hetekayama et al, supra); (b) class II integral membrane proteins such as neutral endopeptidase (Malfroy et al *Biochem. Biophys. Res. Commun.* 144: 59–66 (1987)); and (c) type III proteins such as human cytochrome P450 NF25 (Hetekayama et al, supra); and those from CD8, ICAM-2, IL-8R, and LFA-1.

Membrane anchoring sequences also include the GPI anchor, which results in covalent bond formation between the GPI anchor sequence and the lipid bilayer via a glycosyl-phosphatidylinositol. GPI anchor sequences are found in various proteins, including Thy-1 and DAF (see Homans et al. *Nature* 333: 269–272 (1988)). Similarly, acylation sequences allow for attachment of lipid moieties, e.g., isoprenylation (i.e., farnesyl and geranyl-geranyl; see Farnsworth et al. *Proc. Natl. Acad. Sci. USA* 91: 11963–11967 (1994) and Aronheim et al. *Cell* 78: 949–61 (1994)), myristoylation (Stickney, J. T. *Methods Enzymol.* 332: 64–77 (2001)), or palmitoylation. In one aspect, the subject peptide will be bound to a lipid group at a terminus, so as to be able to be bound to a lipid membrane, such as a liposome.

Other intracellular targeting sequences are lysozomal targeting sequences (e.g., sequences in LAMP-1 and LAMP-2; Uthayakumar et al. *Cell Mol. Biol. Res.* 41: 405–420 (1995) and Konecki et al. *Biochem. Biophys. Res. Comm.* 205:1–5 (1994)); mitochondrial localization sequences (e.g., mitochondrial matrix sequences, mitochondrial inner membrane sequences, mitochondrial intermembrance sequences, or mitochondrial outer membrane sequences; see Shatz, G. *Eur. J. Biochem.* 165:1–6 (1987)); endoplasmic recticulum localization sequences (e.g., calreticulin, Pelham, H. R. *Royal Soc. London Transactions B:* 1–10 (1992); adenovirus E3/19K protein, Jackson et al. *EMBO J.* 9: 3153–3162 (1990)); and peroxisome localization sequences (e.g., luciferase peroxisome matrix sequence, Keller et al. *Proc. Natl. Acad. Sci. USA* 4: 3264–3268 (1987)).

In another aspect, the targeting sequences is a secretory signal sequence which effects secretion of the peptide. A large number of secretory sequences are known to direct secretion of a peptide into the extracellular space when placed at the amino end relative to the peptide of interest, particularly for secretion of a peptide by cells, including transplanted cells. Suitable secretory signals included those found in IL-2 (Villinger et al. *J. Immuno.* 155: 3946–3954 (1995)), growth hormone (Roskam et al. *Nucleic Acids Res.* 7: 305–320 (1979)), preproinsulin, and influenza HA protein.

The fusion partner may further comprise a stability sequence, which confers stability to the fusion protein or the nucleic acid encoding it. Thus, for example, incorporation of glycines after the initiating methionine (e.g., MG or MGG) can stabilize or protect the fused peptide from degradation via ubiquitination as per the N-End rule of Varshavsky, thus conferring increased half-life in a cell.

Additional amino acids may be added for tagging the peptide for purposes of detection or purification. These sequences may comprise epitopes recognized by antibodies (e.g., flag tags) or sequences that bind ligands, such a metals ions. Various tag sequences and ligand binding sequences are well known in the art. These include, but is not limited to, poly-histidine (e.g., 6×His tags, which are recognized by antibodies but also bind divalent metal ions); poly-histidine-glycine (poly-his-gly) tags; flu HA tag polypeptide; c-myc tag; Flag peptide (Hopp et al. *BioTechnology* 6: 1204–1210 (1988)); KT3 epitope peptide; tubulin epitope peptide (Skinner et al. *J. Biol. Chem.* 266: 15163–12166 (1991)); and T7 gene 10 protein peptide tag (Lutz-Freyermuth et al. *Proc. Natl. Acad. Sci. USA* 87: 6363–6397 (1990)).

Fusion partners includes linker or tethering sequences for linking the peptides and for presenting the peptides in an unhindered structure. As discussed above, useful linkers include glycine polymers (G)n where n is 1 to about 7 (SEQ ID NO:36), glycine-serine polymers (e.g., (GS)n, (GSGGS)n (SEQ ID NO:2) and (GGGS)n (SEQ ID NO:3), where n is at least 1), glycine-alanine polymers, alanine-serine polymers, and other flexible linkers known in the art. Preferably, the linkers are glycine or glycine-serine polymers since these amino acids are relatively unstructured, hydrophilic, and are effective for joining segments of proteins and peptides.

In the present invention, combinations of fusion partners may be used. Any number of combinations of presentation structures, targeting sequences, rescue sequences, tag sequences and stability sequences may be used with or without linker sequences.

The immunomodulatory peptides of the present invention may be prepared in a number of ways. Chemical synthesis of peptides are well known in the art. Solid phase synthesis is commonly used and various commercial synthetic apparatuses are available, for example automated synthesizers by Applied Biosystems Inc., Foster City, Calif.; Beckman; etc. Solution phase synthetic methods may also be used, although it is less convenient. By using these standard techniques, naturally occurring amino acids may be substituted with unnatural amino acids, particularly D-stereoisomers, and also with amino acids with side chains having different lengths or functionalities. Functional groups for conjugating to small molecules, label moieties, peptides, or proteins, or for purposes of forming cyclized peptides may be introduced into the molecule during chemical synthesis. In addition, small molecules and label moieties may be attached during the synthetic process. Preferably, introduction of the functional groups and conjugation to other molecules minimally affects the structure and function of the subject peptide.

The N- and C-terminus may be derivatized using conventional chemical synthetic methods. The immunomodulatory peptides of the invention may contain an acyl group, such as an acetyl group. Methods for acylating, and specifically for acetylating the free amino group at the N-terminus are well known in the art. For the C-terminus, the carboxyl group may be modified by esterification with alcohols or amidated to form —$CONH_2$, CONHR, or CONR, wherein each R is a hybroxycarbyl (1–6 carbons). Methods of esterification and amidation are done using well known techniques.

The immunomodulatory peptides of the present invention may also be present in the form of a salt, generally in a salt form which is pharmaceutically acceptable. These include inorganic salts of sodium, potassium, lithium, ammonium, calcium, magnesium, iron, zinc, copper, manganese, and the like. Various organic salts of the peptide may also be made with, including, but not limited to, acetic acid, propionic acid, pyruvic acid, maleic acid, succinic acid, tartaric acid, citric acid, benozic acid, cinnamic acid, salicylic acid, etc.

Synthesis of the immunomodulatory peptides and derivatives thereof may also be carried out by using recombinant techniques. For recombinant production, one may prepare a nucleic acid sequence which encodes a single oligopeptide or preferably a plurality of the subject peptides in tandem with an intervening amino acid or sequence, which allows for cleavage to the single peptide or head to tail dimers. Where methionine or tryptophane is absent, an intervening methionine or tryptophane may be incorporated, which allows for single amino acid cleavage using CNBr or BNPS-Skatole (2-(2-nitrophenylsulfenyl)-3-methyl-3-bromoindolenine), respectively. Alternatively, cleavage is accomplished by use of sequences that are recognized by particular proteases for enzymatic cleavage or sequences that act as self-cleaving sites (e.g., 2A sequences of apthoviruses and cardioviruses; Donnelly, M. L. *J. Gen. Virol.* 78: 13–21. (1997); Donnelly, M. L. *J. Gen. Virol.* 82:1027–41 (2001), hereby incorporated by reference). The subject peptide may also be made as part of a larger peptide, which can be isolated and the oligopeptide obtained by proteolytic cleavage or chemical cleavage. The particular sequence and the manner of preparation will be determined by convenience, economics, purity required, and the like. To prepare these compositions, a gene encoding a particular peptide, protein, or fusion protein is joined to a DNA sequence encoding the immunomodulatory peptides of the present invention to form a fusion nucleic acid, which is introduced into an expression vector. Expression of the fusion nucleic acid is under the control of a suitable promoter and other control sequences, as defined below, for expression in a particular host cell or organism (see, Sambrook et al., Molecular Biology: A Laboratory Manual, 3rd Ed., Cold Spring Harbor Laboratories, Cold Spring Harbor, N.Y., 2001; Ausubel et al. Current Protocols in Molecular Biology, John Wiley & Sons, New York, N.Y., 1988, updates up to 2002; incorporated by reference).

When the synthesis or delivery of the immunomodulatory peptides are via nucleic acids encoding the subject peptides, the nucleic acids are cloned into expression vectors and introduced into cells or a host. The expression vectors are either self-replicating extrachromosomal vectors or vectors that integrate into the host chromosome, for example vectors based on retroviruses, vectors with site specific recombination sequences, or by homologous recombination. Generally, these vectors include control sequences operably linked to the nucleic acids encoding the peptides. By "control sequences" is meant nucleic acid sequences necessary for expression of the subject peptides in a particular host organism. Thus, control sequences include sequences required for transcription and translation of the nucleic acids, including, but not limited to, promoter sequences, enhancer or transcriptional activator sequences, ribosomal binding sites, transcriptional start and stop sequences; polyadenylation signals; etc.

A variety of promoters are useful in expressing the peptides of the present invention. The promoters may be constitutive, inducible, and/or cell specific and may comprise natural promoters, synthetic promoters (e.g. tTA tetracycline inducible promoters), or hybrids of various promoters. Promoters are chosen based on, among others, the cell or organism in which the proteins are to be expressed, the level of desired expression, and regulation of expression. Suitable promoters are bacterial promoters (e.g., pL I phage promoter, tac promoter, lac lac promoter, etc.); yeast based promoters (e.g., GAL4 promoter, alcohol dehydrogenase promoter, tryptophane synthase promoter, copper inducible CUPI promoter, etc.), plant promoters (e.g., CaMV S35, nopoline synthase promoter, tobacco mosaic virus promoter, etc), insect promoters (e.g., Autographa nuclear polyhedrosis virus, Aedes DNV viral p& and p61, hsp70, etc.), and promoters for expression mammalian cells (e.g., ubiquitin gene promoter, ribosomal gene promoter, β-globin promoter, thymidine kinase promoter, heat shock protein promoters, and ribosomal gene promoters, etc.), and particularly viral promoters, such as cytomegalovirus (CMV) promoter, simian virus (SV40) promoter, and retroviral promoters.

By "operably linked" herein is meant that a nucleic acid is placed into a functional relationship with another nucleic acid. In the present context, operably linked means that the control sequences are positioned relative to the nucleic acid sequence encoding the subject peptides in such a manner that expression of the encoded peptide occurs. The vectors may comprise plasmids or comprise viral vectors, for example retroviral vectors, which are useful delivery systems if the cells are dividing cells, or lentiviral and adenoviral vectors if the cells are non-dividing cells. Particularly preferred are self-inactivating retroviral vectors (SIN vectors), which have inactivated viral promoters at the 3'-LTR, thereby permiting control of expression of heterologous genes by use of non-viral promoters inserted into the viral vector (see for example, Hoffman et al. *Proc. Natl. Acad. Sci. USA* 93: 5185 (1996). As will be appreciated by those in the art, modifications of the system by pseudotyping allows use of retroviral vectors for all eukaryotic cells, particularly for higher eukaryotes (Morgan, R. A. et al. *J. Virol.* 67: 4712–21 (1993); Yang, Y. et al. *Hum. Gene Ther.* 6:1203–13 (1995)).

In addition, the expression vectors also contain a selectable marker gene to allow selection of transformed host cells. Generally, the selection will confer a detectable phenotypes that enriches for cells containing the expression vector and further permits differentiation between cells that express and do not express the selection gene. Selection genes are well known in the art and will vary with the host cell used. Suitable selection genes included genes that render the cell resistant to a drug, genes that permit growth in nutritionally deficient media, and reporter genes (e.g. β-galactosidase, fluorescent proteins, glucouronidase, etc.), all of which are well known in the art and available to the skilled artisan.

There are a variety of techniques available for introducing nucleic acids into viable cells. By "introduced" into herein is meant that the nucleic acid enters the cells in a manner suitable for subsequent expression of the nucleic acid. Techniques for introducing the nucleic acids will vary depending on whether the nucleic acid is transferred in vitro into cultured cells or in vivo into the cells of the intended host organism and the type of host organism. Exemplary for introducing the nucleic acids in vitro include the use of liposomes, Lipofectin®, electroporation, microinjection, cell fusion, DEAE dextran, calcium phosphate prepcipitation, and bioloistic particle bombardment. Techniques for transfer in vivo include direct introduction of the nucleic acid, use of viral vectors, typically retroviral vectors, and liposome mediated transfection, such as viral coated liposome mediated transfection. The nucleic acids expressing the peptides of the present invention may exist transiently or stably in the cytoplasm or stably integrate into the chromosome of the host (i.e., through use of standard regulatory sequences, selection markers, etc.). Suitable selection genes and marker genes are used in the expression vectors of the present invention.

In some situations, it is desirable to include an agent that targets the target cells or tissues, such as an antibody specific for a cell surface protein or the target cell, a ligand for a receptor on the target cell, a lipid component on the cell membrane, or a carbohydrate on the cell surface. If liposomes are employed, proteins that bind a cell surface protein which is endocytosed may be used for targeting and/or facilitating uptake. These include as non-limiting examples, capsid proteins or fragments thereof tropic for a particular cell types, antibodies for proteins which undergo internalization (see Wu et al. *J. Biol. Chem.* 262: 4429–4432 (1987); Wagner et al. *Proc. Natl. Acad. Sci. USA* 87: 3410–3414 (1990)), and proteins that direct localization (e.g., antibody to transferrin receptor for targeting to brain) or enhance in vivo half-life.

Expression is done in a wide range of host cells that span prokaryotes and eukaryotes, including bacteria, yeast, plants, insects, and animals. The immunomodulatory peptides of the present invention may be expressed in, among others, *E. coli., Saccharomyces cerevisiae, Saccharomyces pombe*, Tobacco or Arabidopsis plants, insect Schneider cells, and mammalian cells, such as COS, CHO, HeLa, and the like, either intracellularly or in a secreted form by fusing the peptides to an appropriate signal peptide. Secretion from the host cell may be done by fusing the DNA encoding the peptide and a DNA encoding a signal peptide. Secretory signals are well known in the art for bacteria, yeast, insects, plants, and mammalian systems. Nucleic acids expressing the opeptides may be inserted into cells, for example stem cells for tissue expression or bacteria for gut expression, and the cells transplanted into the host to provide an in vivo source of the peptides.

If desired, various groups are introduced into the peptide during synthesis or during expression, which allows for linking to other molecules or to a surface. Thus, cysteines can be used to make thioethers or cyclic peptides, histidines for linking to a metal ion complex, carboxyl groups for forming amides or esters, amino groups for forming amides, and the like. When cysteine residues are introduced for cyclizing the peptide, formation of disulfide bonds are conducted in the presence of mild oxidizing agents. Chemical oxidants may be used, or the cysteine bearing peptides are exposed to oxygen to form the linkages, typically in a suitable solution such as a aqueous buffer containing DMSO. As described above, lipids may be attached either chemically or by use of appropriate lipidation sequences in the expressed peptide.

For conjugating various molecules to the peptides of the present invention, functional groups on the peptides and the other molecule are reacted in presence of an appropriate conjugating (e.g., crosslinking) agent. The type of conjugating or crosslinking agent used will depend on the functional groups, such as primary amines, sulfhydryls, carbonyls, carbohydrates and carboxylic acids being used. Agents may be fixatives and crosslinking agents, which may be homo-bifunctional, heterobifunctional, or trifunctional crosslinking agents (Pierce Endogen, Chicago, Ill.). Commonly used fixatives and crosslinking agents include formaldehyde, glutaraldehyde, 1,1-bis(diazoacetyl)-2-phenylethane, N-hydroxysuccinimide esters, dissuccimidyl esters, maleimides (e.g., bis-N-maleimido-1-8-octane), and carbodiimides (e.g., N-ethyl-N'-(3-dimethylaminopropyl)-carbodiimide; dicyclohexylcarbodiimide. Spacer molecules comprising alkyl or substituted alkyl chains with lengths of 2–20 carbons may be used to separate conjugates. Preferably, reactive functional groups on the peptide not selected for modification are protected prior to coupling of the peptide to other reactive molecules to limit undesired side reactions. By "protecting group" as used herein is a molecule bound to a specific functional group which is selectively removable to reexpose the functional group (see Greene, T. W. and Wuts, P. G. M. *Protective Groups in Organic Synthesis* (3rd ed.), John Wiley & Sons, Inc., New York, 1999). The peptides may be synthesized with protected amino acid precursors or reacted with protecting groups following synthesis but before reacting with crosslinking agent. Conjugations may also be indirect, for example by attaching a biotin moiety, which can be contacted with a compound or molecule which is coupled to streptavidin or avidin.

For peptides that have reduced activity in the conjugated form, the linkage between the peptides and the conjugated compound is chosen to be sufficiently labile to result in cleavage under desired conditions; for example after transport to desired cells or tissues. Biologically labile covalent bonds, e.g., imimo bonds and esters, are well known in the art (see U.S. Pat. No. 5,108,921, hereby incorporated by reference). These modifications permit administration of the peptides in potentially a less active form, which is then activated by cleavage of the labile bond.

In a preferred embodiment, the immunomodulatory peptides of the present invention may be purified or isolated after synthesis or expression. By "purified" or "isolated" is meant free from the environment in which the peptide is synthesized or expressed and in a form where it can be practically used. Thus purified or isolated is meant that the peptide or its derivative is substantially pure, i.e., more than 90% pure, preferably more than 95% pure, and preferably more than 99% pure. The peptides and derivatives thereof may be purified and isolated by way known to those skilled in the art, depending on other components present in the sample. Standard purification methods include electrophoretic, immunological, and chromatographic techniques, including ion exchange, hydrophobic, affinity, size exclusion, reverse phase HPLC, and chromatofocusing. The proteins may also be purified by selective solubility, for instance in the presence of salts or organic solvents. The degree of purification necessary will vary depending on use of the subject peptides. Thus, in some instances no purification will be necessary.

For the most part, the compositions used will comprise at least 20% by weight of the desired product, more usually at least about 75% by weight, preferably at least about 95% by weight, and usually at least about 99.5% by weight, relative to contaminants related to the method of product preparation, the purification procedure, and its intended use, for example with a pharmaceutical carrier for the purposes of therapeutic treatment. Usually, the percentages will be based upon total protein.

The subject peptides in combination with the anti-retroviral agents are useful in treating gastrointestinal dysfunction in infected patients. In addition, these combination treatments may be applied to stabilizing or raising the level of T-cells in an HIV infected patient, including levels of CD4+ and CD8+ double positive T cells and CD4+ single positive T cells. The increase in number of double positive cells indicates an increase in number of precursor T-cells, especially those developing in α:β T cell lineage which gives rise to the functional subsets of CD4+ and CD8+ T cells (see Benoist, C. and Mathis, D, "Lymphocyte Differentiation and Biology," in *Fundamental Immunology*, 4th Ed. (Paul, W. ed.), Chapter 11, Lippincott-Raven Publishers, New York, N.Y. (1999); Janeway, C. A. et al., *Immunobiology*, 5th Ed., Chapter 7, Garland Publishing, New York, N.Y. (2001). Increasing the number of precursor T cells and mature T cells has a potential benefit in preventing further deterioration and/or or in promoting restablishment of a normalized immune system in HIV infected individuals.

Additional Therapeutic Agents

Additional therapeutic or pharmaceutically active agents may also be advantageously used in combination with the above compositions, including corticosteroids (e.g., prednisone, methylprednisolone, dexamethasone, etc.); immunomodulators (e.g., interferon, including interferon-b1a, interferon-b1a); immune suppressants (e.g., azathioprine, 6-mercaptopurine, cyclosporin); anti-inflammatory compounds, including, but not limited to, non-steroidal anti-inflammatory compounds (e.g., sulfasalzine, aminosalicylates, celecoxib, lipoxins, etc.); hydroxyurea; and thalidomide, which is known to increase IL-2 and IL-12 levels.

As will be appreciated by those skilled in the art, in certain circumstances where the gastrointestinal dysfunction is further complicated by pathogen infection, the peptides of the present invention may be used with drugs directed against eliminating or killing the pathogen. These include antibiotics, anti-fungal agents, anti-protozoan agents, and anti-viral agents, as is well known in the art. These drugs may be used prior to, concomitantly with, or subsequent to treatment with the peptides described herein.

The present invention may also be used in combination of anti-inflammatory cytokines, growth factors, or leukocyte migration inhibitory compounds. Useful cytokines include, but are not limited to, IL-2, IL-10, IL-11, IL-12 and IL-13, particularly IL-2 and IL-12, which are known to suppress production of inflammatory cytokines and to be involved in restoring the immune system. Growth factors include transforming growth factor-β (TGF-β), which is upregulated in inflammatory bowel disorders, particularly Crohn's disease, and GM-CSF. These cytokines and growth factors may be administered as purified proteins—obtained naturally or from recombinant sources—or administered in the form of nucleic acids that express these peptides, particularly as fusion proteins. Leukocyte migration inhibitory compounds, include, among others, antibodies directed against adhesion molecules and their cognate receptors involved in cell adhesion, particularly leukocyte adhesion to endothelial cells, such as for E-, L-, and P-selectins; vascular cell adhesion molecule-1 (VCAM-1); mucosal addressin cell adhesion molecule, (MAdCAM-1); and intercellular adhesion molecule-1 (ICAM-1); and their cognate receptors, such as $\alpha_4\beta_1$ and $\alpha_4\beta_7$.

In another preferred embodiment, the immunomodulatory peptides are further combined with other inhibitors of pro-inflammatory cytokine activity or agents that reduce synthesis of these cytokines. These include agents that block cytokine function, such as antibodies to IL-5, IL-6, IL-8, IL-18, IL-23, TNF-α, and IFN-γ, and antibodies to their cognate receptors; and cytokine receptor antagonists (see for example, U.S. Pat. No. 6,436,927). In addition, blocking agents include soluble receptors proteins, for instance receptors fused to IgC domains, that bind to cytokines to reduce activation of CD4+ T-cells, macrophages, and granulocytes involved in progression of the inflammatory reaction, particularly in the gastrointestinal system of HIV infected individuals.

Pharmaceutical Formulations

The subject compositions, either alone or in combination, may be used in vitro, ex vivo, and in vivo depending on the particular application. In accordance, the present invention provides for administering a pharmaceutical composition comprising a pharmaceutically acceptable carrier and a pharmacologically effective amount of one or more of the subject peptides, or suitable salts thereof. The pharmaceutical composition may be formulated as powders, granules, solutions, suspensions, aerosols, solids, pills, tablets, capsules, gels, topical cremes, suppositories, transdermal patches, etc.

As indicated above, pharmaceutically acceptable salts of the peptides is intended to include any art recognized pharmaceutically acceptable salts including organic and inorganic acids and/or bases. Examples of salts include sodium, potassium, lithium, ammonium, calcium, as well as primary, secondary, and tertiary amines, esters of lower hydrocarbons, such as methyl, ethyl, and propyl. Other salts include organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any of standard pharmaceutically accepted carriers known to those of ordinary skill in the art in formulating pharmaceutical compositions. Thus, the subject peptides, by themselves, such as being present as pharmaceutically acceptable salts, or as conjugates, or nucleic acid vehicles encoding such peptides, may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or the like, or as solid formulations in appropriate excipients. The pharmaceutical compositions also contain anti-retroviral agents when such agents are part of the compositions. Additionally, the formulations may include bactericidal agents, stabilizers, buffers, emulsifiers, preservatives, sweetening agents, lubricants, or the like. If administration is by oral route, the oligopeptides may be protected from degradation by using a suitable enteric coating, or by other suitable protective means, for example internment in a polymer matrix such as microparticles or pH sensitive hydrogels.

Suitable formulations may be found in, among others, Remington's Pharmaceutical Sciences, 17th edition, Mack Publishing Co., Philadelphia, Pa., 1985 and Handbook of Pharmceutical Excipients, 3rd Ed, Kibbe, A. H. ed., Washington D.C., American Pharmaceutical Association, 2000; hereby incorporated by reference in their entirety. The pharmaceutical compositions described herein can be made in a manner well known to those skilled in the art (e.g., by means conventional in the art, including mixing, dissolving, granulating, levigating, emulsifying, encapsulating, entrapping or lyophilizing processes).

Additionally, the peptides, either alone or with the anti-retroviral agents may also be introduced or encapsulated into the lumen of liposomes for delivery and for extending life time of the peptide formulations ex vivo or in vivo. As known in the art, liposomes can be categorized into various types: multilamellar (MLV), stable plurilamellar (SPLV), small unilamellar (SUV) or large unilamellar (LUV)

vesicles. Liposomes can be prepared from various lipid compounds, which may be synthetic or naturally occurring, including phosphatidyl ethers and esters, such as phosphotidylserine, phosphotidylcholine, phosphatidyl ethanolamine, phosphatidylinositol, dimyristoylphosphatidylcholine; steroids such as cholesterol; cerebrosides; sphingomyelin; glycerolipids; and other lipids (see for example, U.S. Pat. No. 5,833,948).

Cationic lipids are also suitable for forming liposomes. Generally, the cationic lipids have an net positive charge and have a lipophilic portion, such as a sterol or an acyl or diacyl side chain. Preferably, the head group is positively charged. Typical cationic lipids include 1,2-dioleyloxy-3-(trimethylamino)propane; N-[1-(2,3,-ditetradecycloxy)propyl]-N,N-dimethyl-N-N-hydroxyethylammonium bromide; N-[1-(2, 3-dioleyloxy)propyl]-N,N-dimethyl-N-hydroxy ethylammonium bromide; N-[1-(2,3-dioleyloxy) propyl]-N, N,N-trimethylammonium chloride; 3-[N-(N', N'-dimethylaminoethane) carbamoyl]cholesterol; and dimethyldioctadecylammonium.

Of particular interest are fusogenic liposomes, which are characterized by their ability to fuse with a cell membrane upon appropriate change in physiological condition or by presence of fusogenic component, particularly a fusogenic peptide or protein. In one aspect, the fusogenic liposomes are pH and temperature sensitive in that fusion with a cell membrane is affected by change in temperature and/or pH (see for example, U.S. Pat. Nos. 4,789,633 and 4,873,089). Generally, pH sensitive liposomes are acid sensitive. Thus, fusion is enhanced in physiological environments where the pH is mildly acidic, for example the environment of a lysosome, endosome and inflammatory tissues. This property allows direct release of the liposome contents into the intracellular environment following endocytosis of liposomes (see Mizoue, T. *Int. J. Pharm.* 237: 129–137 (2002)).

Another form of fusogenic liposomes comprise liposomes that contain a fusion enhancing agent. That is, when incorporated into the liposome or attached to the lipids, the agents enhance fusion of the liposome with other cellular membranes, thus resulting in delivery of the liposome contents into the cell. The agents may be fusion enhancing peptides or proteins, including hemaggulutinin HA2 of influenza virus (Schoen, P. *Gene Ther.* 6: 823–832 (1999)); Sendai virus envelope glycoproteins (Mizuguchi, H. *Biochem. Biophys. Res. Commun.* 218: 402–407 (1996)); vesicular stomatitis virus envelope glycoproteins (VSV-G) glycoprotein (Abe, A. et al. *J Virol* 72: 6159–63 (1998)); peptide segments or mimics of fusion enhancing proteins; and synthetic fusion enhancing peptides (Kono, K. et al. *Biochim. Biophys. Acta.* 1164: 81–90 (1993); Pecheur, E. I. *Biochemistry* 37: 2361–71 (1998); U.S. Pat. No. 6,372,720).

Liposomes also include vesicles derivatized with a hydrophilic polymer, as provided in U.S. Pat. Nos. 5,013,556 and 5,395,619, hereby incorporated by reference, (see also, Kono, K. et al. *J. Controlled Release* 68: 225–35 (2000); Zalipsky, S. et al. *Bioconjug. Chem.* 6: 705–708 (1995)) to extend the circulation lifetime in vivo. Hydrophilic polymers for coating or derivation of the liposomes include polyethylene glycol, polyvinylpyrrolidone, polyvinylmethyl ether, polyaspartamide, hydroxymethyl cellulose, hydroxyethyl cellulose, and the like. In addition, as described above, attaching proteins that bind a cell surface protein which is endocytosed, e.g., capsid proteins or fragments thereof tropic for a particular cell types and antibodies for cell surface proteins which undergo internalization (see Wu et al, supra; Wagner et al., supra), may be used for targeting and/or facilitating uptake of the liposomes to specific cells or tissues.

Liposomes are prepared by ways well known in the art (see for example, Szoka, F. et al. *Ann. Rev. Biophys. Bioeng.* 9: 467–508 (1980)). One typical method is the lipid film hydration technique in which lipid components are mixed in an organic solvent followed by evaporation of the solvent to generate a lipid film. Hydration of the film in aqueous buffer solution, preferably containing the subject peptide or nucleic acid, results in an emulsion, which is sonicated or extruded to reduce the size and polydispersity. Other methods include reverse-phase evaporation (see Pidgeon, C. et al. *Biochemistry* 26: 17–29 (1987); Duzgunes, N. et al. *Biochim. Biophys. Acta.* 732: 289–99 (1983)), freezing and thawing of phospholipid mixtures, and ether infusion.

In another preferred embodiment, the carriers are in the form of microparticles, microcapsules, micropheres and nanoparticles, which may be biodegradable or non-biodegradable (see for example, *Microencapsulates: Methods and Industrial Applications*, Drugs and Phamaceutical Sciences, Vol 73, Benita, S. ed, Marcel Dekker Inc., New York, 1996; incorporated by reference). As used herein, microparticles, microspheres, microcapsules and nanoparticles mean a particle, which is typically a solid, containing the substance to be delivered. The substance is within the core of the particle or attached to the particle's polymer network. Generally, the difference between microparticles (or microcapsules or microspheres) and nanoparticles is one of size. As used herein, microparticles have a particle size range of about 1 to about >1000 microns. Nanoparticles have a particle size range of about 10 to about 1000 nm.

A variety of materials are useful for making microparticles. Non-biodegradable microcapsules and microparticles include, but not limited to, those made of polysulfones, poly(acrylonitrile-co-vinyl chloride), ethylene-vinyl acetate, hydroxyethylmethacrylate-methyl-methacrylate copolymers. These are useful for implantation purposes where the encapsulated peptide diffuses out from the capsules. In another aspect, the microcapsules and microparticles are based on biodegradable polymers, preferably those that display low toxicity and are well tolerated by the immune system. These include protein based microcapsulates and microparticles made from fibrin, casein, serum albumin, collagen, gelatin, lecithin, chitosan, alginate or poly-amino acids such as poly-lysine. Biodegradable synthetic polymers for encapsulating may comprise polymers such as polylactide (PLA), polyglycolide (PGA), poly(lactide-co-glycolide) (PLGA), poly(caprolactone), polydioxanone trimethylene carbonate, polyhybroxyalkonates (e.g., poly($\beta$-hydroxybutyrate)), poly($\gamma$-ethyl glutamate), poly(DTH iminocarbony (bisphenol A iminocarbonate), poly (ortho ester), and polycyanoacrylate. Various methods for making microparticles containing the subject compositions are well known in the art, including solvent removal process (see for example, U.S. Pat. No. 4,389,330); emulsification and evaporation (Maysinger, D. et al. *Exp. Neuro.* 141: 47–56 (1996); Jeffrey, H. et al. *Pharm. Res.* 10: 362–68 (1993)), spray drying and extrusion methods.

Another type of carrier is nanoparticles, which are generally suitable for intravenous administrations. Submicron and nanoparticles are generally made from amphiphilic diblock, triblock, or multiblock copolymers as is known in the art. Polymers useful in forming nanoparticles include, but are limited to, poly(lactic acid) (PLA; see Zambaux et al., *J. Control Release* 60: 179–188 (1999)), poly(lactide-co-glycolide), blends of poly(lactide-co-glycolide) and polycarprolactone, diblock polymer poly(l-leucine-block-l-glutamate), diblock and triblock poly(lactic acid) (PLA) and poly(ethylene oxide) (PEO) (see De Jaeghere, F. et al., *Pharm. Dev. Technol.*; 5: 473–83 (2000)), acrylates, arylamides, polystyrene, and the like. As described for microparticles, nanoparticles may be non-biodegradable or biodegradeable. Nanoparticles may be also be made from poly(alkylcyanoacrylate), for example poly(butylcyanoacrylate), in which the peptide is absorbed onto the nanoparticles and coated with surfactants (e.g., polysorbate 80). Methods for making nanoparticles are similar to those for making microparticles and include, among others, emulsion polymerization in continuous aqueous phase, emulsification-evaporation, solvent displacement, and emulsification-diffusion techniques (see Kreuter, J. *Nano-particle Preparation and Applications*, In Microcapsules and nanoparticles in medicine and pharmacy," (M. Donbrow, ed.), pg. 125–148, CRC Press, Boca Rotan, Fla., 1991; incorporated by reference).

Hydrogels are also useful in delivering the subject agents into a host. Generally, hydrogels are crosslinked, hydrophilic polymer networks permeable to a wide variety of drug compounds, including peptides. Hydrogels have the advantage of selective trigger of polymer swelling, which results in controlled release of the entrapped drug compound. Depending on the composition of the polymer network, swelling and subsequent release may be triggered by a variety of stimuli, including pH, ionic strength, thermal, electrical, ultrasound, and enzyme activities. Non-limiting examples of polymers useful in hydrogel compositions include, among others, those formed from polymers of poly(lactide-co-glycolide), poly(N-isopropylacrylamide); poly(methacrylic acid-g-polyethylene glycol); polyacrylic acid and poly(oxypropylene-co-oxyethylene) glycol; and natural compounds such as chrondroitan sulfate, chitosan, gelatin, or mixtures of synthetic and natural polymers, for example chitosan-poly(ethylene oxide). The polymers are crosslinked reversibly or irreversibly to form gels embedded with the oligopeptides of the present invention (see for example, U.S. Pat. Nos. 6,451,346; 6,410,645; 6,432,440; 6,395,299; 6,361,797; 6,333,194; 6,297,337 Johnson, O. et al., *Nature Med.* 2: 795 (1996); incorporated by reference in their entirety).

In one preferred embodiment, the gel polymers are acrylic acid polymers, preferably carbomers (e.g., carboxypolymethylene), such as Carbopol (e.g., Carbopol 420–430, 475, 488, 493, 910, 934P, 974P, and the like; Brock et al., *Pharmacotherapy* 14: 430–437 (1994)), which are non-linear polymers of acrylic acid crosslinked with polyalkenyl polyether. Others types of carbomers include acrylic acids crosslinked with polyfunctional compounds, such as polyallysucrose. In addition to the advantage of hydrating and swelling to a gel, which entraps the subject compounds and limits their release, carbomer gels are mucoadhesive. The polymers adheres to the intestinal mucosal membrane, thus resulting in local delivery of the peptides (see Hutton et al. *Clin. Sci.* 78: 265–271 (1990); Pullan et al., *Gut* 34: 676–679 (1993), hereby incorporated by reference). In addition, these polymers have the added advantage of limiting intestinal protease activity.

The concentrations of the peptides or nucleic acid encoding therefore and the anti-retroviral agents will be determined empirically in accordance with conventional procedures for the particular purpose. Generally, for administering the peptides and anti-retroviral agents ex vivo or in vivo for therapeutic purposes, the subject formulations are given at a pharmacologically effective dose. By "pharmacologically effective amount" or "pharmacologically effective dose" is an amount sufficient to produce the desired physiological effect or amount capable of achieving the desired result, particularly for treating the disorder or disease condition, including reducing or eliminating one or more symptoms of the disorder or disease.

The amount administered to the host will vary depending upon what is being administered, the purpose of the administration, such as prophylaxis or therapy, the state of the host, the manner of administration, the number of administrations, interval between administrations, and the like. These can be determined empirically by those skilled in the art and may be adjusted for the extent of the therapeutic response. Factors to consider in determining an appropriate dose include, but is not limited to, size and weight of the subject, the age and sex of the subject, the severity of the symptom, the stage of the disease, method of delivery of the agent, half-life of the agents, and efficacy of the agents. Stage of the disease to consider include whether the disease is acute or chronic, relapsing or remitting phase, and the progressiveness of the disease. Determining the dosages and times of administration for a therapeutically effective amount are well within the skill of the ordinary person in the art.

For any compounds used in the present invention, therapeutically effective dose is readily determined by methods well known in the art. For example, an initial effective dose can be estimated initially from cell culture assays. An indicator of HIV infection and/or inflammatory response or may be used, such as viral replication, presence of viral expression products, expression levels of pro-inflammatory cytokines, or inhibition of CTL activity. A dose can then be formulated in animal models to generate a circulating concentration or tissue concentration, including that of the $IC_{50}$ (i.e., dose lethal to about 50% of cells in the cell culture) as determined by the cell culture assays.

In addition, the toxicity and therapeutic efficacy are generally determined by cell culture assays and/or experimental animals, typically by determining a $LD_{50}$ (lethal dose to 50% of the test population) and $ED_{50}$ (therapeutically effectiveness in 50% of the test population). The dose ratio of toxicity and therapeutic effectiveness is the therapeutic index. Preferred are compositions, individually or in combination, exhibiting high therapeutic indices. Determination of the effective amount is well within the skill of those in the art, particularly given the detailed disclosure provided herein.

Generally, in the case where a formulations are administered directly to a host, the present invention provides for a bolus or infusion of the subject composition that will administered in the range of about 0.1–50, more usually from about 1–25 mg/kg body weight of host. The amount will generally be adjusted depending upon the half-life of the peptide and anti-retroviral agent, where the half life will generally be at least one minute, more usually at least about 10 min, desirably in the range of about 10 min to 12 h. Short half-lives are acceptable, so long as efficacy can be achieved with individual dosages, continuous infusion, or repetitive dosages. Formulations for administration may be presented in unit a dosage form, e.g., in ampules, capsules, pills, or in multidose containers or injectables.

Dosages in the lower portion of the range and even lower dosages may be employed, where the peptide has an enhanced half-life or is provided as a depot, such as a slow release composition comprising particles, a polymer matrix which maintains the peptide over an extended period of time (e.g., a collagen matrix, carbomer, etc.), use of a pump which continuously infuses the peptide over an extended period of time with a substantially continuous rate, or the like. The host or subject may be any mammal including domestic animals, pets, laboratory animals, primates, particularly humans subjects.

In addition to administering the subject peptide compositions directly to a cell culture in vitro, to particular cells ex vivo, or to a mammalian host in vivo, nucleic acid molecules (DNA or RNA) encoding the subject peptides may also be administered thereto, thereby providing an effective source of the subject peptides for the application desired. As described above, nucleic acid molecules encoding the subject peptides may be cloned into any of a number of well known expression plasmids (see Sambrook et al., supra) and/or viral vectors, preferably adenoviral or retroviral vectors (see for example, Jacobs et al., *J. Virol.* 66:2086–2095 (1992), Lowenstein, Bio/Technology and Biotechniques 12:1075–1079 (1994) and Berkner, Biotechniques 6:616–624 (1988)), under the transcriptional regulation of control sequences which function to promote expression of the nucleic acid in the appropriate environment. Such nucleic acid-based vehicles may be administered directly to the cells or tissues ex vivo (e.g., ex vivo viral infection of cells for transplant of peptide producing cells) or to a desired site in vivo, e.g. by injection, catheter, orally (e.g., hybrogels), and the like, or, in the case of viral-based vectors, by systemic administration. Tissue specific promoters may optionally be employed, assuring that the peptide of interest is expressed only in a particular tissue or cell type of choice. Methods for recombinantly preparing such nucleic acid-based vehicles are well known in the art, as are techniques for administering nucleic acid-based vehicles for peptide production.

For the purposes of this invention, the methods of administration is chosen depending on the condition being treated, the form of the subject compositions, and the pharmaceutical composition. Administration of the oligopeptides and anti-retroviral agents can be done in a variety of ways, including, but not limited to, cutaneously, subcutaneously, intravenously, orally, topically, transdermally, intraperitoneally, intramuscularly, nasally, and rectally (e.g., colonic administration). For example, microparticle, microsphere, and microencapsulate formulations are useful for oral, intramuscular, or subcutaneous administrations. Liposomes and nanoparticles are additionally suitable for intravenous administrations. Administration of the pharmaceutical compositions may be through a single route or concurrently by several routes. For instance, oral administration can be accompanied by rectal or topical administration to the affected area. Alternatively, oral administration is used in conjunction with intravenous or parenteral injections.

In one preferred embodiment, the method of administration is by oral delivery, in the form of a powder, tablet, pill, or capsule. Pharmaceutical formulations for oral administration may be made by combining one or more peptide and anti-retroviral agent with suitable excipients, such as sugars (e.g., lactose, sucrose, mannitol, or sorbitol), cellulose (e.g., starch, methyl cellulose, hydroxylmethyl cellulose, carbonxymethyl cellulose, etc.), gelatin, glycine, saccharin, magnesium carbonate, calcium carbonate, polymers such as polyethylene glycol or polyvinylpyrrolidone, and the like. The pills, tablets, or capsules may have an enteric coating, which remains intact in the stomach but dissolves in the intestine. Various enteric coating are known in the art, a number of which are commercially available, including, but not limited to, methacrylic acid-methacrylic acid ester copolymers, polymer cellulose ether, cellulose acetate phathalate, polyvinyl acetate phthalate, hydroxypropyl methyl cellulose phthalate, and the like. Alternatively, oral formulations of the peptides are in prepared in a suitable diluent. Suitable diluents include various liquid form (e.g., syrups, slurries, suspensions, etc.) in aqueous diluents such as water, saline, phosphate buffered saline, aqueous ethanol, solutions of sugars (e.g. sucrose, mannitol, or sorbitol), glycerol, aqueous suspensions of gelatin, methyl cellulose, hydroxylmethyl cellulose, cyclodextrins, and the like. As used herein, diluent or aqueous solutions also include infant formula, given that various forms of colitis can affect infants and children. In some embodiments, lipohilic solvents are used, including oils, for instance vegetable oils, peanut oil, sesame oil, olive oil, corn oil, safflower oil, soybean oil, etc.); fatty acid esters, such as oleates, triglycerides, etc.; cholesterol derivatives, including cholesterol oleate, cholesterol linoleate, cholesterol myristilate, etc.; liposomes; and the like.

In another preferred embodiment, administration is done rectally. This may use formulations suitable for topical application in the form of salves, tinctures, cremes, or for application into the lumen of the intestine by use of compositions in the form of suppositories, enemas, foams, etc. Suppositories may contain conventional suppository bases such as cocoa butter, carbowaxes, polyethylene glycols, or glycerides, which are solid or semi-solid at room temperature but liquid at body temperature.

In yet another preferred embodiment, the administration is carried out cutaneously, subcutaneously, intraperitonealy, intramuscularly and intravenously. As discussed above, these are in the form of peptides and anti-retroviral agents dissolved or suspended in suitable aqueous medium, as discussed above. Additionally, the pharmaceutical compositions for injection may be prepared in lipophilic solvents, which include, but is not limited to, oils, such as vegetable oils, olive oil, peanut oil, palm oil soybean oil, safflower oil, etc; synthetic fatty acid esters, such as ethyl oleate or triglycerides; cholesterol derivatives, including cholesterol oleate, cholesterol linoleate, cholesterol myristilate, etc.; or liposomes, as described above. The compositions may be prepared directly in the lipophilic solvent or preferably, as oil/water emulsions, (see for example, Liu, F. et al. *Pharm. Res.* 12: 1060–1064 (1995); Prankerd, R. J. *J. Parent. Sci. Tech.* 44:139–49 (1990); U.S. Pat. No. 5,651,991).

The delivery systems also include sustained release or long term delivery methods, which are well known to those skilled in the art. By "sustained release or" "long term release" as used herein is meant that the delivery system administers a pharmaceutically therapeutic amount of subject compounds for more than a day, preferably more than a week, and most preferable at least about 30 days to 60 days, or longer. Long term release systems may comprise implantable solids or gels containing the subject peptide, such as biodegradable polymers described above; pumps, including peristaltic pumps and fluorocarbon propellant pumps; osmotic and mini-osmotic pumps; and the like. Peristaltic pumps deliver a set amount of drug with each activation of the pump, and the reservoir can be refilled, preferably percutaneously through a port. A controller sets the dosage and can also provides a readout on dosage delivered, dosage remaining, and frequency of delivery. Fluorocarbon propellant pumps utilize a fluorocarbon liquid to operate the pump. The fluorocarbon liquid exerts a vapor pressure above atmospheric pressure and compresses a chamber containing the drug to release the drug. Osmotic pumps (and mini-osmotic pumps) utilize osmotic pressure to release the drug at a constant rate. The drug is contained in an impermeable diaphragm, which is surrounded by the osmotic agent. A semipermeable membrane contains the osmotic agent, and the entire pump is housed in a casing. Diffusion of water through the semipermeable membrane squeezes the diaphragm holding the drug, forcing the drug into bloodstream, organ, or tissue. These and other such implants are particularly useful in treating a inflammatory disease condition, especially those manifesting recurring episodes or which are progressive in nature, by delivering the oligopeptides of the invention via systemic (e.g., intravenous or subcutaneous) or localized doses in a sustained, long term manner.

The present invention also encompasses the therapeutic combinations disclosed herein in the form of a kit or packaged formulation. A kit or packaged formulation as used herein includes one or more dosages of an immunomodulating peptide, and salts thereof, and at least one anti-retroviral agent, in a container holding the dosages together with instructions for simultaneous or sequential administration to an HIV-infected patient. For example, the package may contain the peptides along with a pharmaceutical carrier combined in the form of a powder for mixing in an aqueous solution, which can be ingested by the afflicted subject. Another example of packaged drug is a preloaded pressure syringe, so that the compositions may be delivered colonically. The package or kit includes appropriate instructions, which encompasses diagrams, recordings (e.g., audio, video, compact disc), and computer programs providing directions for use of the combination therpy.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching.

All publications and patent applications mentioned in this specification are herein incorporated by reference to the same extent as if each individual publication or patent application was specifically and individually indicated to be incorporated by reference.

EXPERIMENTAL

As disclosed in U.S. patent applications U.S. Ser. No. 08/838,916 and U.S. Ser. No. 09/028,083 and in the relevant literature, including Grassy et al., parameters were defined based on known oligopeptides that had previously been found to have properties of inhibiting T cell activity (see, e.g., Buelow et al., supra). The conformational space necessary for immunosuppressive activity was computed according to the procedure described by Yasri et al., supra. Using these parameters (see Table I), which define compounds having known T cell inhibitory activity, new cytomodulating peptides were devised and tested, and were found to have activity equal to or surpassing known active compounds. The computer program used to predict and to devise the immunosuppressive activity of peptides and pseudopeptides was developed as follows:

1. Methodology

On the basis of an initial experimental data set made of peptides showing or not showing immunosuppressive activity, there was deduced:

i. A consensus sequence containing the amino acids required for the activity and allowing the development of new peptides or pseudopeptide libraries;

ii. A set of physicochemical and topological properties involved in the activity and converted into a set of constraints by the variable mapping technique (Grassy et al., *J. of Molecular Graphics* 13: 356–367 (1995)).

2. Variable Mapping

The method is based on physicochemical and conformational constraints, as deduced from the results of a training set of data.

Physicochemical Constraints

The method requires the determination of physicochemical constraints defined as ranges of properties for said biological activity. The computational method used for the determination of the set of constraints is named Variable Mapping and is described below.

The Variable Mapping Approach

This qualitative technique consists of an evaluation of the distribution (global or percent wise) of the active and inactive molecules as a function of the values of given parameters. The superposition of all graphs (activity-property) exhibits, for certain parameters, to the limiting values (low and/or higher) which are necessary for leading to an active compound. This graphical method gives a diagnosis of the qualitative non-linear dependencies between the activity and a molecular property. Regarding those properties involved in receptor ligand interactions, it has been clearly established that the existence of strict contingencies determining the adaptability to the receptor imply an embedding of certain structural and physicochemical properties. This method results in simple rules which can be used to predict the activity of unknown products. A graphical representation showing the number of successes relative to the number of violations of the rules allows one to compare the distributions with the activities for the whole set of molecules under study.

3. Physicochemical and Topological Parameters Used in the Definition of the Constraints Involved in the Immunosuppressive Activity of Peptides and Pseudopeptides.

Lipophilicity

Lipophilicity of peptides expressed as log P (where P is the partition coefficient of a named peptide between water and n-octanol). Molecular log P values can be computed by TSAR 2.31 using the atomic incremental logP values determined by Ghose et al., *J. Chem. Inf. Comput.* 29:163 (1989). As demonstrated by the analysis of the initial data set, the lipophilicity of an immunosuppressive peptide must be $\geqq -6.85$

Topological Indices

Balaban Index (Balaban, Chem. Phys. 89:399 (1982)):

The Balaban index computed for a connected molecular graph (H suppressed) is calculated as follows:

$$\frac{M}{\mu+1}\Sigma(D_i D_j)^{-0.5}$$

where M is the number of edges in the graph, μ is the cyclomatic number of the graph, i.e., the minimum number of edges which must be removed before G becomes acyclic, and $D_i = \Sigma D_{ij}$ (with j=1) is a distance matrix of the shortest path between the two vertices.

Molecular Volume:

The molecular volume is computed assuming standard Van der Waals radii for each element. This calculation is done on the extended conformation of the peptide.

Ellipsoidal Volume:

This volume is computed after determination of the three components of the inertia momentum of the molecule, assuming mean atomic masses for constituent atoms. This calculation is done on the extended conformation of the peptide.

Molar Refractivity:

Molar refractivity is computed using the atomic molar refractivity values determined by Ghose et al., supra.

Dipole Moment:

This parameter is computed on the extended conformation of the peptides. The total dipole moment for a molecule is expressed in Debye units:

$$\mu = e \Sigma r_i q_i$$

where $r_i$ is the distance of an atom i to the origin, $q_i$ is the charge of the atom i. The charges on the atoms are computed using the Charge-2 method. (Abraham and Smith., *J. Comput. Aided Mol. Design* 3: 175–187 (1989))

Kier Chir V 4:

This index is one of the connectivity indexes developed by L. B. Kier. The Kier Chi V 4 computes in several steps (H included).
a. Determination and numbering of all the paths of length 4 on the molecular graph of the peptide.
b. Computation of each path of length 4 of the following quantities:

$$c_s^v = \Pi[(\partial_j^v)]^{-0.5}$$

for j=1,4, where $\delta_i = Z_i - h_i$ is defined for an atom as the difference between the total number of valence electrons $Z_i$ and the number $h_i$ of hydrogen atoms bonded to the atom i.
c. Summation of all these values concerning the entire set of subgraphs of length 4 on the graph $$X = \Sigma(c_v^s)$$

Kier Kappa Alpha:
Kier Kappa Alpha 1 ($K\alpha^1$)

If A is the total number of atoms of the molecule (H included), $K\alpha^1$ is equal to:

$$\frac{(A + \alpha)(A + \alpha - 1)^2}{(P_1 + \alpha)^2} \quad \text{with:}$$

$$\alpha_i = \frac{r_i}{rC_{sp}^3} - 1$$

$r_i$ is the covalent radius of the atom i and $rC_{sp}^3$ the covalent radius of a carbon $sp^3$, $P_1$ is the total number of paths of length=1 along the molecular graph of the peptide under study.

Kier Kappa Alpha 2 ($K\alpha^2$)

If A is the total number of atoms of the molecule (H included), $K\alpha^2$ is equal to:

$$\frac{(A + \alpha - 1)(A + \alpha - 2)^2}{(P_2 + \alpha)^2} \quad \text{with:}$$

$$\alpha_i = \frac{r_i}{rC_{sp}^3} - 1$$

$r_i$ is the covalent radius of the atom i and $rC_{sp}^3$ the covalent radius of a carbon $sp^3$, $P_2$ is the total number of paths of length=2 along the molecular graph of the peptide under study.

Flexibility Phi:

Based upon the above formulas, the flexibility of a molecule can be defined as:

$$Phi = (K\alpha^1)(K\alpha^2)/A$$

where A is the total number of atoms (H included).

Atoms and Groups Counts:

The number of the following atom types was also used as a constraint:
Total number of oxygen atoms of the peptide
Total number of nitrogen atoms of the peptide The number of the following groups was also used as a constraint:
Total number of ethyl groups
Total number of hydroxyl groups 4. Values of the Constraints Generation of Peptide or Pseudopeptide Libraries Starting from the consensus sequence Arg-X-X-X-Arg-X-X-X-X-Tyr where X is an amino acid which is as defined above and in the earlier analogous formula, the physicochemical and topological parameters previously described were computed and whether these parameters were within the constraints defined by the initial training set. For example, starting from X=Leu, nLeu, Trp, Tyr, Gly or Val, a library of 279,936 molecules was generated and only 26 of them satisfied the required constraints.

The ranges of properties necessary to obtain a biological activity are summarized in the following Table I.

Table I

TABLE I

| Value ranges of physicochemical and structural parameters | | |
|---|---|---|
| Property | Minimum | Maximum |
| LogP | −6.849 | −0.004 |
| Ellipsoidal Volume (Å$^3$) | 5785.5 | 29460.00 |
| Molecular Volume (Å$^3$) | 660.9 | 1050.4 |
| Molar refractivity | 221.30 | 359.3 |
| Kier Chi V4 | 3.325 | 5.342 |
| Kappa a$_2$ | 26.120 | 44.31 |
| Flexibility | 22.50 | 40.3 |
| Balaban Index | 2.846 | 6.701 |
| Total Dipole | 3.423 | 80.79 |
| Number of oxygen atoms | 10 | 15 |
| Number of nitrogen atoms | 8 | 20 |
| Number of ethyl groups | 0 | 1 |
| Number of hydroxyl groups | 1 | 3 |

5. Characterization of the Conformational Space Involved in the Immunosuppressive Activity of Peptides and Pseudopeptides.

Spatial Autocorrelation Vector of a 3D Structure:

The concept of autocorrelation description of a molecular structure was first introduced by Broto et al., *Eur. J. Med. Chem.* 19:66–70 (1984). This vector basically represents the discretized distance distribution derived from the interatomic distance matrix of a molecule. The first component of this vector ($A_o$) is equal to the number of atoms of the structures, the other components, $A_1 \ldots A_n$, are defined by the number of atom pairs which are separated by a distance within the range defined by a lower limit $(n-1)D_i$, where n is the order of the bin of the vector and $D_i$ the distance increment. Similarly, it is possible to calculate the distribution of an atomic property P. In this case, the weighted autocorrelation component $AP_n$ is obtained by the sum of the products of property values P on atoms i,j, having an interdistance belonging to the distance interval $[(n-1)D_i, nD_i]$. The number of components of the vector is then defined by $n_{max}=(D_{max}/D_i)+1$, where $D_{max}$ is the greatest interatomic distance in the structure.

The autocorrelation vector exhibits some useful features:
- This vector achieves a substantial reduction of conformational data. An entire conformation is described by a limited set of n numerical values.
- The vector is very easy to calculate on the basis of 3D coordinate data. Therefore, it is possible to compute and store this vector during molecular dynamics simulations, the reduction of the size of the storage involved in such a process, in comparison to the classical storage of a set of complete distance matrices, allows much longer simulations than usual.
- The autocorrelation vector of a conformation is transitionally and rotationally invariant and is also independent of the atomic numbering of the molecule.
- This vector is sensitive both to minor and major changes in conformation: the more the conformation is changed, the more the components of the vector are modified. The sensitivity depends on the distance increment chosen for calculations, but an increment from 0.5 Å or 1 Å (small molecules) to 5 Å (macromolecules) is a good choice for the usual simulations (Yasri et al., *Protein Engineering* 11:959–976 (1996)).

It is possible to analyze only a part of a structure or only a specific subset of atoms of this structure, e.g. $C_a$ in proteins, N atoms, heavy atoms, etc. The vector is entirely defined by the knowledge of a structure, so that the comparison of different structures can be performed, using this vector without any reference.

Molecular Dynamics Analysis Using 3-D Autocorrelation Vectors

Applied to HLA-B2702.75-84 peptide (amino acid sequence Arg-Glu-Asn-Leu-Arg-Ile-Ala-Leu-Arg-Tyr (SEQ ID NO:35)) and on various active and inactive derivative peptides thereof, molecular dynamics simulations were performed using AMBER 4.1. The simulation of one nanosecond of dynamics generate a set of $10^3$ conformations (one conformation per picosecond). For each conformation the 3D autocorrelation vector was calculated using TSAR with a distance increment of 1 Å and the entire set of conformations was stored as 3D autocorrelation vectors versus time matrix ($10^3$xn).

The aim of the work was to define the conformational space responsible for immunosuppressive activity, by comparison of the conformational spaces of active and inactive peptides using the methodology explained in the references cited in the Relevant Literature.

6. Statistical Analysis

Cluster Analysis

In order to compare different conformations, the distance matrix between all of these conformations in the hyperspace defined by the components of their unweighted 3D autocorrelation vectors was determined. The more the structure of two compounds are analogous, the shorter their distance. This method provides a quantification of the rigid molecular fit. Using the starting conformation as a reference, the numerical value of this distance is analogous to a root-mean-square deviation.

Principal Component Analysis (PCA)

PCA is a multidimensional statistical method for data analysis, suited for representing molecules in the hyperspace of their properties (molecular descriptors). PCA can be used to reduce a large number of descriptors to a smaller number of synthetic orthogonal variables issued from a linear combination of the original descriptors. This method retains the largest part of the total initial information. The original variables were normalized and the diagonalization of the covariance matrix was calculated using the classical Jacobi transform routine. The components of the 3K autocorrelogram vector provide a good description of the 3K structure of different conformations, but are awkward to handle because they contain too many data to get an easy visualization. PCA can reduce the dimensionality of the data to a 2D or 3D representation that contains as much of the original information as possible. Using PCA, the immunosuppressive peptides exhibit a well defined common conformational space. All the peptides able to reach these conformational specifications can exhibit an immunosuppressive activity.

Conformational Space Coordinates of Peptide bc 1nL Bioactive Conformation

FIG. 1 shows the two-dimensional conformational space and related conformations of peptide bc1 nL (RDP58), wherein the bc1 nL peptide has the amino acid sequence Arg-nL-nL-nL-Arg-nL-nL-nL-Gly-Tyr (SEQ ID NO:1) and wherein "nL" is norleucine (see below). The structures drawn were obtained by applying cluster analysis method on the whole trajectory of peptide bc1 nL.

Main Conformations of Peptide bc 1nL

Structural properties of the main visited conformations of bc 1nL (FIG. 1, (1), (2), (3), (4) and (5)) in its conformational space are summarized in Table II. These properties concern the coordinates in the three dimensional space defined by the three first principal components (PCA coordinates), and the radius of gyration (Rg).

TABLE II

Spatial coordinates (PCA coordinates) and radius of gyration (Rg) of dynamic conformations of peptide bc 1nL.

| Conformations | PCA Coordinates | | | Rg |
|---|---|---|---|---|
| | PC1 | PC2 | PC3 | |
| (1) | 0.785 | −2.816 | −0.531 | 9.92 |
| (2) | 0.382 | −0.899 | −0.164 | 7.99 |
| (3) | −0.811 | 0.345 | −0.481 | 6.93 |
| (4) | 0.741 | 0.950 | −1.092 | 6.76 |
| (5) | −2.096 | −0.296 | 0.770 | 6.67 |

Conformational Space of Active Peptides

Figure 2:
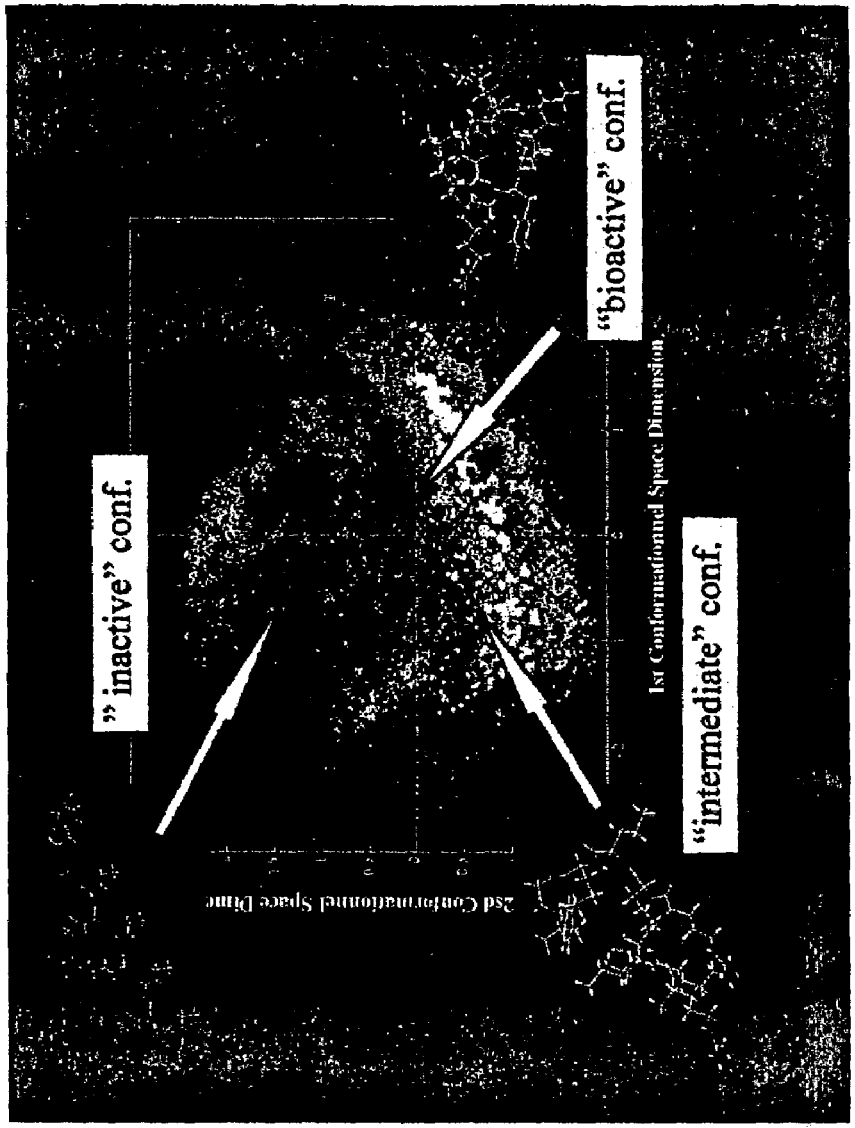
FIG. 2 is a depiction of a projection of peptide trajectories into the principal plan of D2 peptide reference trajectory.

The trajectory of the D2 (amino acid sequence Arg-Val-Asn-Leu-Arg-Ile-Ala-Leu-Arg-Tyr (SEQ ID NO:9)) peptide has been described by the 3-D autocorrelation method and the data analyzed by principal component analysis. This provided a principal plan defined by the 2 first principal components which contain all the conformations visited during the trajectory. The D2 peptide trajectory was used as a trajectory reference and all the trajectories calculated were projected into its principal plan. (FIG. 2).

The immunosuppressive peptides exhibit a well defined common conformational space featuring the following points: PCA dimensions:
PC1:minimum=−2.0; maximum=2.0
PC2:minimum=−2.0; maximum=1.0
PC3:minimum=−1.0; maximum=1.0

The following peptides, defined as bc peptides, were prepared as compositions:

| bc # |     |     |     |     |     |     |     |     |     |     | SEQ ID NO: |
|------|-----|-----|-----|-----|-----|-----|-----|-----|-----|-----|------------|
| 1    | Arg | Leu | Leu | Leu | Arg | Leu | Leu | Leu | Gly | Tyr | 10 |
| 2    | Arg | Val | Leu | Leu | Arg | Leu | Leu | Leu | Gly | Tyr | 11 |
| 3    | Arg | Ile | Leu | Leu | Arg | Leu | Leu | Leu | Gly | Tyr | 12 |
| 4    | Arg | Leu | Val | Leu | Arg | Leu | Leu | Leu | Gly | Tyr | 13 |
| 5    | Arg | Leu | Ile | Leu | Arg | Leu | Leu | Leu | Gly | Tyr | 14 |
| 6    | Arg | Leu | Leu | Val | Arg | Leu | Leu | Leu | Gly | Tyr | 15 |
| 7    | Arg | Leu | Leu | Ile | Arg | Leu | Leu | Leu | Gly | Tyr | 16 |
| 8    | Arg | Leu | Leu | Leu | Arg | Val | Leu | Leu | Gly | Tyr | 17 |
| 9    | Arg | Leu | Leu | Leu | Arg | Ile | Leu | Leu | Gly | Tyr | 18 |
| 10   | Arg | Leu | Leu | Leu | Arg | Leu | Val | Leu | Gly | Tyr | 19 |
| 11   | Arg | Leu | Leu | Leu | Arg | Leu | Ile | Leu | Gly | Tyr | 20 |
| 12   | Arg | Leu | Leu | Leu | Arg | Leu | Leu | Val | Gly | Tyr | 21 |
| 13   | Arg | Leu | Leu | Leu | Arg | Leu | Leu | Ile | Gly | Tyr | 22 |
| 14   | Arg | Trp | Leu | Leu | Arg | Leu | Leu | Leu | Gly | Tyr | 23 |
| 15   | Arg | Leu | Trp | Leu | Arg | Leu | Leu | Leu | Gly | Tyr | 24 |
| 16   | Arg | Leu | Leu | Trp | Arg | Leu | Leu | Leu | Gly | Tyr | 25 |
| 17   | Arg | Leu | Leu | Leu | Arg | Trp | Leu | Leu | Gly | Tyr | 26 |
| 18   | Arg | Leu | Leu | Leu | Arg | Leu | Trp | Leu | Gly | Tyr | 27 |
| 19   | Arg | Leu | Leu | Leu | Arg | Leu | Leu | Trp | Gly | Tyr | 28 |
| 20   | Arg | Tyr | Leu | Leu | Arg | Leu | Leu | Leu | Gly | Tyr | 29 |
| 21   | Arg | Leu | Tyr | Leu | Arg | Leu | Leu | Leu | Gly | Tyr | 30 |
| 22   | Arg | Leu | Leu | Tyr | Arg | Leu | Leu | Leu | Gly | Tyr | 31 |
| 23   | Arg | Leu | Leu | Leu | Arg | Tyr | Leu | Leu | Gly | Tyr | 32 |
| 24   | Arg | Leu | Leu | Leu | Arg | Leu | Tyr | Leu | Gly | Tyr | 33 |
| 25   | Arg | Leu | Leu | Leu | Arg | Leu | Leu | Tyr | Gly | Tyr | 32 |
| 1nL  | Arg | nL  | nL  | nL  | Arg | nL  | nL  | nL  | Gly | Tyr | 1  | nL = norleucine

EXAMPLE

Effect of bc-1nL Peptide (RDP58) On Clinical Outcome of SIV Infection

Animals

Fifteen (15) colony bred rhesus macaques (*Macaca mulatta*) from the California Regional Primate Research Center, Davis, were used in this study. Animals were housed in accordance with The American Association for Accreditation of Laboratory Animal Care guidelines. All animals were seronegative for simian retrovirus (SRV-1) and simian T cell leukemia virus type-1 (STLV-1). Rhesus macaques were intravenously (I.V.) infected with 100 animal infectious doses of uncloned pathogenic SIVmac251. This viral inoculum has been previously shown to cause persistent viremia and infection Of multiple tissues in vivo, leading to fatal AIDS-like disease (Mandell et al 1995). The animals were divided into the following groups
1. Untreated Controls, necropsy at week 10 (n=3)
2. Untreated Controls, necropsy at week 26 (n=3)
3 PMPA treatment, necropsy at week 10 (n=3)
4. PMPA+RDP58 treatment, necropsy at week 10 (n=3)
5. PMPA treatment, necropsy at week 26 (n=3)
6. PMPA+RDP58 treatment, necropsy at week 26 (n=3)

PMPA treatment was initiated at 6 weeks post-infection and was administered at 30 mg/kg, I.V. RDP58 was administered orally, dissolved in drinking water, at 2 mg/kg, 3×/week.

Jejunal biopsies and peripheral blood samples were obtained from all animals prior to infection and at 2 weeks, 6 weeks, 10 weeks, 16 weeks and 26 weeks post-infection and at necropsy. Jejunal biopsies was obtained using a pediatric gastroscope.

Viral Load Determination.

Primers and probes specific to the SIV RNA sequence were designed and used in the real time PCR reaction. Probes were tagged with a fluorescent dye (FAM) at the 5' end and a quencher dye at the 3' end. The reaction is carried out using One tube RT-PCR master mix (PE Applied Biosystems) on the ABI Prism 7700 sequence detector (PE Applied Biosystems). The progress of the reaction is monitored through the fluorescence released by displaced primers that is proportional to the product being formed. Thus the fluorescence intensity is directly related to the amount of input target RNA. The data was analyzed with Sequence Detector Software (SDS). This allowed the computation of copy numbers using CT values obtained from the reaction and comparing them against the standard curve of known copy numbers.

Cell Isolation and Flow Cytometry

Jejunal pinch biopsy samples were incubated RPMI 1640 (Gibco) and collagenase (Sigma) at 37° C. and rapidly shaken for 45 minutes then subjected to Percoll (Sigma) density gradient centrifugation to enrich for T cells and eliminate tissue debris. Cells were then washed with PBS (Gibco) and allowed to equilibrate over night at 37° C. and 5% $CO_2$ in complete RPMI 1640 (containing 10% fetal calf sera, penicillin and streptomyicin). Cells were stained for three-color flow cytometric analysis with CD3FITC, CD4PE, CD8PE, CD45RA (BD Pharmingen), CD8TC, CD69TC, CD28TC, CD25PE (Caltag). All cells were fixed in 1% paraformaldehyde in PBS and read on a Bectin Dickenson FacScan within 3 hours of staining. Flow data was analyzed using Bectin Dickenson CellQuest softwear.

TUNEL Assay

A variation of the TUNEL (TdT-mediated dUTP nick end-labeling) assay was performed on paraffin-embedded intestinal sections using a commercially available kit essentially as described by the manufacturer (TdT-FragEL, Oncogene Research Products). The DNA-incorporated biotinylated nucleotides was detected using a streptavidin-horseradish peroxidase conjugate and reaction with the colorometric substrate diaminobenzidine. A light counter-staining with hematoxylin was performed to help with the morphological evaluation and characterization of normal and apoptotic cells. Negative controls included substituting dH$_2$O for the TdT during the labeling step. This assay has been validated by performing preliminary experiments using intestinal tissue from normal and UV-irradiated mice.

Results

Addition of RDP58 to PMPA therapy or RDP58 alone had no adverse effect on the suppression of viral loads. Administration of RDP58 in combination with PMPA therapy had beneficial effect on restoration of CD4$^+$ single positive and CD4$^+$CD8$^+$ double positive T-cells in the jejunal mucosa as compared to untreated animals. RDP58 appears to have beneficial effects on stabilizing CD4$^+$ T-cell population in GALT.

What is claimed:

1. A method for treating an individual infected with HIV, comprising administering to an HIV infected individual a pharmaceutically effective amount of
   a) an immunomodulatory peptide; and
   b) at least one anti-retroviral agent;
   wherein said immunomodulatory peptide is an oligopeptide is selected from the group consisting of:
   (a) Arg-Leu-Leu-Leu-Arg-Leu-Leu-Leu-Gly-Tyr (SEQ ID NO:10);
   (b) Arg-Val-Leu-Leu-Arg-Leu-Leu-Leu-Gly-Tyr (SEQ ID NO:11);
   (c) Arg-Ile-Leu-Leu-Arg-Leu-Leu-Leu-Gly-Tyr (SEQ ID NO:12);
   (d) Arg-Leu-Val-Leu-Arg-Leu-Leu-Leu-Gly-Tyr (SEQ ID NO:13);
   (e) Arg-Leu-Ile-Leu-Arg-Leu-Leu-Leu-Gly-Tyr (SEQ ID NO:14);
   (f) Arg-Leu-Leu-Val-Arg-Leu-Leu-Leu-Gly-Tyr (SEQ ID NO:15);
   (g) Arg-Leu-Leu-Ile-Arg-Leu-Leu-Leu-Gly-Tyr (SEQ ID NO:16);
   (h) Arg-Leu-Leu-Leu-Arg-Val-Leu-Leu-Gly-Tyr (SEQ ID NO:17);
   (i) Arg-Leu-Leu-Leu-Arg-Ile-Leu-Leu-Gly-Tyr (SEQ ID NO:18);
   (j) Arg-Leu-Leu-Leu-Arg-Leu-Val-Leu-Gly-Tyr (SEQ ID NO:19);
   (k) Arg-Leu-Leu-Leu-Arg-Leu-Ile-Leu-Gly-Tyr (SEQ ID NO:20);
   (l) Arg-Leu-Leu-Leu-Arg-Leu-Leu-Val-Gly-Tyr (SEQ ID NO:21);
   (m) Arg-Leu-Leu-Leu-Arg-Leu-Leu-Ile-Gly-Tyr (SEQ ID NO:22);
   (n) Arg-Trp-Leu-Leu-Arg-Leu-Leu-Leu-Gly-Tyr (SEQ ID NO:23);
   (o) Arg-Leu-Trp-Leu-Arg-Leu-Leu-Leu-Gly-Tyr (SEQ ID NO:24);
   (p) Arg-Leu-Leu-Trp-Arg-Leu-Leu-Leu-Gly-Tyr (SEQ ID NO:25);
   (q) Arg-Leu-Leu-Leu-Arg-Trp-Leu-Leu-Gly-Tyr (SEQ ID NO:26);
   (r) Arg-Leu-Leu-Leu-Arg-Leu-Trp-Leu-Gly-Tyr (SEQ ID NO:27);
   (s) Arg-Leu-Leu-Leu-Arg-Leu-Leu-Trp-Gly-Tyr (SEQ ID NO:28);
   (t) Arg-Tyr-Leu-Leu-Arg-Leu-Leu-Leu-Gly-Tyr (SEQ ID NO:29);
   (u) Arg-Leu-Tyr-Leu-Arg-Leu-Leu-Leu-Gly-Tyr (SEQ ID NO:30);
   (v) Arg-Leu-Leu-Tyr-Arg-Leu-Leu-Leu-Gly-Tyr (SEQ ID NO:31);
   (w) Arg-Leu-Leu-Leu-Arg-Tyr-Leu-Leu-Gly-Tyr (SEQ ID NO:32);
   (x) Arg-Leu-Leu-Leu-Arg-Leu-Tyr-Leu-Gly-Tyr (SEQ ID NO:33);
   (y) Arg-Leu-Leu-Leu-Arg-Leu-Leu-Tyr-Gly-Tyr (SEQ ID NO:34); and
   (z) Arg-nL-nL-nL-Arg-nL-nL-nL-Gly-Tyr (SEQ ID NO:1).

2. A method for treating an individual infected with HIV, comprising administering to an HIV infected individual a pharmaceutically effective amount of
   a) an oligopeptide comprising the sequence Arg-nL-nL-nL-Arg-nL-nL-nL-Gly-Tyr (SEQ ID NO:1) and wherein nL is norleucine and all amino acids other than glycine are the D-stereoisomers; and
   b) at least one anti-retroviral agent.

3. A method according to claim 1, wherein a combination of a plurality of anti-retroviral agents are administered.

4. A method according to claim 1, wherein said anti-retroviral agent is a reverse transcriptase inhibitor.

5. A method according to claim 1, wherein said anti-retroviral agent is a nucleoside reverse transcriptase inhibitor.

6. A method according to claim 1, wherein said anti-retroviral agent is a non-nucleoside reverse transcriptase inhibitor.

7. A method according to claim 1, wherein said anti-retroviral agent is a protease inhibitor.

8. A method according to claim 3 wherein said combination comprises a reverse transcriptase inhibitor and a protease inhibitor.

9. A method according to claim 3, wherein said combination comprises a nucleoside reverse transcriptase inhibitor, a non-nucleoside reverse transcriptase inhibitor, and a protease inhibitor.

10. A method according to claim 1, wherein said anti-retroviral agent is selected from the group consisting of nucleoside reverse transcriptase inhibitors, non-nucleoside reverse transcriptase inhibitors, protease inhibitors, co-receptor antagonists, retroviral integrase inhibitors, viral adsorption inhibitors, viral specific transcription inhibitors, and cyclin dependent kinase inhibitors.

11. A method according to claim 1, wherein said oligopeptide and said anti-retroviral agent are administered simultaneously.

12. A method according to claim 1, wherein said oligopeptide and said anti-retroviral agent are administered sequentially.

13. A method according to claim 1, wherein said treating is for gastrointestinal complications associated with HIV infection.

14. A method according to claim 13, wherein said gastrointestinal complications is an inflammatory reaction associated with said HIV infection.

15. A method according to claim 1, wherein said administration is by oral administration.

16. A method according to claim 1, wherein said administration is by intravenous administration.

17. A method according to claim 1, wherein further comprising administering an additional therapeutic agent.

18. A method according to claim 17, wherein said additional therapeutic agent is a cytokine or hydroxyurea.

19. A method according to claim 1, wherein said oligopeptide comprises the sequence Arg-nL-nL-nL-Arg-nL-nL-nL-Gly-Tyr (SEQ ID NO:1) and wherein nL is norleucine.

* * * * *

SEQUENCE LISTING

```
<160> NUMBER OF SEQ ID NOS: 36

<210> SEQ ID NO 1
<211> LENGTH: 10
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (2)..(8)
<223> OTHER INFORMATION: Xaa at positions 2-4 and 6-8 is norleucine

<400> SEQUENCE: 1

Arg Xaa Xaa Xaa Arg Xaa Xaa Xaa Gly Tyr
1               5                   10

<210> SEQ ID NO 2
<211> LENGTH: 5
<212> TYPE: PRT
<213> ORGANISM: Artificial sequence
<220> FEATURE:
<223> OTHER INFORMATION: Linker consensus sequence

<400> SEQUENCE: 2

Gly Ser Gly Gly Ser
1               5

<210> SEQ ID NO 3
<211> LENGTH: 4
<212> TYPE: PRT
<213> ORGANISM: Artificial sequence
<220> FEATURE:
<223> OTHER INFORMATION: Linker consensus sequence

<400> SEQUENCE: 3

Gly Gly Gly Ser
1

<210> SEQ ID NO 4
<211> LENGTH: 32
<212> TYPE: PRT
<213> ORGANISM: Artificial sequence
<220> FEATURE:
<223> OTHER INFORMATION: Zinc finger consensus sequence
<220> FEATURE:
<221> NAME/KEY: MISC_FEATURE
<222> LOCATION: (1)..(5)
<223> OTHER INFORMATION: Xaa at positions 1-5 can be any amino acid
<220> FEATURE:
<221> NAME/KEY: MISC_FEATURE
<222> LOCATION: (7)..(9)
<223> OTHER INFORMATION: Xaa at positions 7-9 can be any amino acid,
      where one of amino acids 7-9 can be absent
```

-continued

```
<220> FEATURE:
<221> NAME/KEY: MISC_FEATURE
<222> LOCATION: (11)..(22)
<223> OTHER INFORMATION: Xaa at positions 11-22 can be any amino acid,
      where up to 8 of amino acids 11-22 can be
      absent
<220> FEATURE:
<221> NAME/KEY: MISC_FEATURE
<222> LOCATION: (24)..(32)
<223> OTHER INFORMATION: Xaa at positions 24-26 and 28-32 can be any
      amino acid

<400> SEQUENCE: 4

Xaa Xaa Xaa Xaa Xaa Cys Xaa Xaa Xaa Cys Xaa Xaa Xaa Xaa Xaa Xaa
1               5                   10                  15

Xaa Xaa Xaa Xaa Xaa Xaa His Xaa Xaa Xaa His Xaa Xaa Xaa Xaa Xaa
            20                  25                  30

<210> SEQ ID NO 5
<211> LENGTH: 33
<212> TYPE: PRT
<213> ORGANISM: Artificial sequence
<220> FEATURE:
<223> OTHER INFORMATION: C2H2 zinc finger consensus sequence
<220> FEATURE:
<221> NAME/KEY: MISC_FEATURE
<222> LOCATION: (7)..(26)
<223> OTHER INFORMATION: Xaa at positions 7-26 can be any amino acid,
      where up to 17 of amino acids 7-26 can be
      absent

<400> SEQUENCE: 5

Phe Gln Cys Glu Glu Cys Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa His Ile Arg Ser His Thr
            20                  25                  30

Gly

<210> SEQ ID NO 6
<211> LENGTH: 30
<212> TYPE: PRT
<213> ORGANISM: Artificial sequence
<220> FEATURE:
<223> OTHER INFORMATION: CCHC box consensus sequence
<220> FEATURE:
<221> NAME/KEY: MISC_FEATURE
<222> LOCATION: (2)..(3)
<223> OTHER INFORMATION: Xaa at positions 2-3 can be any amino acid
<220> FEATURE:
<221> NAME/KEY: MISC_FEATURE
<222> LOCATION: (5)..(24)
<223> OTHER INFORMATION: Xaa at positions 5-24 can be any amino acid,
      where up to 16 of amino acids 5-24 can be
      absent
<220> FEATURE:
<221> NAME/KEY: MISC_FEATURE
<222> LOCATION: (26)..(29)
<223> OTHER INFORMATION: Xaa at positions 26-29 can be any amino acid

<400> SEQUENCE: 6

Cys Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa His Xaa Xaa Xaa Xaa Cys
            20                  25                  30

<210> SEQ ID NO 7
<211> LENGTH: 33
<212> TYPE: PRT
<213> ORGANISM: Artificial sequence
```

```
<220> FEATURE:
<223> OTHER INFORMATION: CCHC box consensus sequence
<220> FEATURE:
<221> NAME/KEY: MISC_FEATURE
<222> LOCATION: (7)..(26)
<223> OTHER INFORMATION: Xaa at positions 7-26 can be any amino acid,
                         where up to 16 of amino acids 7-26 can be
                         absent

<400> SEQUENCE: 7

Val Lys Cys Phe Asn Cys Xaa Xaa Xaa Xaa Xaa Xaa Xaa Xaa Xaa
1               5                  10                  15

Xaa Xaa Xaa Xaa Xaa Xaa Xaa Xaa Xaa Xaa His Thr Ala Arg Asn Cys
            20                  25                  30

Arg

<210> SEQ ID NO 8
<211> LENGTH: 34
<212> TYPE: PRT
<213> ORGANISM: Artificial sequence
<220> FEATURE:
<223> OTHER INFORMATION: CCHC box consensus sequence
<220> FEATURE:
<221> NAME/KEY: MISC_FEATURE
<222> LOCATION: (10)..(29)
<223> OTHER INFORMATION: Xaa at positions 10-29 can be any amino acid,
                         where up to 16 of amino acids 10-29 can be
                         absent

<400> SEQUENCE: 8

Met Asn Pro Asn Cys Ala Arg Cys Gly Xaa Xaa Xaa Xaa Xaa Xaa
1               5                  10                  15

Xaa Xaa Xaa Xaa Xaa Xaa Xaa Xaa Xaa Xaa Xaa Xaa Xaa His Lys Ala
            20                  25                  30

Cys Phe

<210> SEQ ID NO 9
<211> LENGTH: 10
<212> TYPE: PRT
<213> ORGANISM: Artificial sequence
<220> FEATURE:
<223> OTHER INFORMATION: Synthetic

<400> SEQUENCE: 9

Arg Val Asn Leu Arg Ile Ala Leu Arg Tyr
1               5                  10

<210> SEQ ID NO 10
<211> LENGTH: 10
<212> TYPE: PRT
<213> ORGANISM: Artificial sequence
<220> FEATURE:
<223> OTHER INFORMATION: Synthetic

<400> SEQUENCE: 10

Arg Leu Leu Leu Arg Leu Leu Leu Gly Tyr
1               5                  10

<210> SEQ ID NO 11
<211> LENGTH: 10
<212> TYPE: PRT
<213> ORGANISM: Artificial sequence
<220> FEATURE:
<223> OTHER INFORMATION: synthetic

<400> SEQUENCE: 11
```

```
Arg Val Leu Leu Arg Leu Leu Leu Gly Tyr
1               5                   10

<210> SEQ ID NO 12
<211> LENGTH: 10
<212> TYPE: PRT
<213> ORGANISM: Artificial sequence
<220> FEATURE:
<223> OTHER INFORMATION: synthetic

<400> SEQUENCE: 12

Arg Ile Leu Leu Arg Leu Leu Leu Gly Tyr
1               5                   10

<210> SEQ ID NO 13
<211> LENGTH: 10
<212> TYPE: PRT
<213> ORGANISM: Artificial sequence
<220> FEATURE:
<223> OTHER INFORMATION: synthetic

<400> SEQUENCE: 13

Arg Leu Val Leu Arg Leu Leu Leu Gly Tyr
1               5                   10

<210> SEQ ID NO 14
<211> LENGTH: 10
<212> TYPE: PRT
<213> ORGANISM: Artificial sequence
<220> FEATURE:
<223> OTHER INFORMATION: synthetic

<400> SEQUENCE: 14

Arg Leu Ile Leu Arg Leu Leu Leu Gly Tyr
1               5                   10

<210> SEQ ID NO 15
<211> LENGTH: 10
<212> TYPE: PRT
<213> ORGANISM: Artificial sequence
<220> FEATURE:
<223> OTHER INFORMATION: synthetic

<400> SEQUENCE: 15

Arg Leu Leu Val Arg Leu Leu Leu Gly Tyr
1               5                   10

<210> SEQ ID NO 16
<211> LENGTH: 10
<212> TYPE: PRT
<213> ORGANISM: Artificial sequence
<220> FEATURE:
<223> OTHER INFORMATION: synthetic

<400> SEQUENCE: 16

Arg Leu Leu Ile Arg Leu Leu Leu Gly Tyr
1               5                   10

<210> SEQ ID NO 17
<211> LENGTH: 10
<212> TYPE: PRT
<213> ORGANISM: Artificial sequence
<220> FEATURE:
<223> OTHER INFORMATION: synthetic

<400> SEQUENCE: 17

Arg Leu Leu Leu Arg Val Leu Leu Gly Tyr
```

```
1               5                  10
```

<210> SEQ ID NO 18
<211> LENGTH: 10
<212> TYPE: PRT
<213> ORGANISM: Artificial sequence
<220> FEATURE:
<223> OTHER INFORMATION: synthetic

<400> SEQUENCE: 18

```
Arg Leu Leu Leu Arg Ile Leu Leu Gly Tyr
1               5                  10
```

<210> SEQ ID NO 19
<211> LENGTH: 10
<212> TYPE: PRT
<213> ORGANISM: Artificial sequence
<220> FEATURE:
<223> OTHER INFORMATION: synthetic

<400> SEQUENCE: 19

```
Arg Leu Leu Leu Arg Leu Val Leu Gly Tyr
1               5                  10
```

<210> SEQ ID NO 20
<211> LENGTH: 10
<212> TYPE: PRT
<213> ORGANISM: Artificial sequence
<220> FEATURE:
<223> OTHER INFORMATION: synthetic

<400> SEQUENCE: 20

```
Arg Leu Leu Leu Arg Leu Ile Leu Gly Tyr
1               5                  10
```

<210> SEQ ID NO 21
<211> LENGTH: 10
<212> TYPE: PRT
<213> ORGANISM: Artificial sequence
<220> FEATURE:
<223> OTHER INFORMATION: synthetic

<400> SEQUENCE: 21

```
Arg Leu Leu Leu Arg Leu Leu Val Gly Tyr
1               5                  10
```

<210> SEQ ID NO 22
<211> LENGTH: 10
<212> TYPE: PRT
<213> ORGANISM: Artificial sequence
<220> FEATURE:
<223> OTHER INFORMATION: synthetic

<400> SEQUENCE: 22

```
Arg Leu Leu Leu Arg Leu Leu Ile Gly Tyr
1               5                  10
```

<210> SEQ ID NO 23
<211> LENGTH: 10
<212> TYPE: PRT
<213> ORGANISM: Artificial sequence
<220> FEATURE:
<223> OTHER INFORMATION: synthetic

<400> SEQUENCE: 23

```
Arg Trp Leu Leu Arg Leu Leu Leu Gly Tyr
1               5                  10
```

<210> SEQ ID NO 24
<211> LENGTH: 10
<212> TYPE: PRT
<213> ORGANISM: Artificial sequence
<220> FEATURE:
<223> OTHER INFORMATION: synthetic

<400> SEQUENCE: 24

Arg Leu Trp Leu Arg Leu Leu Leu Gly Tyr
1               5                   10

<210> SEQ ID NO 25
<211> LENGTH: 10
<212> TYPE: PRT
<213> ORGANISM: Artificial sequence
<220> FEATURE:
<223> OTHER INFORMATION: synthetic

<400> SEQUENCE: 25

Arg Leu Leu Trp Arg Leu Leu Leu Gly Tyr
1               5                   10

<210> SEQ ID NO 26
<211> LENGTH: 10
<212> TYPE: PRT
<213> ORGANISM: Artificial sequence
<220> FEATURE:
<223> OTHER INFORMATION: synthetic

<400> SEQUENCE: 26

Arg Leu Leu Leu Arg Trp Leu Leu Gly Tyr
1               5                   10

<210> SEQ ID NO 27
<211> LENGTH: 10
<212> TYPE: PRT
<213> ORGANISM: Artificial sequence
<220> FEATURE:
<223> OTHER INFORMATION: synthetic

<400> SEQUENCE: 27

Arg Leu Leu Leu Arg Leu Trp Leu Gly Tyr
1               5                   10

<210> SEQ ID NO 28
<211> LENGTH: 10
<212> TYPE: PRT
<213> ORGANISM: Artificial sequence
<220> FEATURE:
<223> OTHER INFORMATION: synthetic

<400> SEQUENCE: 28

Arg Leu Leu Leu Arg Leu Leu Trp Gly Tyr
1               5                   10

<210> SEQ ID NO 29
<211> LENGTH: 10
<212> TYPE: PRT
<213> ORGANISM: Artificial sequence
<220> FEATURE:
<223> OTHER INFORMATION: synthetic

<400> SEQUENCE: 29

Arg Tyr Leu Leu Arg Leu Leu Leu Gly Tyr
1               5                   10

-continued

<210> SEQ ID NO 30
<211> LENGTH: 10
<212> TYPE: PRT
<213> ORGANISM: Artificial sequence
<220> FEATURE:
<223> OTHER INFORMATION: synthetic

<400> SEQUENCE: 30

Arg Leu Tyr Leu Arg Leu Leu Leu Gly Tyr
1               5                   10

<210> SEQ ID NO 31
<211> LENGTH: 10
<212> TYPE: PRT
<213> ORGANISM: Artificial sequence
<220> FEATURE:
<223> OTHER INFORMATION: synthetic

<400> SEQUENCE: 31

Arg Leu Leu Tyr Arg Leu Leu Leu Gly Tyr
1               5                   10

<210> SEQ ID NO 32
<211> LENGTH: 10
<212> TYPE: PRT
<213> ORGANISM: Artificial sequence
<220> FEATURE:
<223> OTHER INFORMATION: synthetic

<400> SEQUENCE: 32

Arg Leu Leu Leu Arg Tyr Leu Leu Gly Tyr
1               5                   10

<210> SEQ ID NO 33
<211> LENGTH: 10
<212> TYPE: PRT
<213> ORGANISM: Artificial sequence
<220> FEATURE:
<223> OTHER INFORMATION: synthetic

<400> SEQUENCE: 33

Arg Leu Leu Leu Arg Leu Tyr Leu Gly Tyr
1               5                   10

<210> SEQ ID NO 34
<211> LENGTH: 10
<212> TYPE: PRT
<213> ORGANISM: Artificial sequence
<220> FEATURE:
<223> OTHER INFORMATION: synthetic

<400> SEQUENCE: 34

Arg Leu Leu Leu Arg Leu Leu Tyr Gly Tyr
1               5                   10

<210> SEQ ID NO 35
<211> LENGTH: 10
<212> TYPE: PRT
<213> ORGANISM: Homo sapiens

<400> SEQUENCE: 35

Arg Glu Asn Leu Arg Ile Ala Leu Arg Tyr
1               5                   10

<210> SEQ ID NO 36
<211> LENGTH: 7

```
-continued

<212> TYPE: PRT
<213> ORGANISM: Artificial sequence
<220> FEATURE:
<223> OTHER INFORMATION: Linker sequence
<220> FEATURE:
<221> NAME/KEY: MISC_FEATURE
<222> LOCATION: (1)..(7)
<223> OTHER INFORMATION: Up to 6 of amino acids 1-7 can be absent

<400> SEQUENCE: 36

Gly Gly Gly Gly Gly Gly Gly
1               5
```